(12) United States Patent
Kuppusamy et al.

(10) Patent No.: US 7,662,362 B2
(45) Date of Patent: Feb. 16, 2010

(54) NANOPARTICULATE PROBE FOR IN VIVO MONITORING OF TISSUE OXYGENATION

(75) Inventors: Periannan Kuppusamy, New Albany, OH (US); Ramasamy P. Pandian, Columbus, OH (US); Narasimham L. Parinandi, Upper Arlington, OH (US); Jay L. Zweier, Blacklick, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 711 days.

(21) Appl. No.: 10/935,297

(22) Filed: Sep. 7, 2004

(65) Prior Publication Data

US 2005/0203292 A1 Sep. 15, 2005

Related U.S. Application Data

(60) Provisional application No. 60/500,714, filed on Sep. 5, 2003.

(51) Int. Cl.
*A61B 5/055* (2006.01)
*C07B 47/00* (2006.01)
*C07D 487/22* (2006.01)
(52) U.S. Cl. ......................... 424/9.3; 540/145
(58) Field of Classification Search ................. 540/145; 424/9.3
See application file for complete search history.

(56) References Cited

U.S. PATENT DOCUMENTS

| | | | |
|---|---|---|---|
| 4,996,311 A | 2/1991 | Moussavvi et al. | |
| 5,045,440 A | 9/1991 | Onorato et al. | |
| 5,112,597 A | 5/1992 | Moussavvi et al. | |
| 5,258,313 A * | 11/1993 | Moussavi | 436/136 |
| 5,494,030 A | 2/1996 | Swartz et al. | |
| 5,607,762 A * | 3/1997 | Albert et al. | 428/321.3 |
| 5,706,805 A | 1/1998 | Swartz et al. | |
| 5,765,562 A | 6/1998 | Leunbach et al. | |
| 5,833,601 A | 11/1998 | Swartz et al. | |
| 5,965,598 A | 10/1999 | Ronucci et al. | |
| 6,060,598 A | 5/2000 | Devlin et al. | |
| 6,108,574 A * | 8/2000 | Ardenkjaer-Larsen | 600/420 |
| 6,256,527 B1 | 7/2001 | Leunbach et al. | |
| 6,391,646 B1 | 5/2002 | Khangulov | |
| 6,573,720 B1 | 6/2003 | Devasahayam et al. | |
| 2007/0041909 A1 | 2/2007 | Kupusamy et al. | |

FOREIGN PATENT DOCUMENTS

| EP | 0 871 896 B1 | | 1/2002 |
|---|---|---|---|
| EP | 0871896 B1 | * | 1/2002 |
| WO | 94/02865 | | 2/1994 |
| WO | 96/39933 | | 12/1996 |
| WO | 2005/024442 | | 3/2005 |

OTHER PUBLICATIONS

Liu et al., "Liithum phthalocyanine . . . " Proc. Nat'l Acad. Scil USA vol. 90, pp. 5438-5442, (1993).*
Liu et al., Proc. Natl. Acad Sci. "lithium phthalocyanine . . . ", vol. 90, pp. 5438-5442, 1993.*
Lui et al., "Lithium Phthalocyanine: A Probe for Electron Paramagnetic Resonance Oximetry in Viable Biological Systems," Proc. Natl. Acad. Sci., vol. 90, pp. 5438-5442, 1993.
Manivannan et al., "Lithium Naphthalocyanine as a New Molecular Radical Probe for Electron Paramagnetic Resonance Oximetry," J. Magnetism and Magnetic Mat. 2001, vol. 233, pp. L131-L135.
PCT/US04/28821—International Search Report—Mailed Jul. 6, 2005.
PCT/US04/28821—Written Opinion Mailed Jul. 6, 2005.
PCT/US04/28821—IPRP Issued Mar. 6, 2006.
[Abstract] Kuppusamy et al., "Measurement of Intracellular Oxygen Concentration Using Nanoparticulate Probes", 10th Conference in Vivo EPR Spectroscopy and Imaging, Univ. of Fukuoka, Fukuoka City, Japan, Apr. 1-3, 2003.
[Slide Show Presentation] Kuppusamy et al., "Measurement of Intracellular Oxygen Concentration Using Nanoparticulate Probes", 10th Conference in Vivo EPR Spectroscopy and Imaging, Univ. of Fukuoka, Fukuoka City, Japan, Apr. 1-3, 2003.
Liu et al., "Lithium Phthalocyanine: A Probe for Electron Paramagnetic Resonance Oximetry in Viable Biological Systems", Proc. Natl. Acad. Sci. (Jun. 1993), vol. 90, pp. 5438-5448.
Manivannan et al., "Lithium naphthalocyanine as a new molecular radical probe for electron paramagnetic resonance oximetry", J. Magnetism and Magnetic Mat. (2001), vol. 233, pp. L131-L135.
Motterlini et al. "Depression of endothelial and smooth muscle cell oxygen consumption by endotoxin", Am. J. Physiology (Sep. 1998), vol. 275, No. 3 Pt. 2, pp. H776-H782.
Ruehm et al., "Magnetic Resonance Imaging of Atherosclerotic Plaque With Ultrasmall Superparamagnetic Particles of Iron Oxide in Hyperlipidemic Rabbits", Circulation (2001), vol. 103, pp. 415-422.

* cited by examiner

*Primary Examiner*—James O. Wilson
*Assistant Examiner*—Paul V. Ward
(74) *Attorney, Agent, or Firm*—Calfee, Halter and Griswold LLP

(57) ABSTRACT

A new class of micro- and nano-particulate paramagnetic spin probes especially useful for magnetic resonance imaging techniques, including electron paramagnetic resonance (EPR) and magnetic resonance imaging (MRI). The probes are lithium phthalocyanine derivative compounds. Also provided are suspensions and emulsions comprising lithium phthalocyanine derivative probes. Also provided are noninvasive methods for measuring noninvasive methods of measuring oxygen concentration, oxygen partial pressure, oxygen metabolism, and nitric oxide concentration in a specific tissue, organ, or cell in vivo or in vitro.

22 Claims, 22 Drawing Sheets

R = O(CH₂)₃CH₃

NANOPARTICULATE PROBE FOR IN VIVO MONITORING OF TISSUE OXYGENATION

CROSS-REFERENCE TO RELATED APPLICATIONS

This application claims priority to U.S. Provisional Patent Application Ser. No. 60/500,714 filed Sep. 5, 2003, the entirety of which is incorporated herein by reference.

STATEMENT ON FEDERALLY FUNDED RESEARCH

This invention was funded at least in part by the National Institutes of Health, grant CA78886. The government may have certain rights in this invention.

BACKGROUND OF THE INVENTION

Over the last decade, it has become clear that cigarette smoking induces lung cancer and vascular disease. It is a major risk factor in the occurrence of heart attack and stroke. Vascular disease leads to tissue damage including heart attack and stroke and is by far the leading cause of morbidity and mortality in the United States. Tobacco use leads to tissue injury in the lungs, heart and vasculature and is implicated in approximately 20% of all deaths in the United States. Tobacco induced peripheral vascular disease results in a broad range of medical complications including vascular insufficiency, claudication, stasis ulcers, wound formation, impaired wound healing and chronic wounds.

Cigarette smoke has a very high content of free radicals, molecules with unpaired electron spin, that are highly reactive and once present in cells and tissues induce lipid, protein and DNA damage. These free radicals as well as secondary oxygen and nitrogen centered radicals are the key radical species that trigger tobacco-induced carcinogenesis, as well as cardiovascular and lung injury. Oxygen radicals can trigger an inflammatory response through leukocyte chemotaxis and activation that in turn results in a vicious cycle of further oxidant formation and inflammation. Investigators of this program have demonstrated that oxygen radicals induce cellular proliferation, a key process in the pathogenesis of cancer and atherosclerosis [5].

In just over two decades the advent of magnetic resonance imaging (MRI) has revolutionized the practice of medicine. At an ever-accelerating rate MRI has achieved breakthroughs first in enabling high-resolution anatomical imaging of tissue abnormalities in disease and more recently alterations in organ function. With the advent of molecular medicine and targeted therapeutics as well as the breakthroughs in the sequencing of the human genome, it has been realized that potentially the next even more powerful horizon for magnetic resonance imaging is in the imaging of molecular and gene expression that will enable the early detection or prevention of disease as well as facilitate the treatment and cure of existing illness.

Electron paramagnetic resonance (EPR) has advantages over proton NMR in that it is inherently over 1,000 times more sensitive on a spin basis and furthermore, for a given frequency, measurements may be performed at much lower magnetic fields enabling the use of low-cost magnet systems. Over the last several years, it has been shown that the electron spin-based technique of EPR imaging (EPRI) can provide high sensitivity and high resolution images of paramagnetic materials. For example at 1200 MHz it was shown that concentrations as low as 10 nM could be detected for a typical nitroxide spin label and this sensitivity is at least two orders of magnitude above that achievable even with ultra high-field proton MRI [1]. In addition, it was shown that high-resolution 3D images may be obtained with submillimeter resolution. In addition to direct EPR detection of paramagnetic spin probes, the hybrid EPR/NMR technique of Proton Electron Double Resonance Imaging (PEDRI) can also detect paramagnetic probes by the marked Overhauser enhancement observed in proton MRI signal seen upon irradiation of the electron spin. Enhancements of over 100 fold may be achieved. These enhancements translate into markedly improved image quality, contrast and resolution in biological tissues. With this marked enhancement, proton magnetization and image quality even at relatively low fields can exceed that of the highest field MRI systems. For example, in principle, PEDRI image quality at 0.2T could exceed that at 20 T, if indeed such an ultra high-field system could be built.

With recent technological advances, it has become possible to image these critical free radical mediators of disease using novel magnetic resonance imaging techniques. Advances in the magnetic resonance imaging techniques of in vivo Electron Paramagnetic Resonance Imaging (EPRI) and Proton Electron Double Resonance Imaging (PEDRI) have enabled the imaging of these critical mediators of disease and the redox stress they cause in living animals and most recently in man [2, 3, 6, 7]. These MR techniques along with new types of spin probes and spin traps as well as innovative nanoparticulate probes have enabled the imaging of free radicals, oxygen and nitric oxide [1, 8-13]. These breakthroughs have the potential to revolutionize the diagnosis and treatment of human disease. Beyond their diagnostic power, spin traps have great potential for the treatment of disease since they can trap or scavenge free radicals preventing radical-induced molecular and cellular damage. Free radicals, both extrinsic as from cigarette smoke, or intrinsic, from inflammatory stress, are central in the pathogenesis of human disease including: heart attack, stroke, cancer, neurodegenerative diseases, emphysema/obstructive pulmonary disease as well as the process of aging. The ability to trap and scavenge these critical mediators of disease has the potential to revolutionize current medical diagnosis and treatment and provide the long-awaited cures to a variety of the diseases that have plagued mankind.

While a great wealth of information may be obtained from the imaging of intrinsic protons, to achieve MR-based imaging of molecular and gene expression, there is a critical need for new imaging agents that may be designed or targeted to visualize specific molecular targets. There is also a need for probes that can be tagged to proteins or DNA, enabling generalized biomolecular and gene imaging. There is further a need, in addition to detecting these materials through their effects on proton relaxation, for the ability to directly detect paramagnetic materials using the MR technique of Electron Paramagnetic Resonance (EPR) or other MR techniques. Additionally, there is a need for new particulate probes that may be used to accurately determine oxygen concentration in cells.

SUMMARY OF THE INVENTION

The present invention provides a new class of particulate probes that are especially useful for magnetic resonance imaging techniques. The particulate probes are nanoparticulate and microparticulate probes comprising paramagnetic spin probes that are especially suitable for use with magnetic resonance (MR) techniques, particularly, but not limited to, electron paramagnetic resonance (EPR) and magnetic resonance imaging (MRI). The nanoparticulate and microparticulate probes comprise radicals of lithium phthalocyanine derivative compounds, which include lithium phthalocyanine derivatives, lithium naphthalocyanine derivatives, and lithium anthraphthalocyanine derivatives.

The probes preferably have a size of 10 microns or less, more preferably from 0.22 to 10 microns, and for intravenous applications, even more preferably less than 0.22 microns. The probes may be used with a variety of MR spectroscopy and MR imaging techniques, including but not limited to magnetic resonance imaging (MRI); electron spin resonance (ESR); electron paramagnetic resonance (EPR); electron paramagnetic resonance imaging (EPRI); and proton electron double resonance imaging (PEDRI).

The probes of the present invention comprise ligands, dilithium complexes, and lithium radicals. Some preferred dilithium complexes are shown as compounds 1-6:

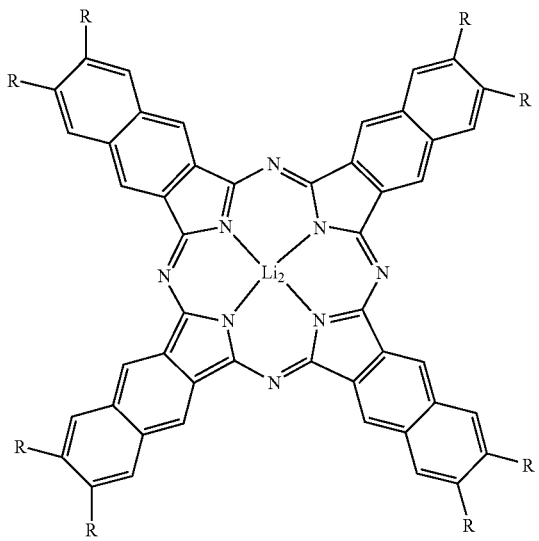

[1]

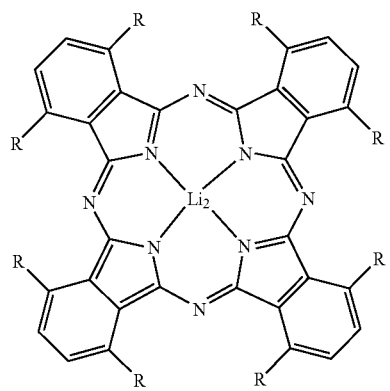

[2]

-continued

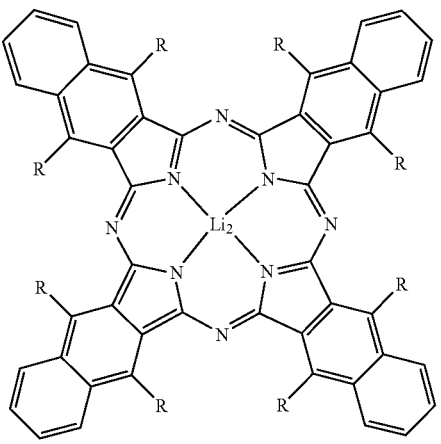

[3]

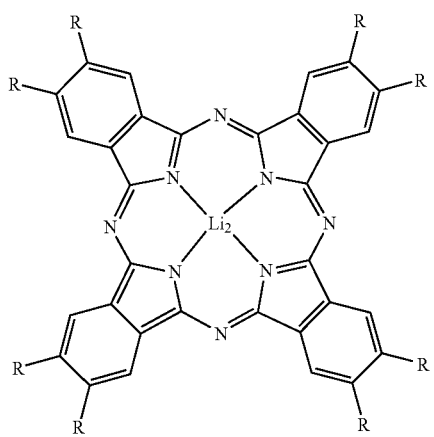

[4]

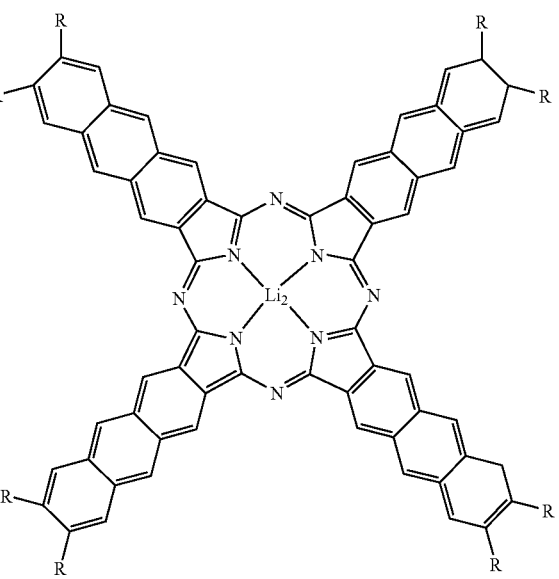

[5]

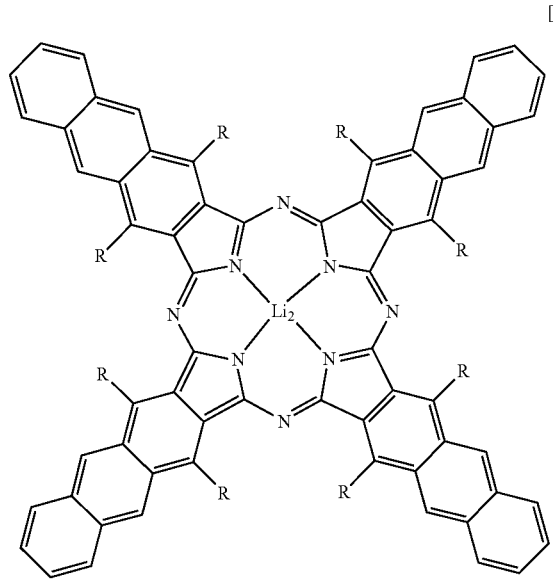

[6]

wherein R is selected from the group consisting of $O(CH_2)_nCH_3$, $S(CH_2)_nCH_3$, $O(CH_2)_nCH_2OH$, $O(CH_2)_nCH_2NH_2$, $O(CH_2)_nCH_2SH$, and combinations thereof; wherein n is 1-6. Preferred lithium radicals are obtained from these dilithium complexes by electrochemical or chemical oxidation.

Also provided are suspensions and emulsions comprising lithium phthalocyanine derivative radicals, which have an oxygen center, making them useful for various in vivo and in vitro measurements. The suspensions of the present invention are in a media selected nonphysiological media, physiological media, buffers, and combinations thereof. The particulate probes are selected from the group consisting of:

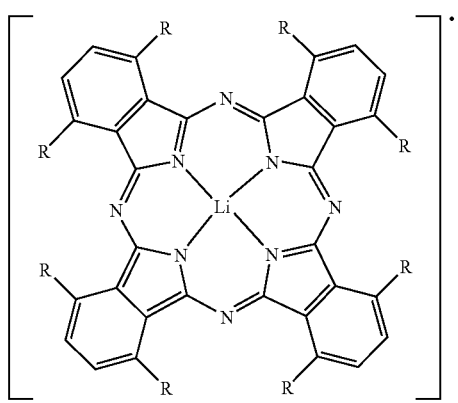

[R1]

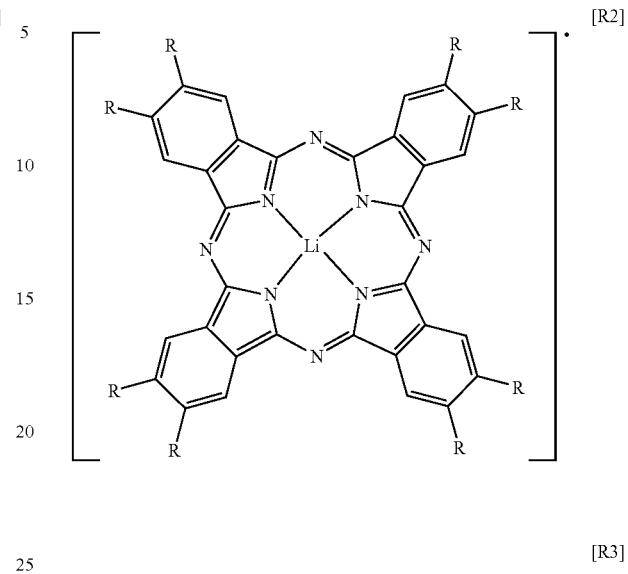

[R2]

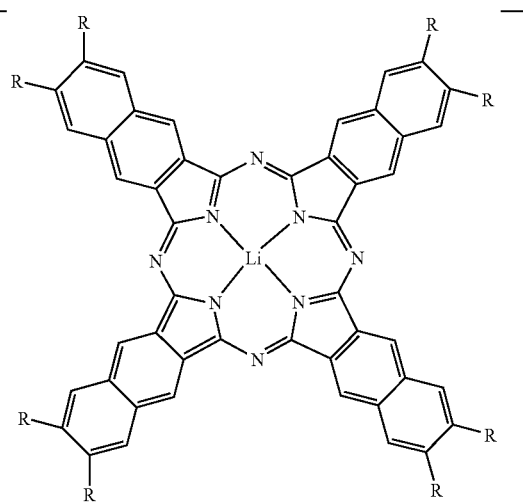

[R3]

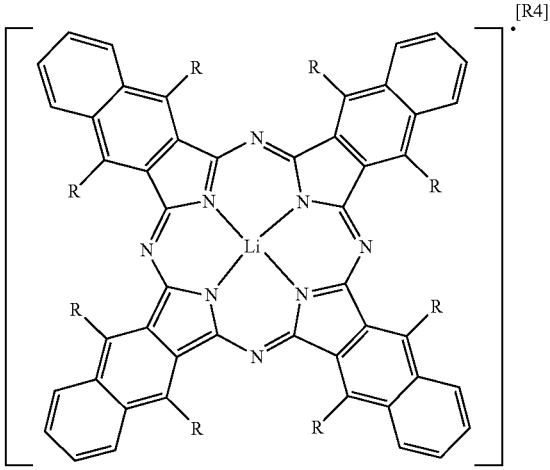

[R4]

-continued

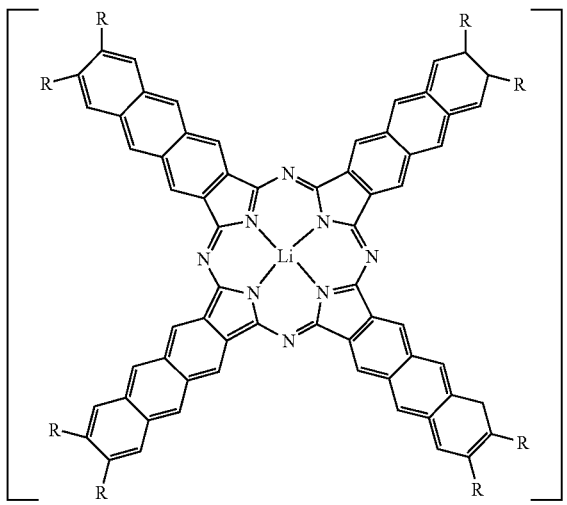

[R5]

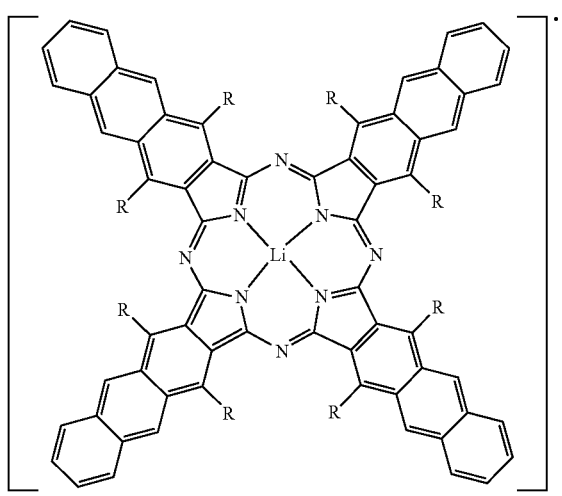

[R6]

wherein R is selected from the group consisting of O(CH$_2$)$_n$CH$_3$, S(CH$_2$)$_n$CH$_3$, O(CH$_2$)$_n$CH$_2$OH, O(CH$_2$)$_n$CH$_2$NH$_2$, O(CH$_2$)$_n$CH$_2$SH, and combinations thereof; and wherein n is 1-6; and combinations thereof.

The suspensions of the present invention further comprise a stabilizing agent and/or a stabilizing media. Some preferred stabilizing agents are selected from, but not limited to amino acids, synthetic peptides, peptides of natural origin, proteins, sugars, carbohydrates, nucleic acid homopolymers, amino acid homopolymers, DNA, RNA, other bipolymers, and combinations thereof. The stabilizing agents adhere to the radical probe without blocking the oxygen active centers. Some preferred stabilizing media include, but are not limted to emulsions containing saturated fatty acids; emulsions containing unsaturated fatty acids; emulsions containing saturated and unsaturated fatty acids; salts of emulsions containing saturated fatty acids; salts of emulsions containing unsaturated fatty acids; salts of emulsions containing saturated and unsaturated fatty acids; diglycerides; triglycerides; bile salts; and combinations thereof.

The suspensions of the present invention may further contain phospholipid, wherein the phospholipid encapsulates the radical probe without blocking the oxygen active centers. The phosholipid may form phospholipid liposomes which encapsulate the radical probe without blocking the oxygen active centers. Some preferred phospholipids include, but are not limited to cholesterol, phosphatidyl choline, phosphatidylethanolamine, phosphatidylserine, cardiolipin, and combinations thereof; and wherein the phospholipid is in the form of unilamellar or multilamellar liposomes or vesicles.

Further provided are noninvasive methods of measuring oxygen concentration, oxygen partial pressure, or oxygen metabolism in a specific tissue or organ in a subject, the method comprising the steps of: (a) administering a lithium phthalocyanine derivative radical probe to the subject; and (b) applying a magnetic resonance (MR) spectroscopy technique capable of measuring O$_2$ concentration in tissues or organs of the subject. Additionally, the probes of the present invention may be used to measure nitric oxide (NO) concentration, separate from or along with oxygen concentration, using the same method.

Preferred lithium phthalocyanine derivative radical probes include, but are not limited to:

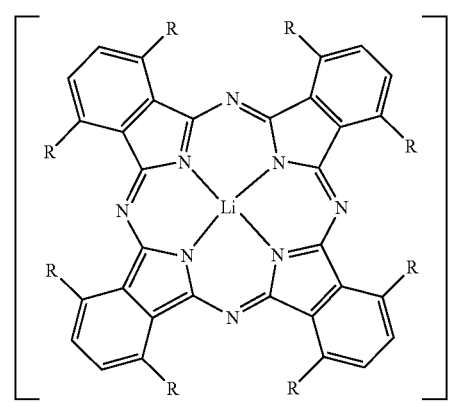

[R1]

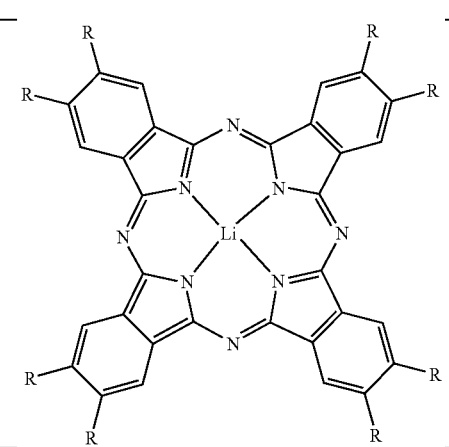

[R2]

-continued

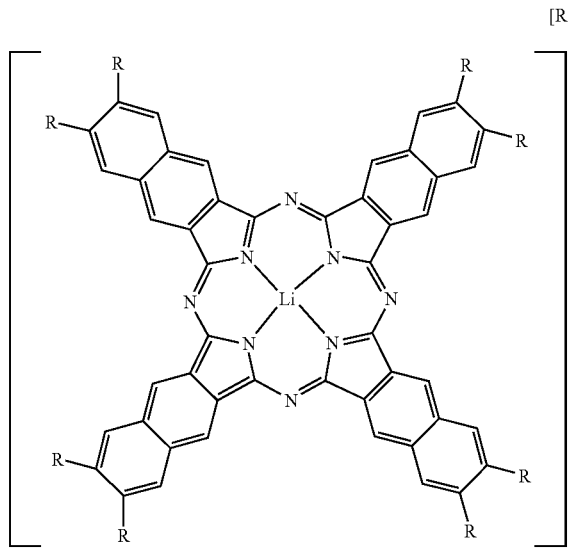
[R3]

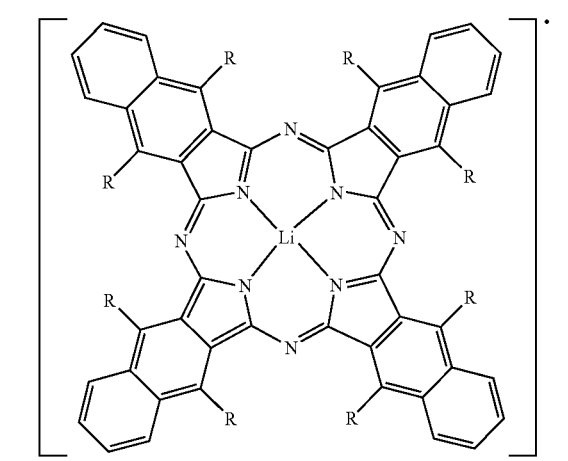
[R4]

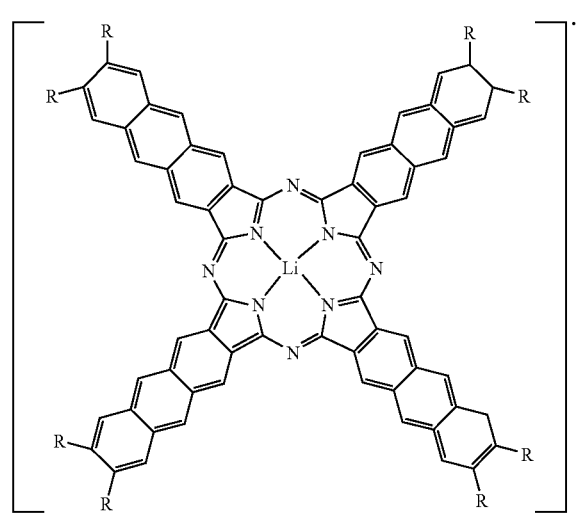
[R5]

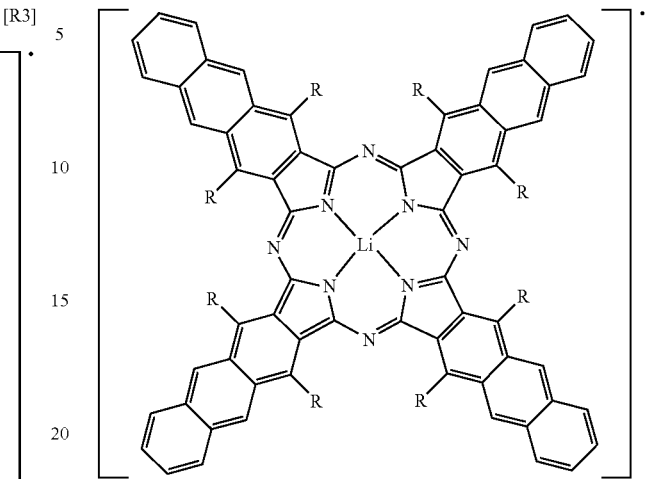
[R6]

wherein R is selected from the group consisting of O(CH$_2$)$_n$CH$_3$, S(CH$_2$)$_n$CH$_3$, O(CH$_2$)$_n$CH$_2$OH, O(CH$_2$)$_n$CH$_2$NH$_2$, O(CH$_2$)$_n$CH$_2$SH, and combinations thereof; wherein n is 1-6; and combinations thereof.

The lithium phthalocyanine derivative radical probes are useful for MR spectroscopy and MR imaging, particularly, but not limited to MRI, ESR, EPR, ERPI, and PEDRI. The probes may be delivered to a subject intravenously or may be implanted into tissue. The probes are useful for studying tissues, organs or cells. When the radical probe is delivered to the subject intravenously, it may be delivered as a suspension or emulsion. The probe may also be delivered directly to the tissue or organ of interest. When injected into the tissue of interest, the radical probes may remain active in a subject for up to 12 months, and preferably remain active for more than 180 days, allowing study of the same tissue or organ over an extended period of time.

The radical probes may be attached to a peptide or glycoconjugate that has specific affinity for cell surface markers, wherein the radical probe acts as a cell migration marker. The radical probes may also to an antibody, wherein the antibody has an affinity to cell surface proteins that lead as markers of cell migration, cell division, and cell death. The radical probes may also be internalized in live cells, either in vivo or in vitro for the study of intracellular oxygenation, cellular hypoxia, cellular hyperoxia, cell division, cellular migration, or metastatis. The radical probes may also be utilized to study the kinetics of enzymes that involve oxygen consumption and release in organs, tissues, or cells, in vivo or in vitro. The subjects may be any subject of interest. Preferably, the subject is a human subject. The methods of the present invention may also be used to study microbial oxygen metabolism.

Figure 2:
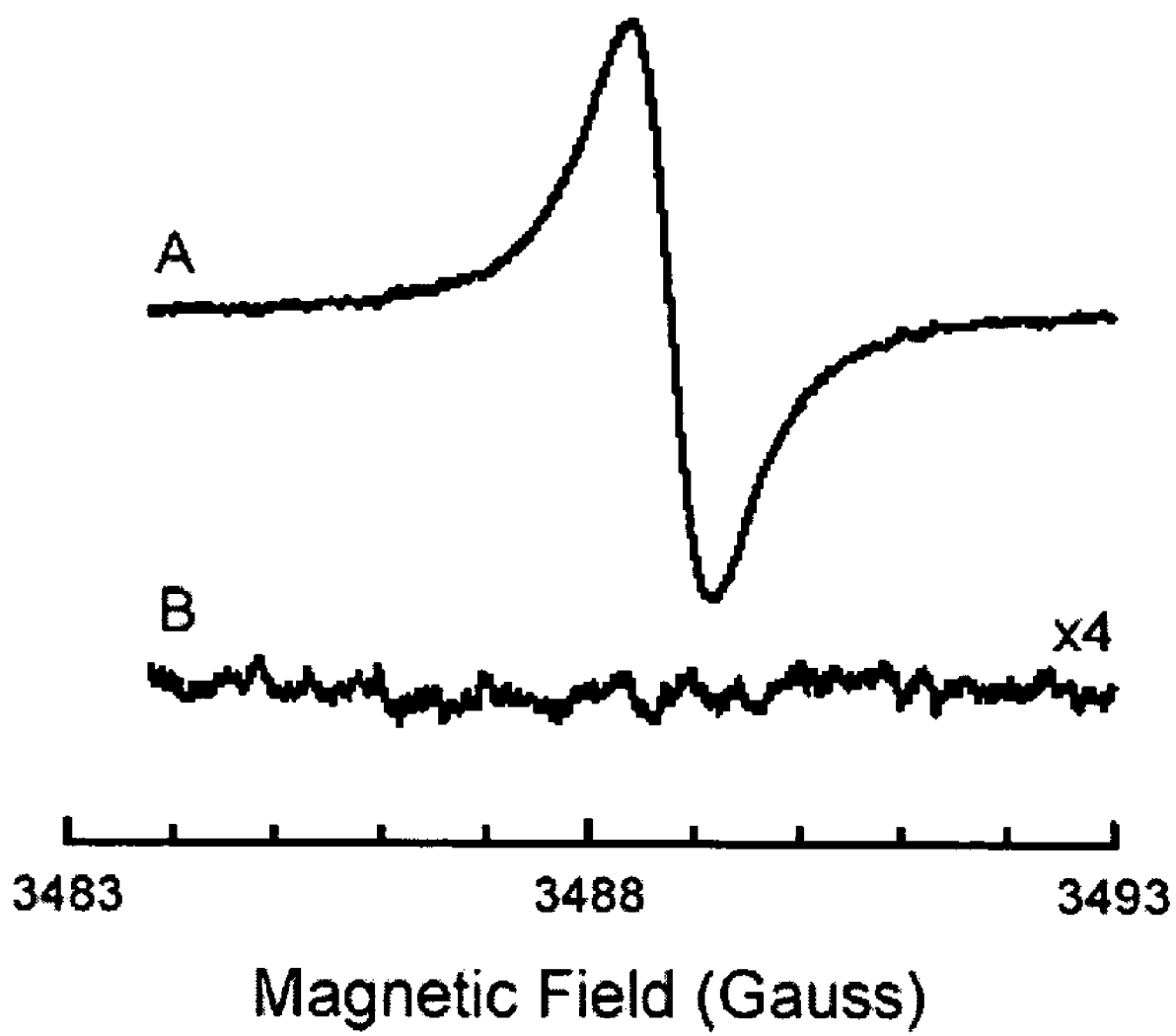
FIG. 2 EPR spectrum of LiNc—BuO nanocrystalline powder suspended in PBS. The spectrum (A) was measured at X-band (9.78 GHz) from a 10 μL of the suspension equilibrated with 10% (PO$_2$: 76 mmHg) oxygen at room temperature. The instrumental settings were: microwave power, 1 mW; modulation amplitude, 63 mG; modulation frequency, 100 kHz; receiver time constant, 82 msec; acquisition time, 60 sec (4×15 sec scans); A single sharp peak is observed with peak-to-peak width ($Ab_{pp}$) of 852 mG. Also superimposed on this spectrum is a computer fit that was calculated assuming Lorentzian line-shape. The difference between the measured spectrum and the Lorentzian fit is shown in (B) at 4× magnification. The difference curve shows only noise suggesting that the line-shape is 100% Lorentzian (R2=0.9999).
Figure 3:
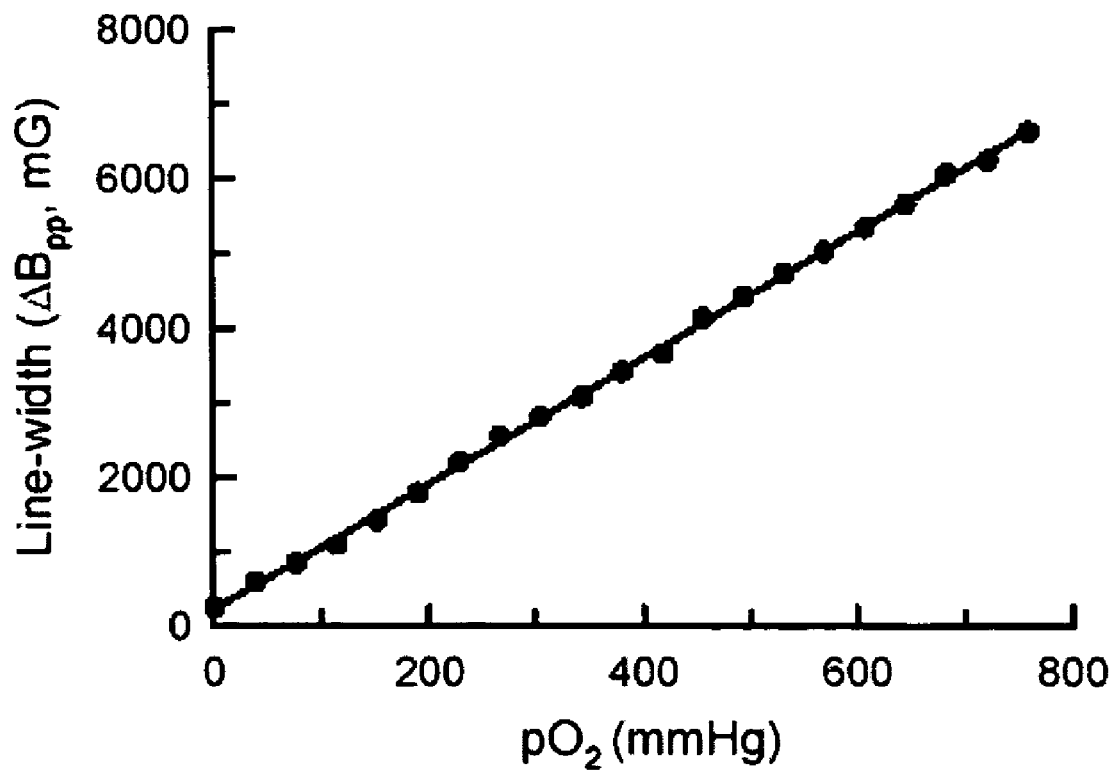

FIG. 3 Effect or oxygen concentration ($pO_2$) on the peak-to-peak EPR line-width ($AB_{pp}$) of LiNc—BuO particulates. The particulates were suspended in PBS equilibrated with mixtures of oxygen/nitrogen gases. The spectra were acquired as described in FIG. 2. The line-width increases linearly with $pO_2$ in the range 0 to 760 mmHg (corresponding to 0-100% oxygen at 1 atmospheric pressure) with an anoxic at 0% oxygen) line-width of 210 mG and slope (oxygen sensitivity) of 8 50 mG/mmHg. The effect or oxygen on the line-width was highly reversible and reproducible under a variety of conditions.

Figure 4:
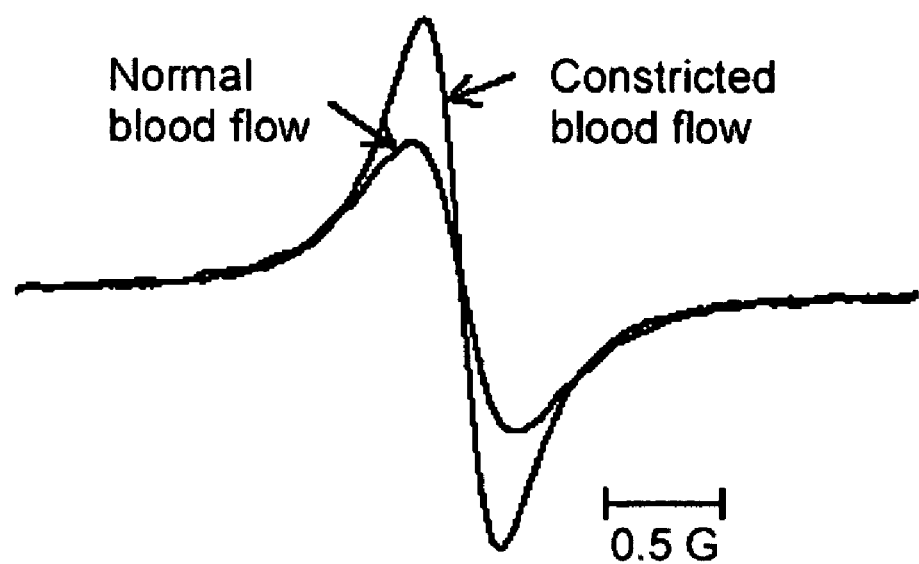
Figure 4:
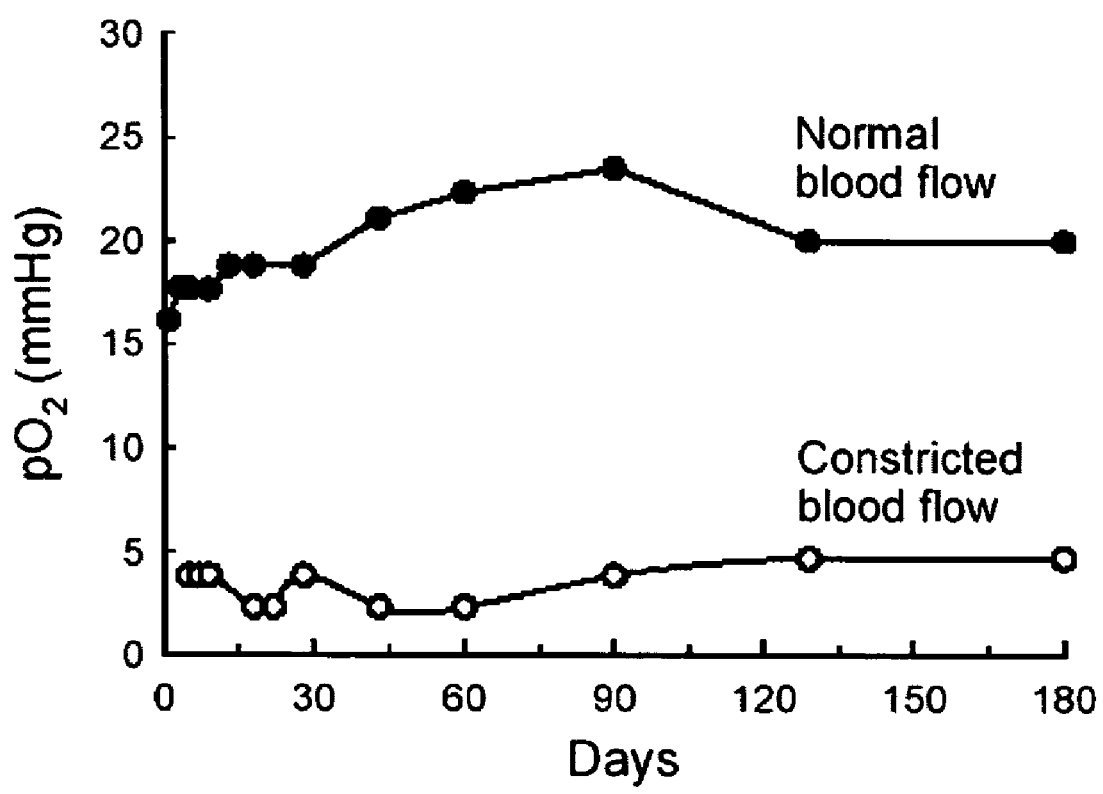

FIG. 4 Long-term stability and response to oxygen, in vivo. The stability of LiNc—BuO particulates implanted in the gastrocnemius muscle (upper hind leg) of C3H mice was studied up to 180 days. The plot shows repeated measurements of $pO_2$ from a single mouse. The response of particulates to oxygen was checked by temporarily constricting blood-flow to the leg. The data show that the particulates are stable and responsive in the live tissues up to 6 months. The spectra shown above were from a mouse on day 180 after implantation of the particulate. The spectra were acquired as described in FIG. 2.

Figure 5:
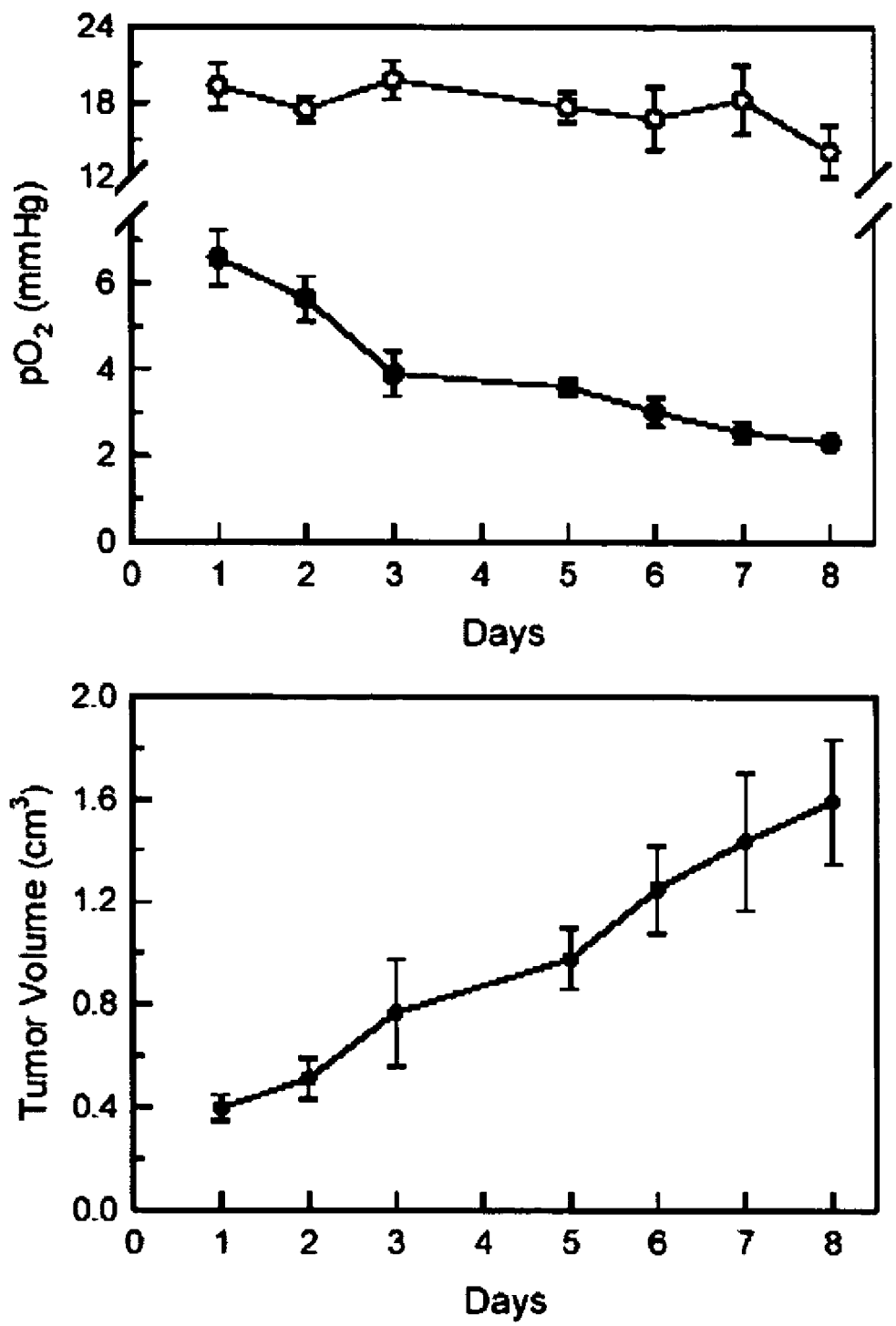

FIG. 5 In vivo measurements of $pO_2$ from tumor and normal gastrocnemius muscle tissues in mice as a function of tumor growth in mice with RIF-1 tumor. LiNc—BuO particulates were unplanned in the tumor (RIF-1) on right leg and normal muscle on left leg and the tissue. $pO_2$ values wire repeatedly measured on the same animals up to 8 days after implantation of the particulates. Mean values of $pO_2$ (A) and tumor volume (B) recorded repetitively from 7 mice are shown. The tumor $pO_2$ decreased continuously to ~2 mmHg on day 8 after implantation, while the normal muscle $pO_2$ remained almost constant (17.6±2 5 mmHg) during the same period.

Figure 6:

FIG. 6 Internalization of the LiNc—BuO particulates in cells. The particulates (<2 μm) were coincubated with the human arterial smooth muscle cells for 72 h followed by repeated washings as described in the Detailed Description of the Invention. The cells were photographed under an inverted microscope while still adherent to the substratum of the 35 mm dish. The LiNc—BuO particulates are seen as dark green crystals inside cells.

Figure 7:
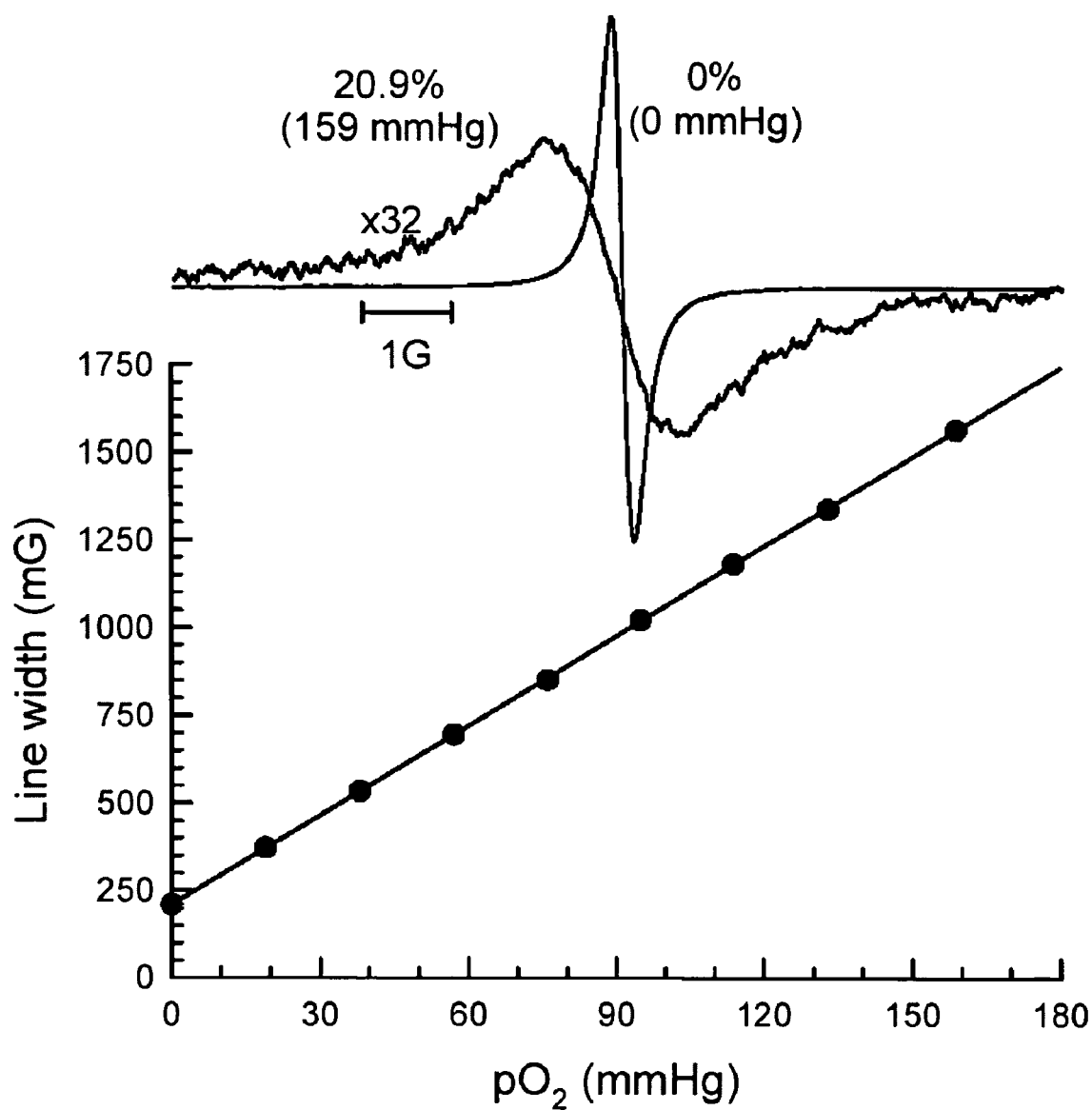

FIG. 7 EPR spectra of LiNc—BuO microcrystalline powder suspended in saline at various partial pressures of molecular oxygen. The spectra were measured at X-band (9.78 GHlz) from a 20 μL of the suspension equilibrated with 0% ($pO_2$: 0 mmHg) and 20.9% ($pO_2$: 159 mmHg) oxygen at room temperature. The instrumental settings were: microwave power, 1 mW, modulation amplitude, 63 mG, modulation frequency 100 kHz, receiver time constant 82 msec; acquisition time 60 sec (4×15 sec scans). A single sharp peak is observed with a peak-to-peak width ($\Delta B_{pp}$) of 210 mG at 0% oxygen and 1550 mG at 20.9% oxygen.

Figure 8:
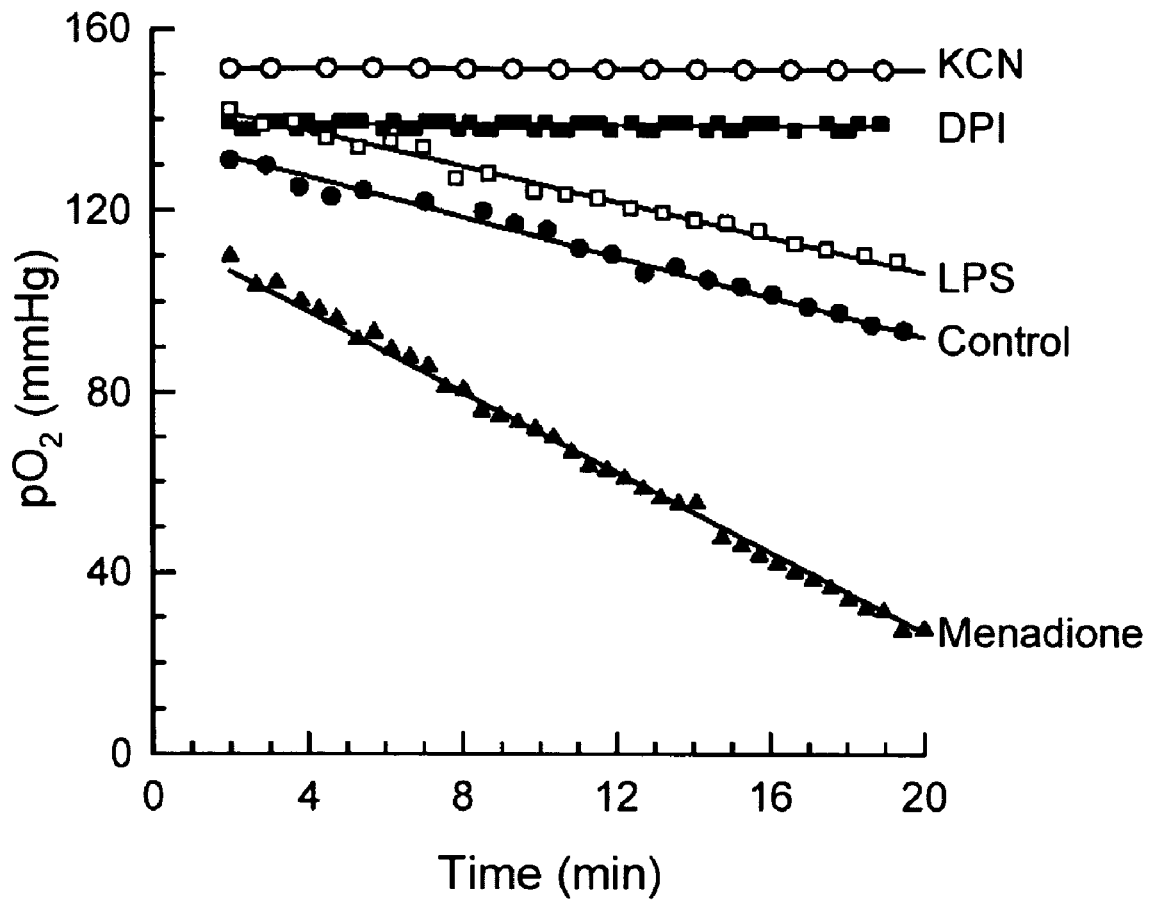

FIG. 8 Time dependence of $pO_2$ in mouse aortic endothelial cell suspensions exposed to various agents and treatments. The $pO_2$ measurements were performed on 20,000 cells taken in a 20 μL capillary tube (id: x μm; cell density: 1×10$^6$ cells mL) by EPR spectroscopy utilizing LiNc—BuO oximetry probe. The capillary tube was sealed at both ends and $PO_2$ measurements were performed continuously for up to 20 min. (a) Control (b) KCN (100 μM), (c) rotenone (100 μM), (d) DPI (100 μM), (e) menadione (50 μM), (f) LPS (10 μg/ml). Values at each time point are expressed as mean±SD of 4-5 independent experiments. The solid lines through each data set show the linear variation of $pO_2$, which suggests constancy in oxygen consumption as a function of time.

Figure 9:
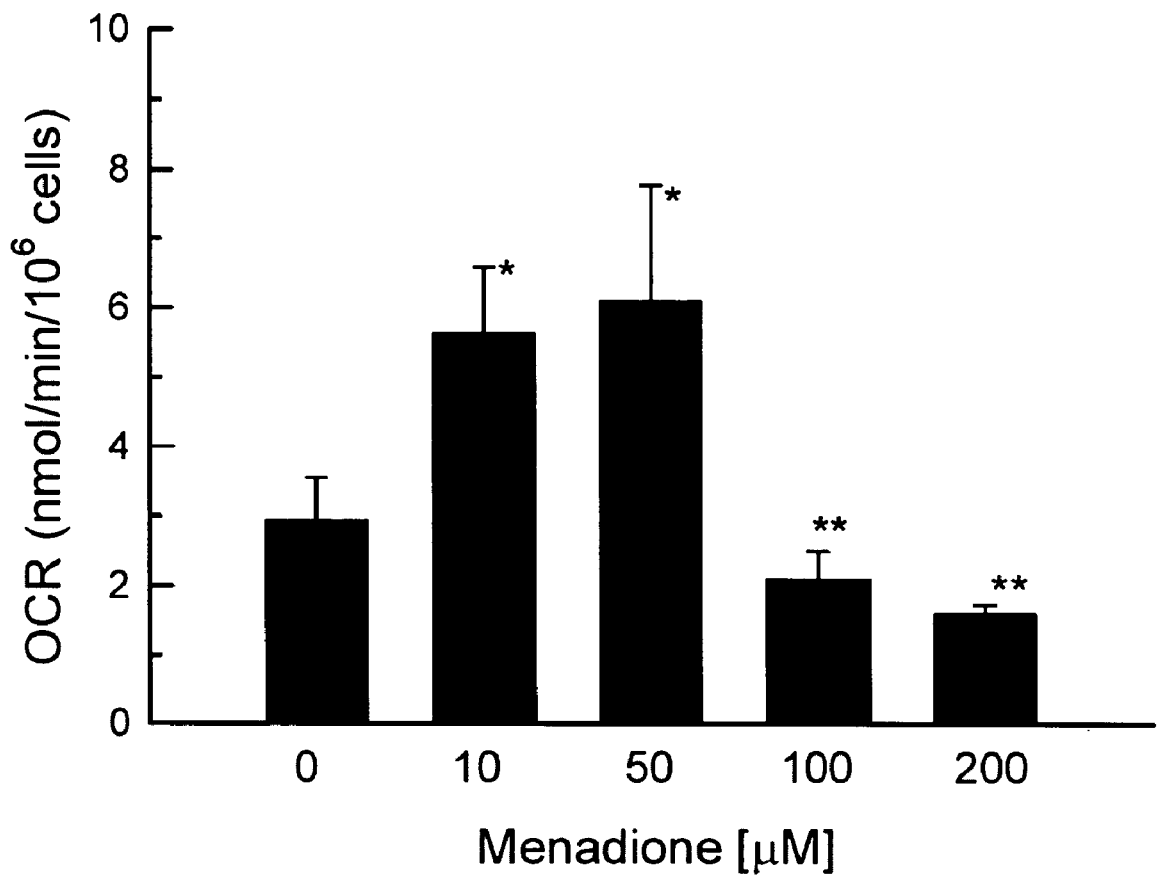

FIG. 9 Effect of menadione on the rate of oxygen consumption by mouse aortic endothelial cells. The measurements were performed as described in the Detailed Description and oxygen consumption rates are calculated from the slope of change of $pO_2$ with time. Cells were treated with 10, 50, 100 and 200 μM concentration of menadione and the measurements were started immediately after adding menadione. Values are +SD of 5 experiments. *p<0.001 versus control; **p<0.01 versus control.

Figure 10:
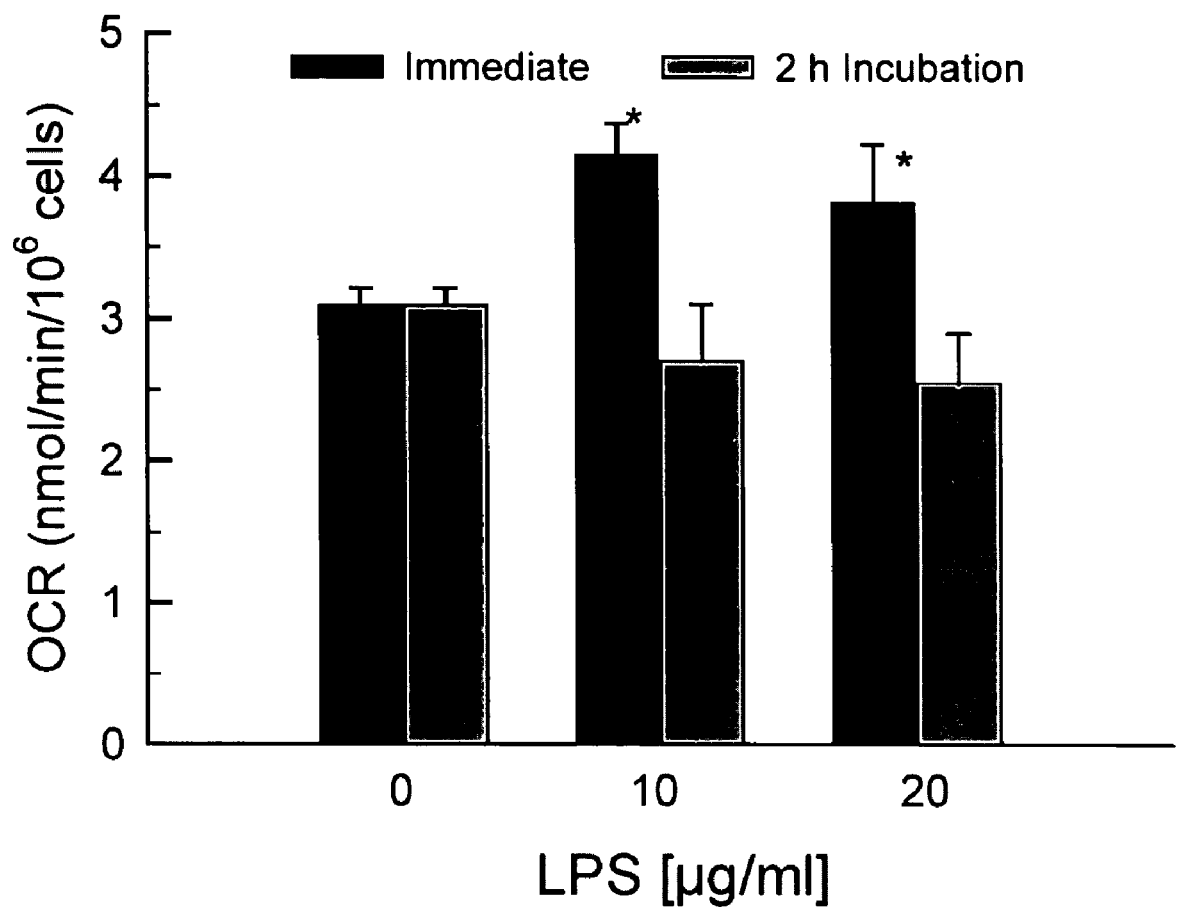

FIG. 10 Effect of lipopolysaccharide (LPS) on the rate of oxygen consumption by MAECs. The measurements were performed as in FIG. 2 and oxygen consumption rates were calculated from the slope of change of $pO_2$ with time. Cells (1×10$^6$ Cells/ml) were treated with 10 or 20 μg/ml concentration of LPS and measured either immediately after mixing or after 2 h or incubation of the mixture under aerobic conditions. Values are mean±SD of 5 experiments. *p<0.05 versus control.

Figure 11:
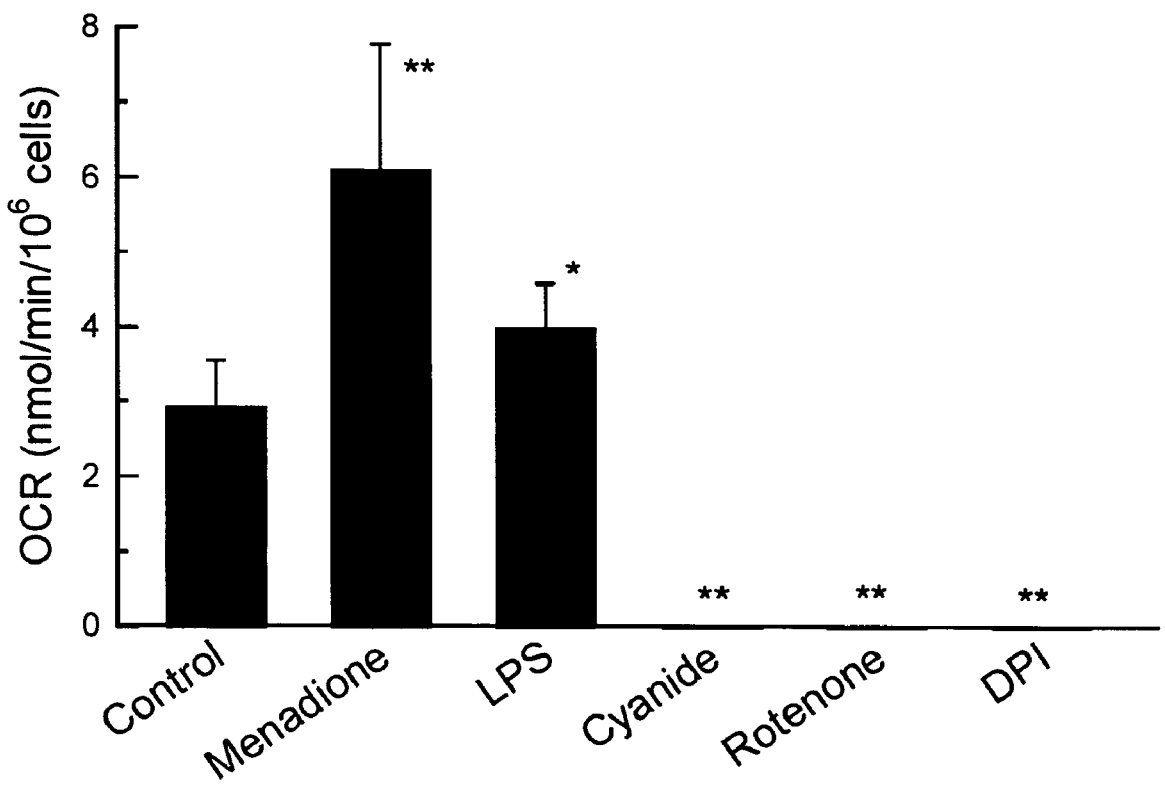

FIG. 11 Oxygen consumption rates in mouse aortic endothelial cell suspensions exposed to various agents and treatments. Cells (1×10$^6$ Cells/ml) were treated with menadione (50 μM), LPS (10 μg/ml), KCN (100 μM), rotenone (100 μM) and DPI treatment. Values are mean±SD of 5 experiments. * p<0.001 versus control; ** p<0.01 versus control.

Figure 12:
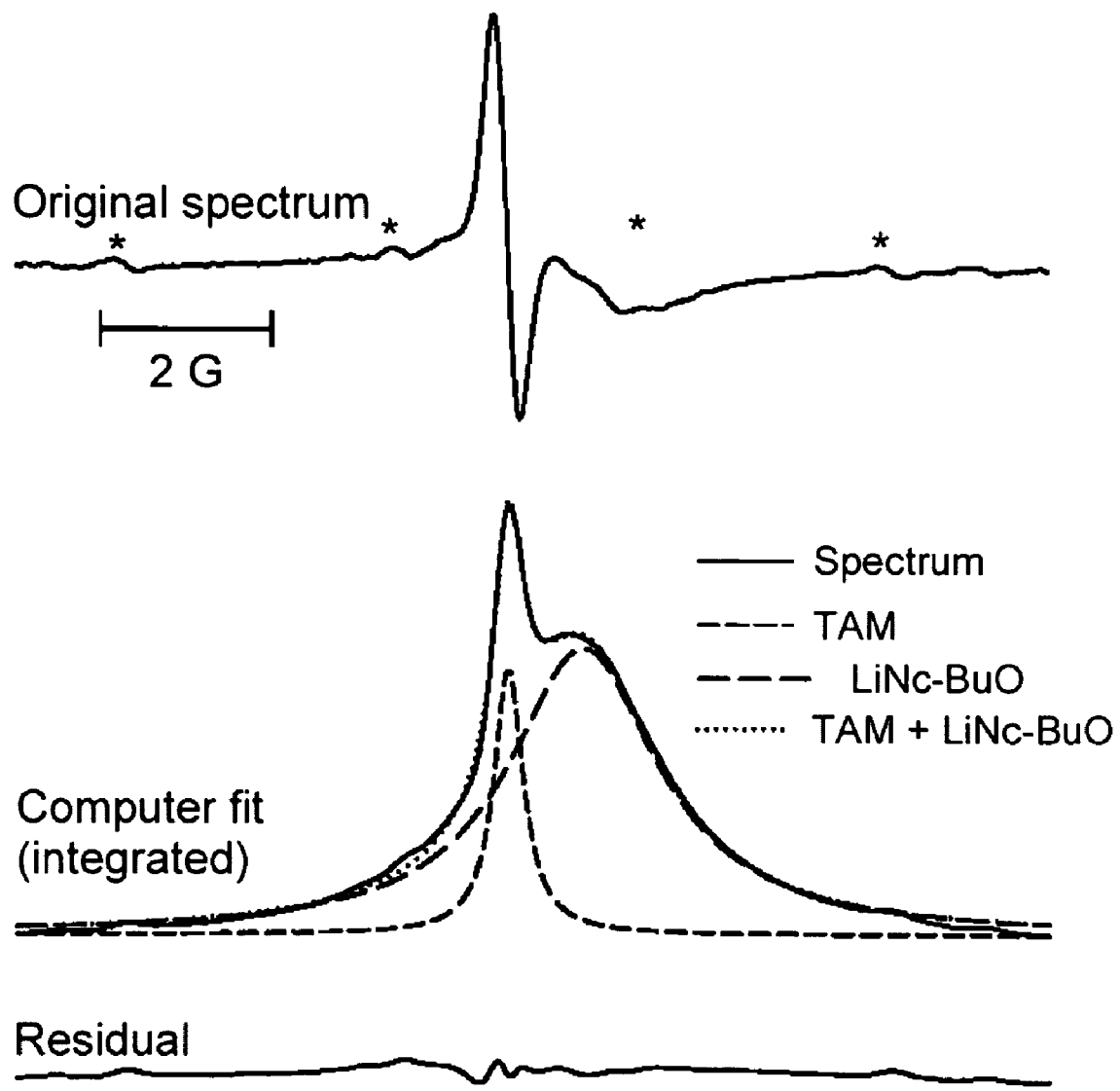

FIG. 12 EPR spectrum of a suspension of LiNc—BuO and TAM (10 μM) in PBS (pH 7.4) equilibrated with room air (20.9% oxygen). The original spectrum (top) is a composite of two components: a sharp peak from TAM (g+2.0030) and a broad peak from KiNc—BuO (g+2.0024). The additional peaks indicated by * on both sides of the spectrum are due to 13C hyperfine from TAM (35). EPR data acquisition parameters were: modulation amplitude, 100 mG; microwave power 1 mW; time constant, 8-msec, scan time, 15 s. The computer fit (middle) shows the decomposition of the original spectrum into two components, that the LiNc—BuO and TAM. The computer fit (sum of the two components, that the LiNC-BuO and TAM. The computer fit (sum of the two components) is superimposed onto the original spectrum. The residual (bottom) curve shows the difference between the original and computer fit ($R^2$=0.9977).

Figure 13:
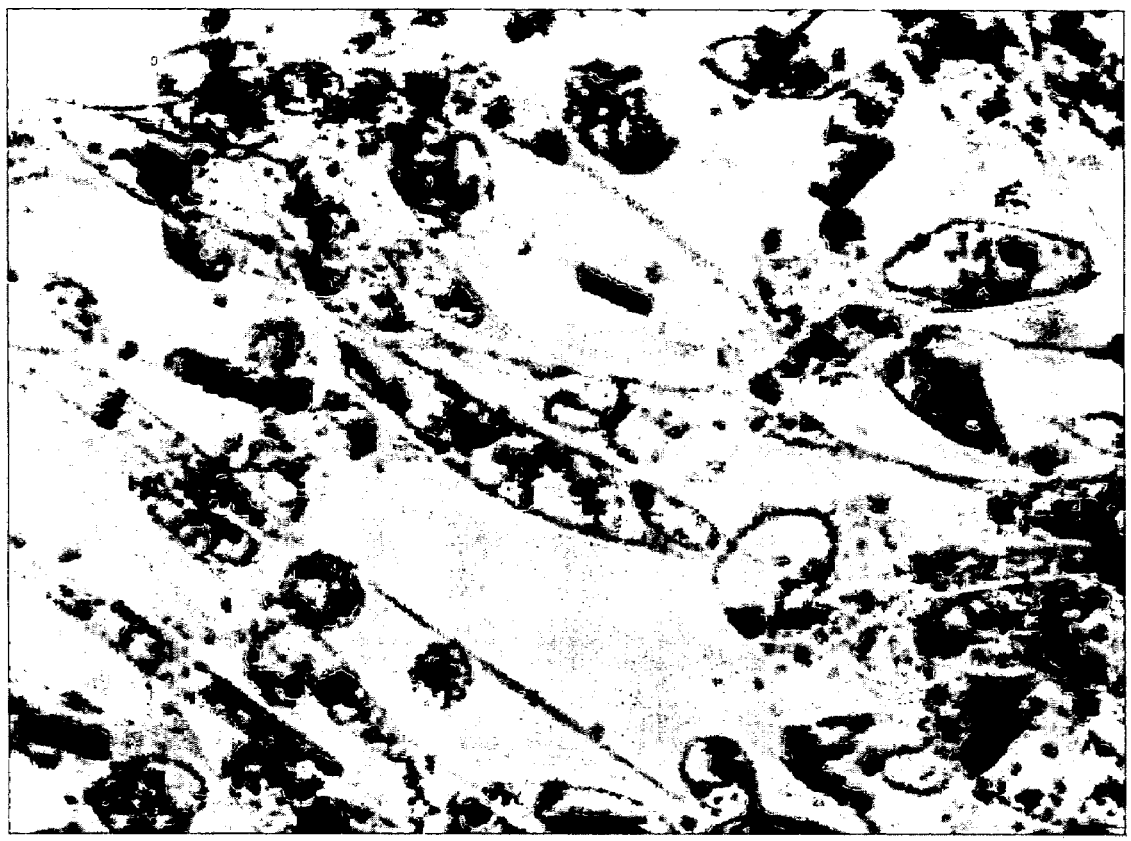

FIG. 13 Photomicrograph of bovine lung microvascular endothelial cells showing internalization of the LiNc—BuO microparticulates. The LiNc—BuO particulates are seen as dark green crystals inside the cells.

Figure 1:
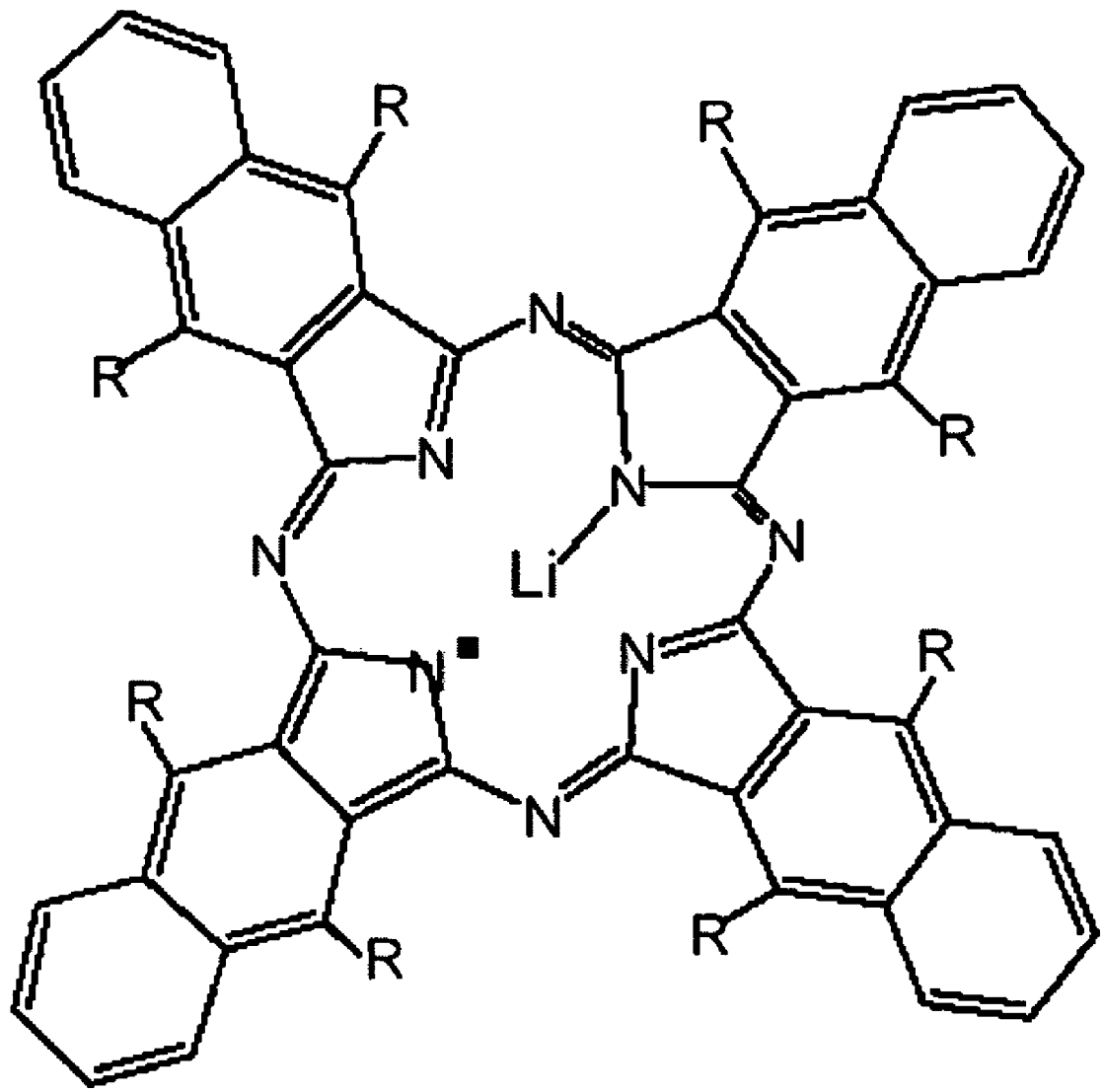
FIG. 1 Molecular structure of lithium octa-n-butoxy-naphthalocyanine (LiNc—BuO) radical. The neutral radical is paramagnetic and prepared as a microcrystalline solid.
Figure 14:
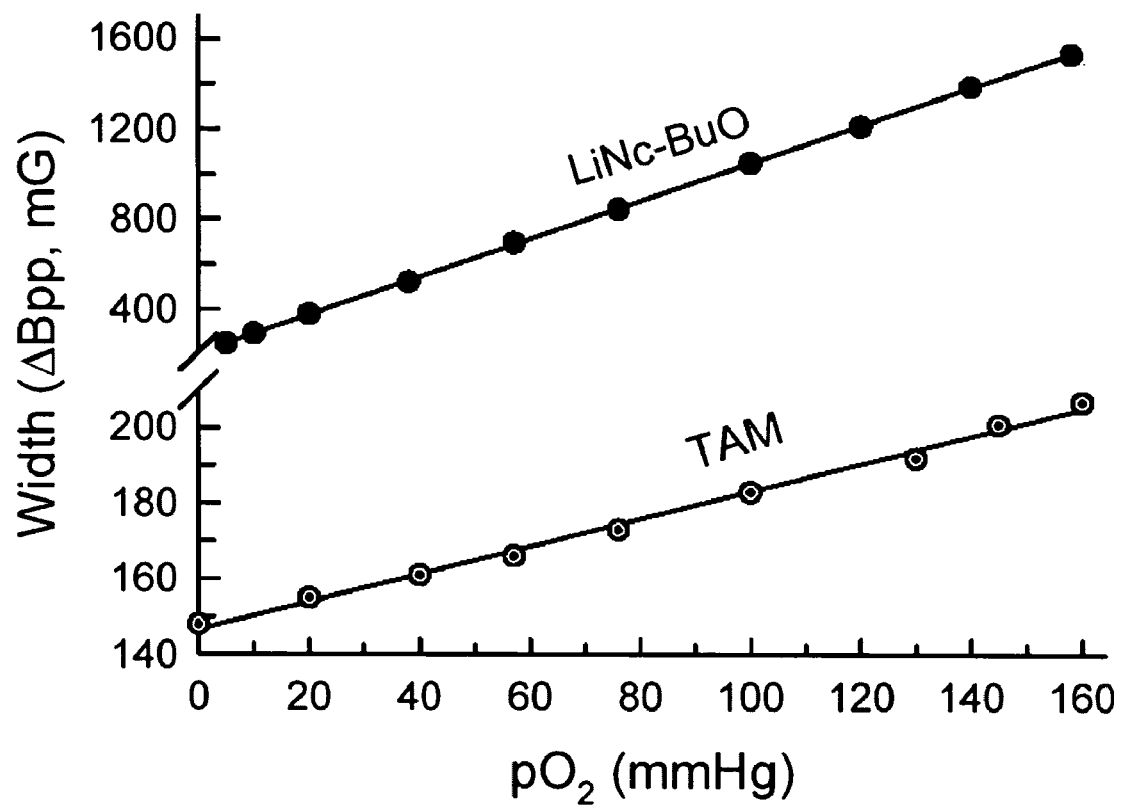

FIG. 14 Effect of oxygen concentration ($pO_2$) on the peak-to-peak EPR line-width ($\Delta B_{pp}$) of LiNc—BuO and TAM. Measurements were made independently of LiNc—BuO microcrystalline particulates suspended in saline and TAM (10 μM) in PBS equilibrated with mixtures of oxygen/nitrogen gases. The spectra were acquired as describe din FIG. 1. The line-width increases linearity of $pO_2$ in the range of 0 to 160 mmHg) with an anoxic (0% oxygen) line-width of 210 mG and slope (sensitivity) of 8.5 mG/mmHg for LiNc—BuO and an anoxic line-width of 148 mG and slope (sensitivity) of 0.36 mG/mmHg for TAM.

Figure 15:
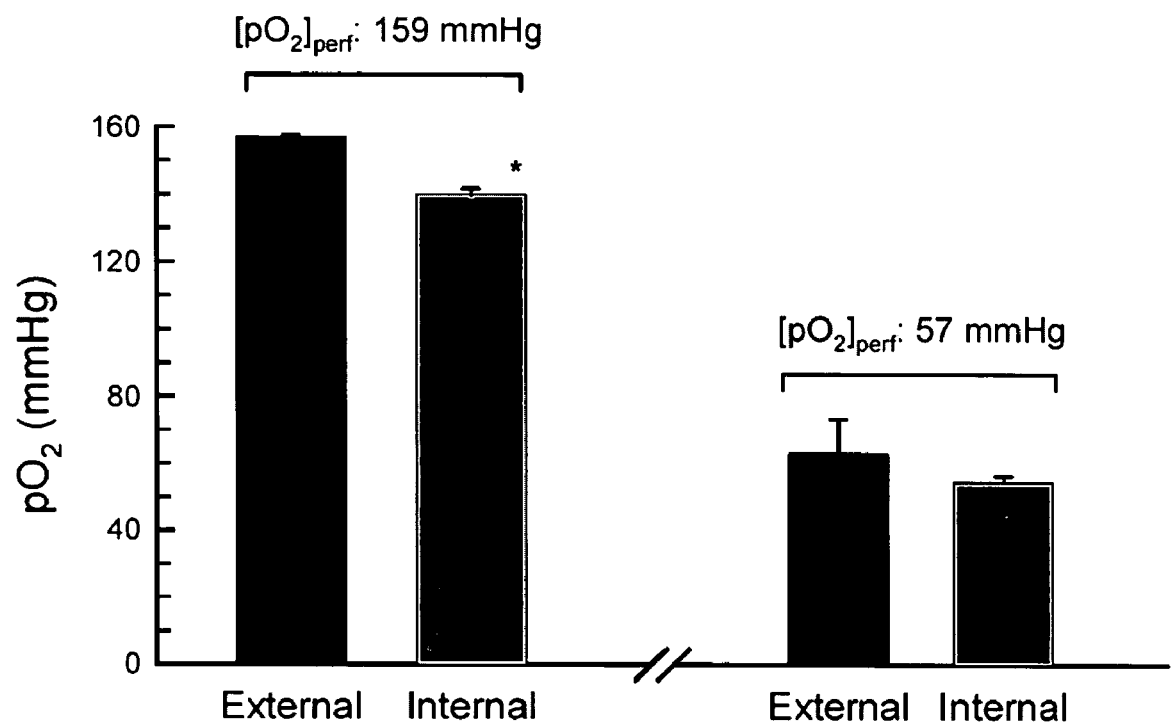

FIG. 15 Extracellular and intracellular measurement of $pO_2$ in bovine lunch microvascular endothelial cells (BLM-VECs). Intracellular $pO_2$ was measured using internalized LiNC-BuO particulated in BLMECs. The extracellular $pO_2$ was measured simultaneously using 10 μM TAM. Measurements were made at room air (20.9% or $pO_2$: 159 mmHG) and at 7.5% ($pO_2$: 57 mmHG) oxygen. Values are mean±SD of 5 experiments. * $p<0.001$ versus extracellular $pO_2$.

Figure 16:
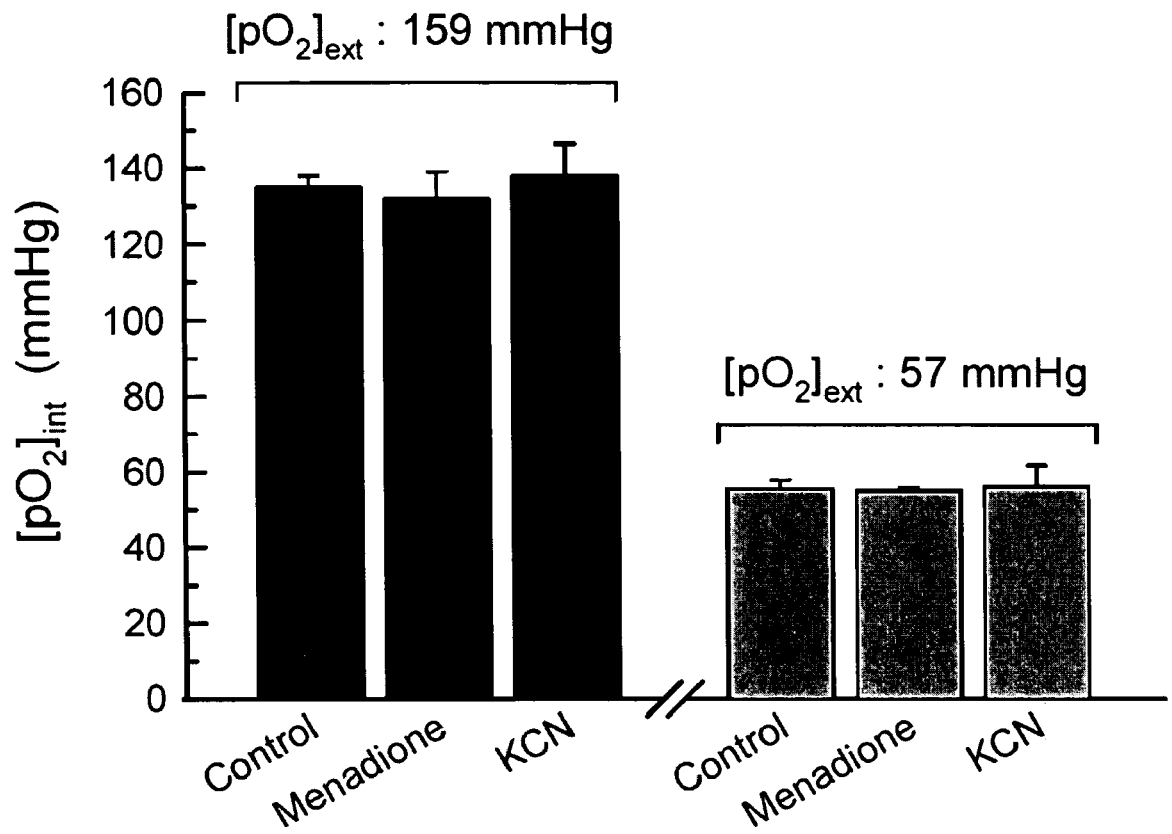

FIG. 16 Effect of menadione and cyanide on intracellular and extracellular $pO_2$ in BLMVECs. The $pO_2$ measurements were made in cells treated with menadione (50 μM) and potassium cyanide (100 μM). The measurements were performed as in FIG. 4. Values are mean±SD of 5 experiments.

Figure 17:
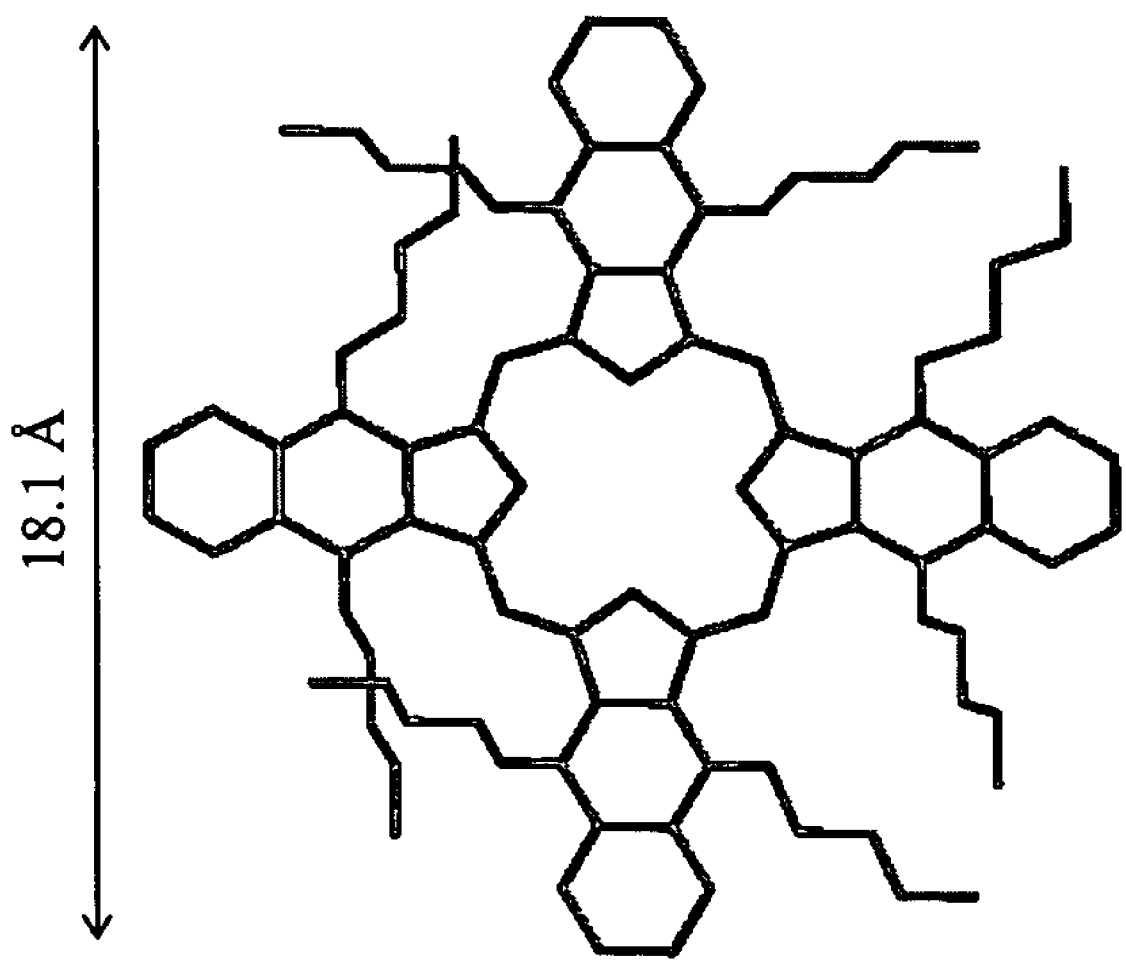

FIG. 17 Simplified molecular structure of Li(OBu)$_8$Nc used for the DASH analysis. Eighty eight hydrogens and one lithium were removed from the original molecule. The side lengths of the naphthalocyanine rings are 17.9~18.0 Å in NiNc, CuNc, and ZnNc.

Figure 18:
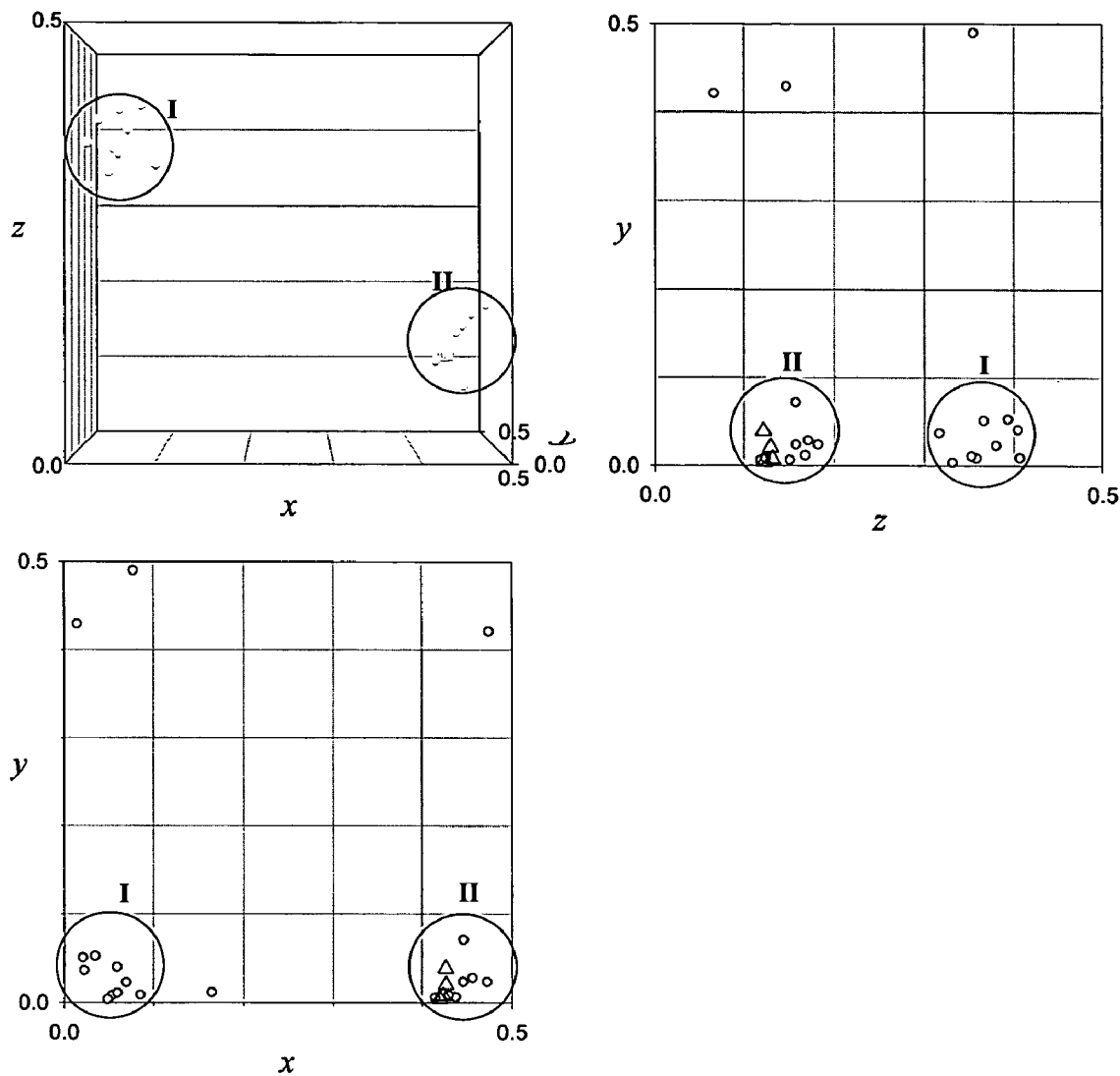

FIG. 18 Positional parameters obtained from initial DASH trial runs where no constraints were used. Black open circles are from trials using Li(OBu)$_8$Nc (20 results with lowest $\chi_{pro}^2$, out of 45 trials) and open triangles are form the trials using Li(OH)$_8$Nc (reproducibility, 10/10), Li(OMe)$_8$Nc (8/10), Li(OEt)$_8$Nc (9/10), and Li(OPr)$_8$Nc (6/10). For the groups marked as I and II, average and deviations of the coordinates are (0.051±0.021, 0.026±0.019, 0.368±0.031) and (0.443±0.019, 0.024±0.023, 0.151±0.023), respectively.

Figure 19:
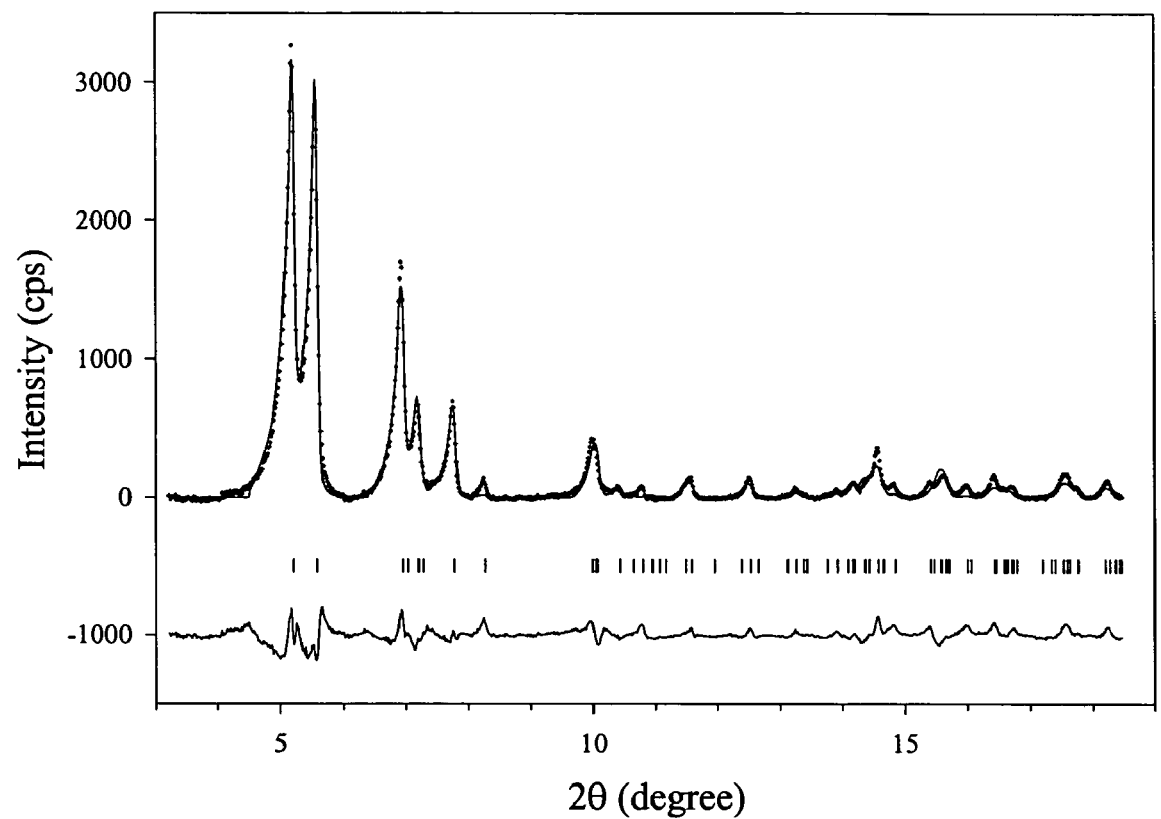

FIG. 19 Simulated annealing refinement profile of the XRPD patter for .Li(OBu)$_8$Nc. Calculated (solid line) and observed (cross) data are overlapped. Bragg reflection positions and the difference pattern are shown below.

Figure 20:
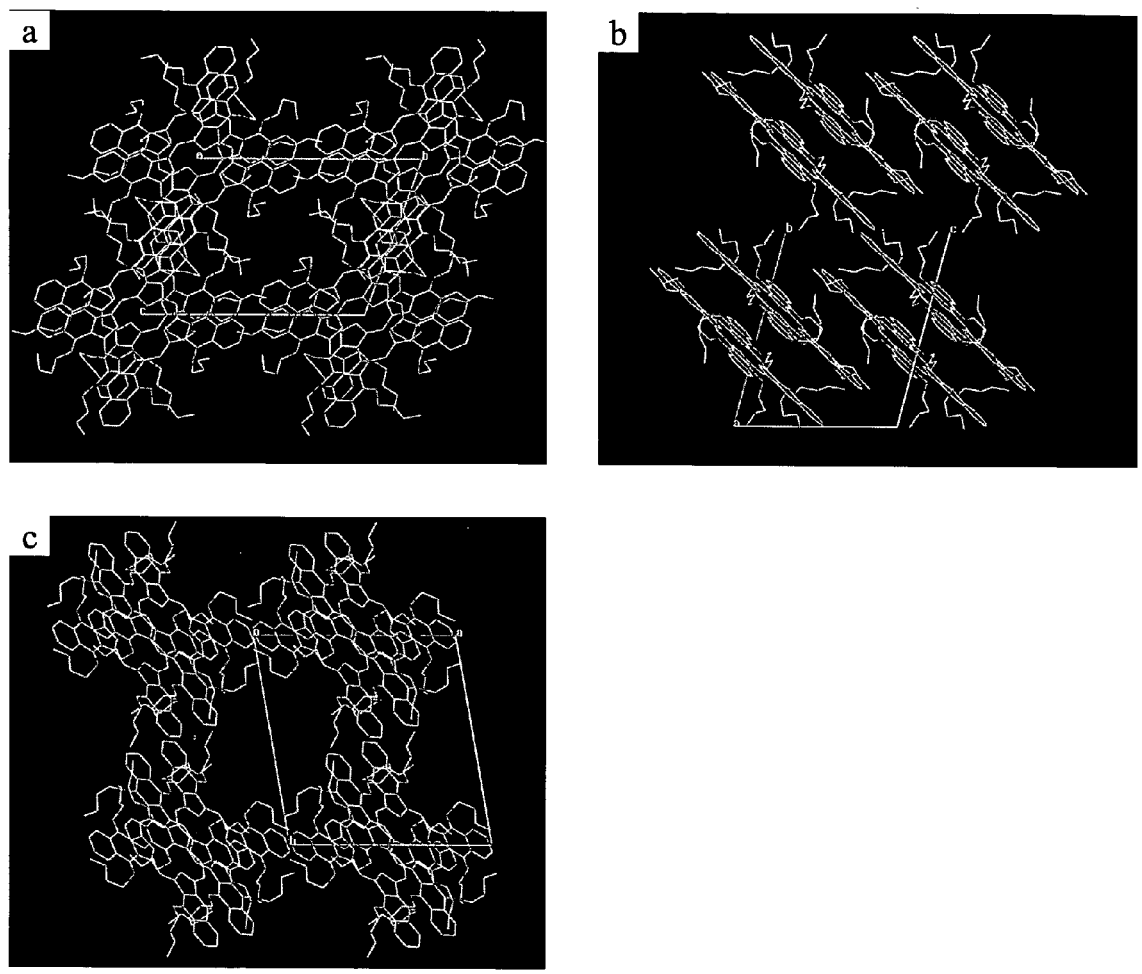

FIG. 20 Stacking patter of Li(OBu)$_8$Nc as determined from the DASH analysis, viewed along (a) a-, (b) b-, and (c) c-axes. The rectangles represent the cross sections of infinite channels propagating in the viewing direction (their sizes are mentioned in text).

Figure 21:
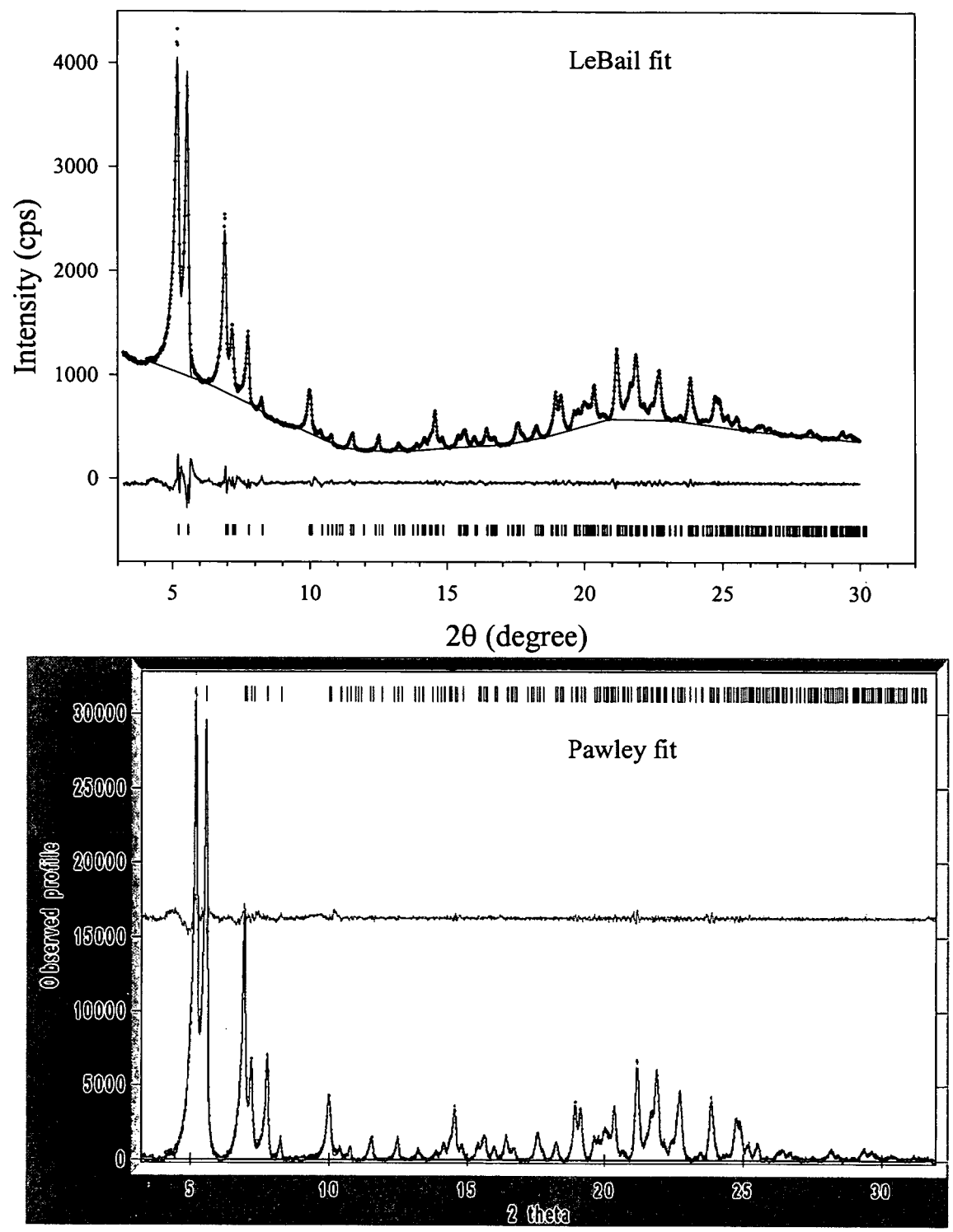

FIG. 21 (Top) LeBail and (bottom) Pawley fits to the XRPD pattern of Li(BuO)$_8$Nc. Observed (cross) and calculated data (solid line) are overlapped, and the difference pattern and expected peak positions are shown. In the LeBail fit, background is also shown.

Figure 22:
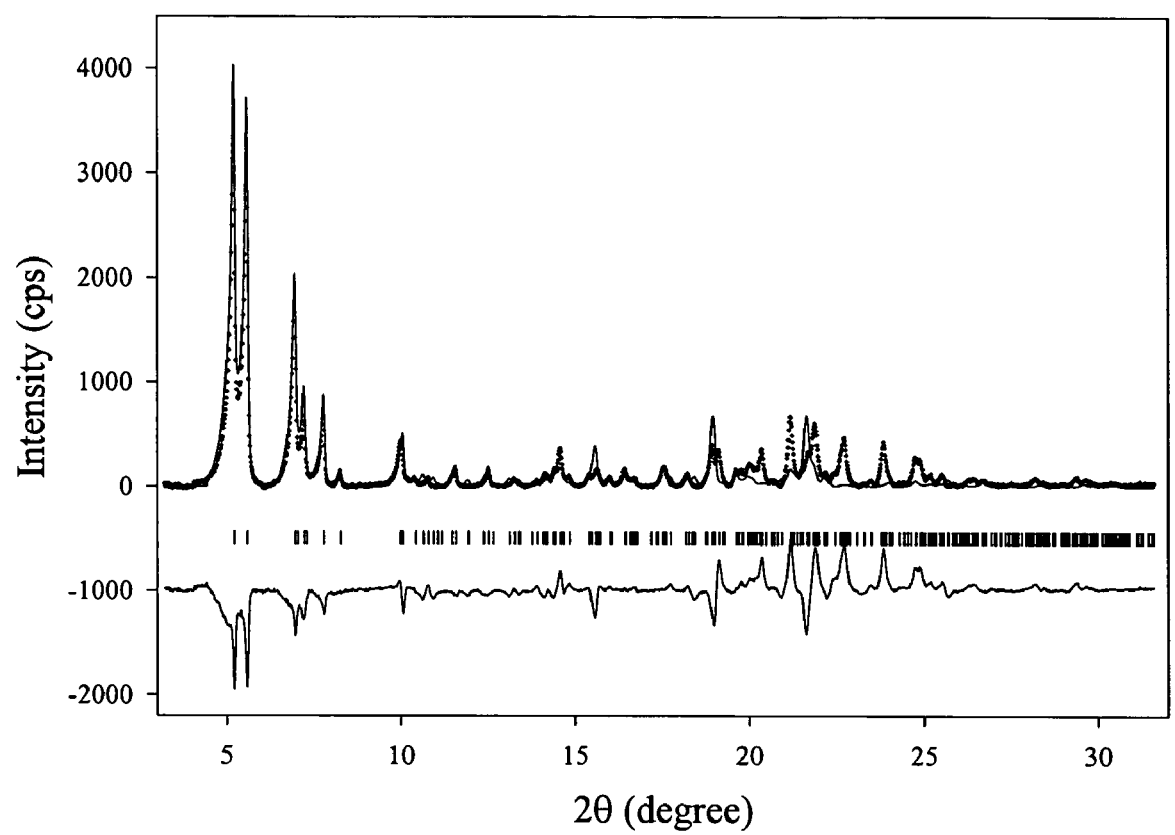

FIG. 22 Simulated annealing refinement profile of the XRPD pattern for Li(OBu)$_8$Nc, between 3.2-32°. Calculated (solid line) and observed (cross) data are overlapped. Bragg reflection positions and the difference pattern are shown below.

DETAILED DESCRIPTION OF THE INVENTION

NMR-based magnetic resonance imaging, MRI, enables visualization of the distribution of nuclear spins, mostly protons, in tissues. It has become a 'gold standard' for noninvasive diagnosis of tissue abnormalities. Electron paramagnetic resonance imaging (EPRI) is a parallel technology, which enables visualization of the distribution of electron spins (free radicals) in tissues. EPR is inherently about 3 orders of magnitude more sensitive than NMR. It can directly detect and image relatively stable free radicals as well as labile radicals such as oxygen-derived superoxide and hydroxyl free radicals that are implicated in the pathogenesis of oxidant injury [14-21]. Recently, EPR methods have also been developed to enable detection of nitric oxide [22-24]. In addition, spin probes may be used to image cellular radical metabolism and redox state, membrane structure and fluidity, oxygen, pH, temperature, protein structure, and cell death. With spin labeling of molecules and cells, noninvasive mapping of their localization in tissues may be performed [8, 9, 12, 25-34].

Recent advances in magnetic resonance instrumentation and probe design have enabled integration of these two modalities into a new technology, proton electron double resonance imaging (PEDRI) which is capable of co-imaging free radicals and protons [4, 7, 35].

A major power of EPR technology is its ability to precisely measure $O_2$ in tissues [6, 9, 31, 36-40]. This 'EPR oximetry' technique uses spin probes whose EPR line-widths are highly sensitive to $O_2$ concentration. It enables precise and accurate measurements of $O_2$ concentrations in tissues, noninvasively and repeatedly over periods of weeks from the same site. This approach uses fine crystals (nanoprobes) of phthalocyanine-based radical molecules that are stacked producing a very strongly exchanged-narrowed EPR line-shape, that is highly sensitive to local $O_2$ concentration [9, 40, 41]. These nanoprobes are biocompatible and stable in tissues. They may be implanted at the desired site or with a suitable coating may be infused into the vasculature for targeted delivery to tissues. In addition, we recently demonstrated that these nanoprobes may be internalized in cells enabling measurement of intracellular $pO_2$ with milliTorr accuracy.

Cellular redox measurements are performed using redox-sensitive nitroxyl molecules that are soluble spin probes [36]. A variety of nitroxyl molecules capable of reporting cellular redox levels including total redox, thiols, and glutathione may be used. These molecules are nontoxic and are converted to nonradical species and cleared from the system within hours after infusion.

Overall, the novel in vivo MR techniques of EPRI and PEDRI can provide important information about tissue radical generation, oxygenation, nitric oxide production, metabolism and injury as well as therapeutic delivery. With the recognized importance of free radicals, oxygen and NO in disease this information is of crucial importance. These techniques also can enable high sensitivity measurement of molecular expression, gene expression, cell therapy and the delivery of a broad range of molecular therapeutics. These major advances in molecular and genetic imaging have the potential to revolutionize medical diagnosis and treatment.

Abbreviations The following abbreviations are used herein: AAPH—2,2'-azobis(2-amindinopropane)dihydrochloride; CRISP—Crystalline internal spin probe; DMEM—Dulbecco's modified Eagle medium; EPR—Electron paramagnetic resonance; FBS—Fetal bovine serum; HASMC—Human arterial smooth muscle cells; LiNc—Lithium naphthalocyanine; LiNc—BuO—Lithium 5,9,14,18,23,27,32,36-octa-n-butoxy-2,3-naphthalocyanine; LiPc—Lithium phthalocyanine; MEM—Minimal essential medium; Nc—BuO -5,9,14,18,23,27,32,36-octa-n-butoxy-2,3-naphthalocyanine; PBS —Phosphate-buffered saline; $pO_2$—Partial pressure of oxygen; RIF-1-Radiation-induced fibrosarcoma-1; SNAP —S-nitroso-N-acetyl-penicillamine; and TAM—Triarylmethyl.

The probes of the present invention are lithium phthalocyanine derivatives. As used throughout the specification and claims, "lithium phthalocyanine derivatives" includes, but is not limited to lithium phthalocyanine derivatives and radicals thereof; lithium naphthalocyanine derivatives and radicals thereof; and lithium anthraphthalocyanine derivatives and radicals thereof. The probes of the present invention are designed or targeted to visualize specific molecular targets. These probes may also be tagged to proteins or DNA enabling generalized biomolecular and gene imaging. The probes may be implanted at a desired site or coated with a suitable coating formulation may be infused into the vasculature for targeted delivery to tissues to facilitate study of a tissue of interest. The probes of the present invention may also encapsulated in phospholipid liposomes (e.g. phosphatidylcholine and cholesterol) to facilitate rapid uptake into the cells, which are delivered into cells engineered for tissue or wound repair.

The lithium phthalocyanine derivatives are particulate, and have low solubility in aqueous solutions as well as in common organic solvents, making them particularly suitable for the following applications: (i) as an oxygen-sensing EPR probe for accurate determination of concentration of oxygen and (ii) as a molecular and cellular imaging probe for EPR/MRI methods. The probes also have applications in the field of biomedical research and clinical studies, including, but not limited to: (1) determination of oxygen concentration in tissues; (2) determination of oxygen concentration in cells; (3) determination of oxygen consumption by cells; (4) targeted intracellular delivery of particulate oximetry probes; and (5) DNA or protein-targeted spin probes. Additional applications of the nanoparticulate probes of the present invention include cell-tagging and cell-tracking applications; studying cancer metastasis in experimental models; tissue engineering (stem cell research); tagging antibody; MRI contrast agent; implantable oxygen-sensor in peripheral vascular disease; oxygen-sensor in wound healing applications; and implantable oxygen-sensor in cancer therapy.

Synthesis of micro and nanoparticulate oximetry spin probes based on phthalocyanine macrocycles Mono-lithiated phthalocyanine and naphthalocyanine derivatives are synthesized using chemical or electrochemical procedures as we reported previously [11, 42]. The synthesis is set forth in the following synthetic schemes:

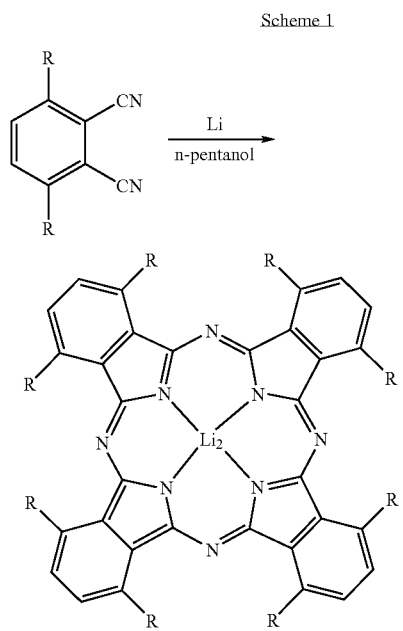

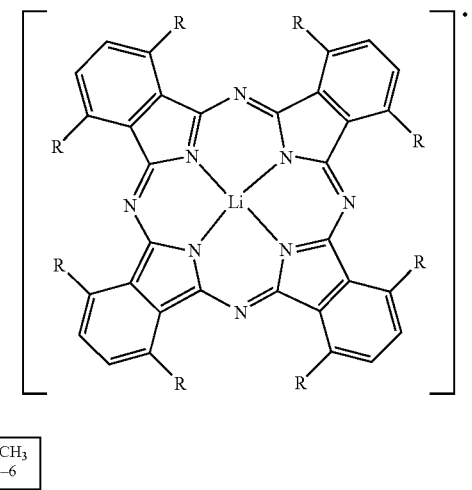

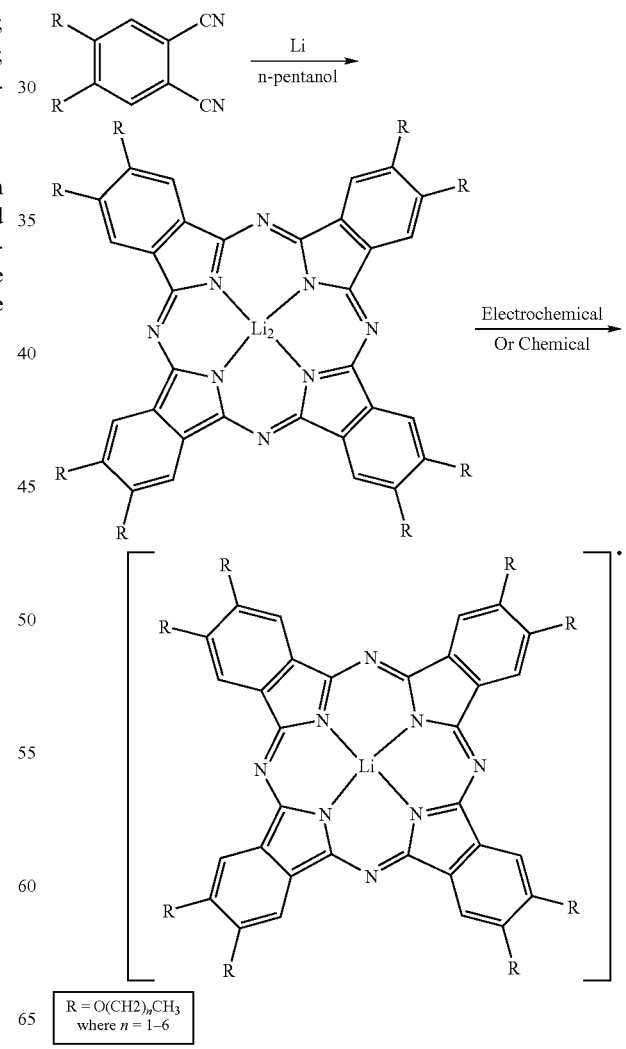

Scheme 3
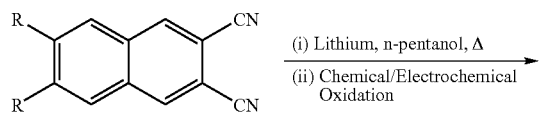
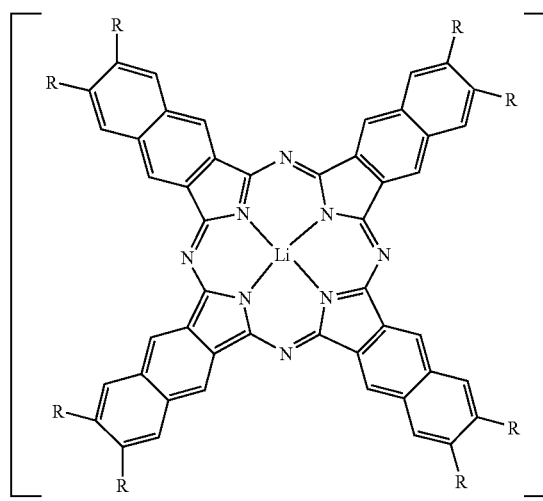
R = O(CH2)$_n$CH$_3$
where $n$ = 1–6
Scheme 4
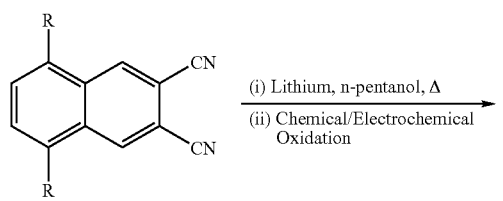
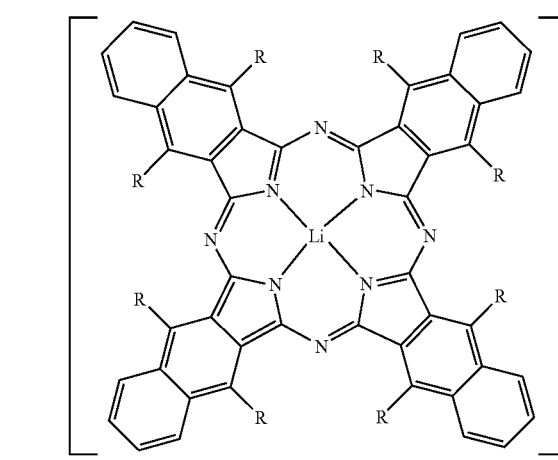
R = O(CH2)$_n$CH$_3$
where $n$ = 1–6
Scheme 5
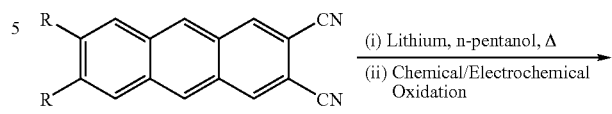
R = O(CH2)$_n$CH$_3$
where $n$ = 1–6
Scheme 6
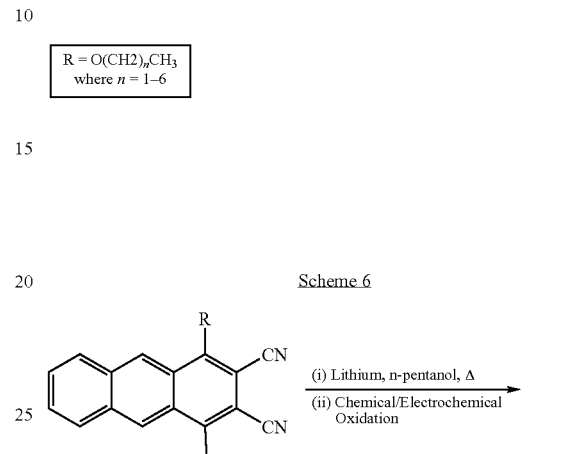
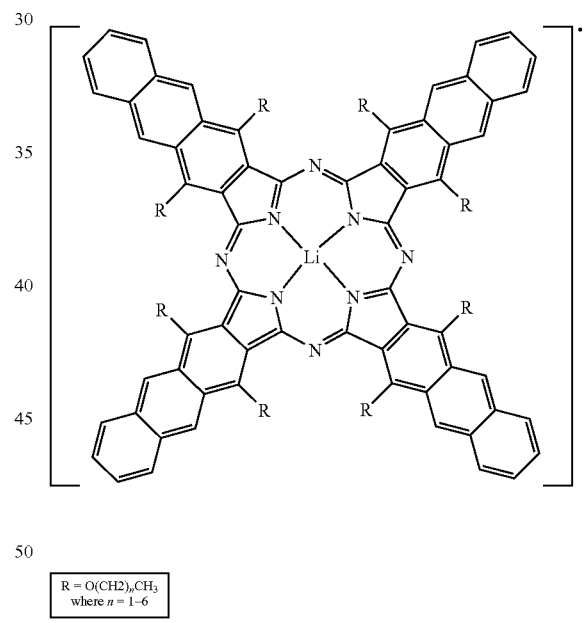
R = O(CH2)$_n$CH$_3$
where $n$ = 1–6
Scheme 7
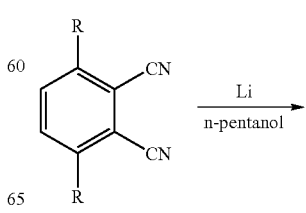

-continued
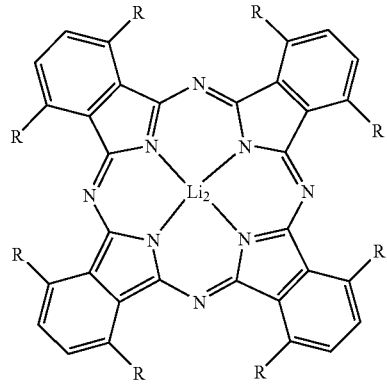
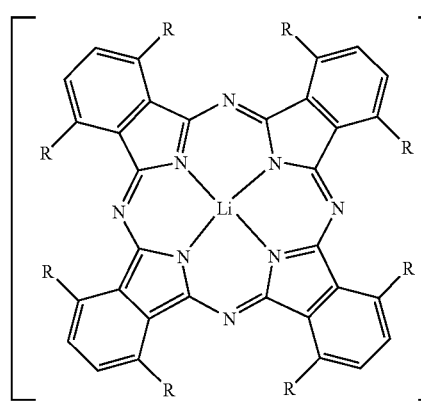
R = S(CH2)$_n$CH$_3$
where $n$ = 1–6
Scheme 8
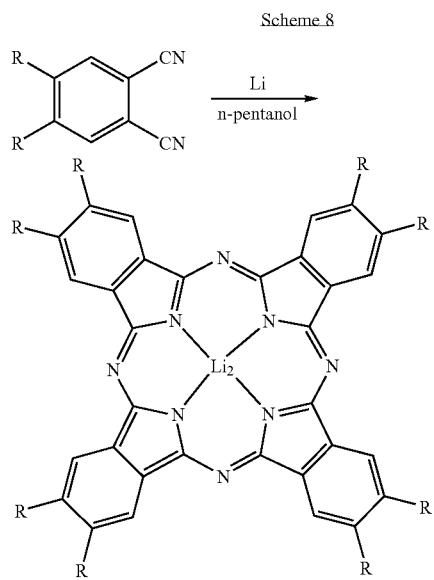
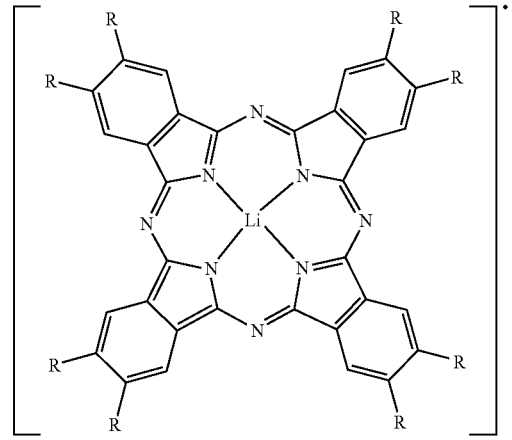
R = S(CH2)$_n$CH$_3$
where $n$ = 1–6
Scheme 9
(i) Lithium, n-pentanol, Δ
(ii) Chemical/Electrochemical Oxidation
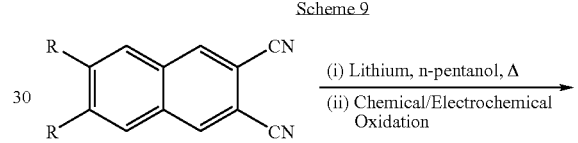
R = S(CH2)$_n$CH$_3$
where $n$ = 1–6
Scheme 10
(i) Lithium, n-pentanol, Δ
(ii) Chemical/Electrochemical Oxidation
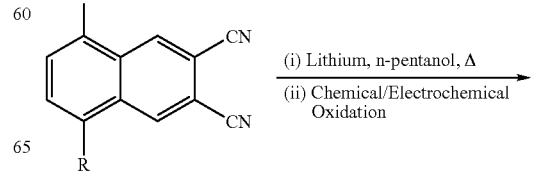

-continued
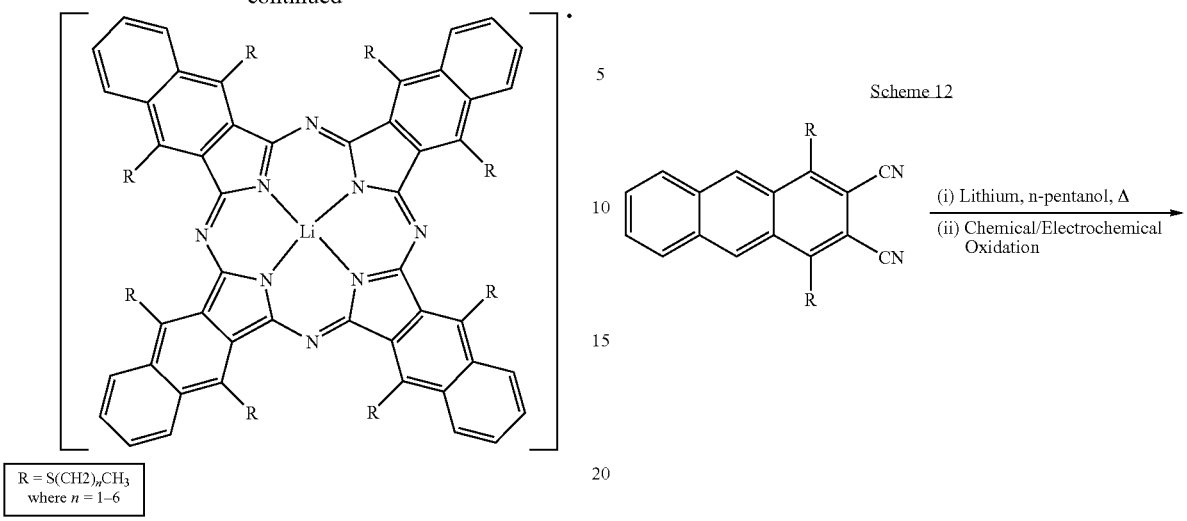
Scheme 12
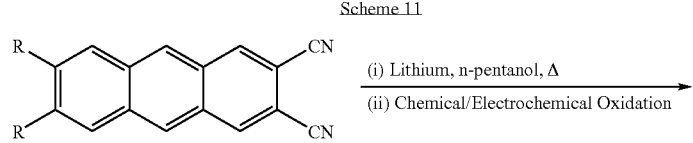
Scheme 11
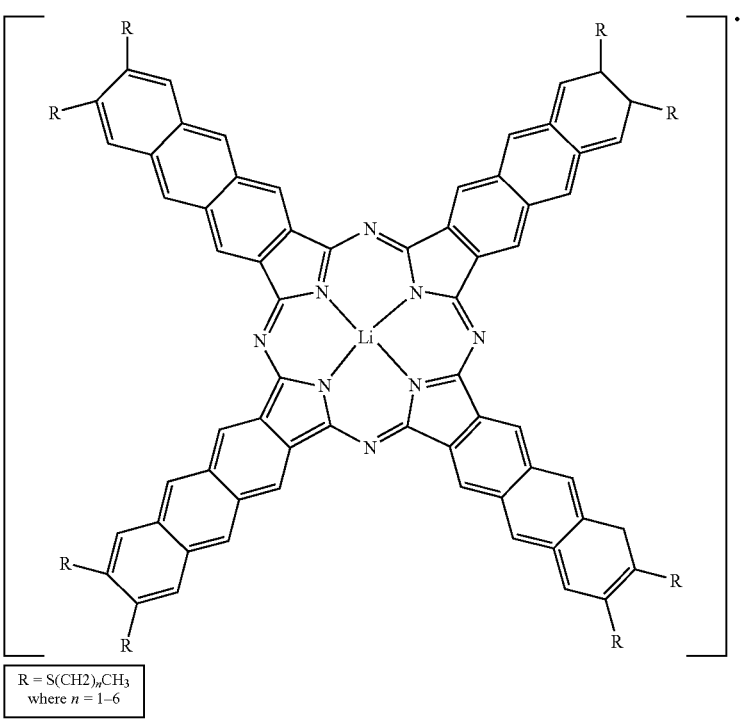

-continued

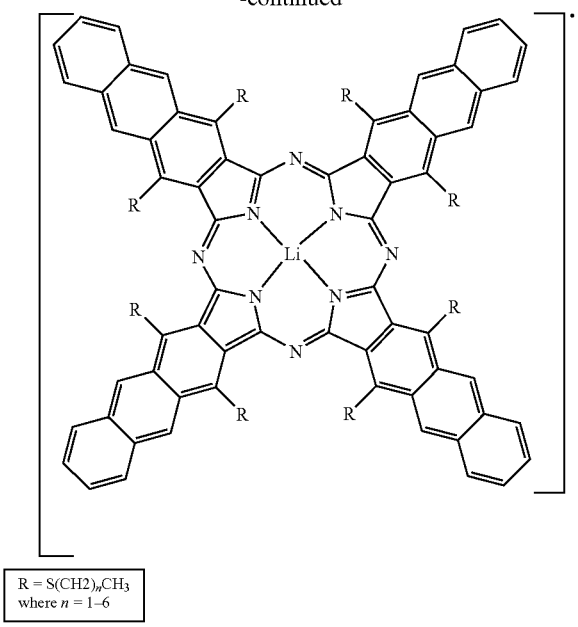

R = S(CH2)$_n$CH$_3$
where $n$ = 1–6

The spin probes are prepared as microcrystalline particles and characterized using X-ray diffraction and magnetic susceptibility techniques. The particles are suspended in complete medium containing 10% serum and sonicated with a probe sonicator. Alternatively the particles may be sonicated in presence of 1 mg/ml dioleoylphosphatidylcholine or lecithin to entrap the particles in liposomes and filtered through 0.22-10 micron filters to separate them according to the size. The EPR properties including oxygen sensitivity of the suspension are verified for each batch.

Several approaches known to those skilled in the art are used to further develop stable nanoprobe suspensions for iv or other systemic use. The following are taken into consideration in the development: biocompatibility (non-toxicity), preservation of oxygen sensitivity, and long-term shelf- and tissue stability in solutions of high ionic strength. In general, the suspension formulation requires a stabilizing agent, which adheres to the surface of the particle probe without blocking the oxygen active centers, which are responsible for the oxygen adsorption. The conformation and surface distribution of the agent or additive that is used to stabilize the suspension is taken into consideration. Fabrication of fine suspensions then requires milling of the probe particle using a ball mill and a homogenizer. Conventional methods of preparation of water-based colloidal dispersions using water-soluble stabilizers (low molecular weight surfactants like heparin and Tween; water-soluble polymers like pluriol), similar to described by Gallez et al. [43,44], may be used. Alternatively, dispersions may be prepared using organic solvent-based systems with water-insoluble stabilizers, and subsequently transforming them to aqueous system by adding water and removing the organic solvent. Another approach is to synthesize submicrometer-sized silica oxide suspension (silica gel) in the presence of the probe particles. This can produce coaggregates of the probe and silica dioxide. Smaller particles of silica gel can form an oxygen-permeable shell and thus protect the probe particles from forming bigger aggregates. Submicron (<0.22 micron) particulates with biocompatible coating formulations will be developed for iv infusion.

Targeted intracellular delivery of particulate oximetry probes Specially synthesized particulate oximetry nanoprobes, encapsulated in phospholipid liposomes (phosphatidylcholine and cholesterol) to facilitate rapid uptake into the cells, may be delivered into cells engineered for tissue or wound repair. Ligand-targeted liposomes and lipoplexes are highly useful as cargoes to deliver the nanoprobes to designated cell types in vivo [45-51]. Different types of ligands, such as receptors, peptides, vitamins, oligonucleotides or carbohydrates may be positioned onto the liposomal surface which will enhance the binding affinity [52-55]. The nanoprobe containing cells are characterized using optical confocal microscopy and EPR spectroscopy. Internalization techniques may be developed for the different stem or other cells to promote wound repair and used to image intracellular oxygen concentration, cell migration and proliferation of the targeted cell therapy.

DNA or protein-targeted spin probes As per the approach of Kursa et al. [56], novel shielded transferrin—polyethylene glycol—polyethylenimine DNA or protein complexes ligated with EPR probes (redox, NO, pH and O$_2$ probes) may be developed and used to study gene or peptide/protein delivery and concomitant localized oxygen and radical metabolic events. The use and ability of nonviral DNA complexes to deliver genes to cells and tissues in vivo offers a potential for delivery of DNA specific EPR probes [51, 57, 58]. Cell replication and cell cycle-specific gene expression in concert with oxygen and radical metabolism may be studied by delivering complexes that will be generated by mixing plasmid DNA, linear polyethylenimine, PEG and transferrin that provides a ligand for receptor-mediated cell uptake [57]. Cells in culture or in situ may be loaded with these complexes with a specific therapeutic gene (DNA) of interest and the oxidative and redox metabolism mapped.

Toxicology and pharmacokinetic evaluations as required for IND and FDA Approval Many of the paramagnetic molecules under development in this program have been extensively tested in animals and some even in human studies. Even at very-high applied concentrations of up to 150 mM no toxicity has been seen. With carbon-based micro and nanoparticulates there is a history of human application as in the marking of surgical fields with India ink. The naphthalocyanine particulates of the present invention have been chronically studied in small animals and no adverse effect or toxicity has been seen acutely or up to 3 months. We recognize the need for pharmacokinetic and toxicological testing particularly for systemic formulations.

Derivatives of phthalocyanines Phthalocyanine is planar macrocycles that contain four isoindole units and present 18 pi electrons cloud delocalized over an arrangement of alternating carbon and nitrogen atoms. The unique property of phthalocyanine comes from the electron delocalization, which can be easily modified by introducing a variety of structural alterations.

In addition to the prototype probe (LiNc—BuO) the present invention encompasses a series of substituted derivatives (R groups) and benzo-annulated derivatives (phthalo, naphthalo, and anthraphthalo) as illustrated in structures 1-18. In general, the derivatives of the present invention include: (i) Four different R groups: O—(CH$_2$)$_n$—CH$_3$, where n=1-6; O—(CH$_2$)$_n$—CH$_2$OH, where n=1-6; O—(CH$_2$)$_n$—CH$_2$NH$_2$, where n=1-6; O—(CH$_2$)$_n$—CH$_2$SH, where n=1-6; and combinations thereof; (ii) two different attachments/positions: Para and Ortho, and (iii) three different benzo-annulations: phthalocyanine, naphthalocyanine, and anthraphthalocyanine.

The compounds may be synthesized using any appropriate chemical or electrochemical procedures. The synthetic procedures will be optimized for each specific case. Syntheses for compounds 1-18 are shown, and suitable modifications can easily be made by those skilled in the art.

The Design of Lithium Phthalocyanine Derivatives as Oxygen-sensors Lithium metal has high mobility and smaller size compared to other alkali metals such as Na or K. This enables the metal ion to site in the center of the macrocycle allowing very tight stacking of the molecules in the crystal. This close packing results in highly exchange-coupled system with extremely narrow EPR lineshape. The benzo-annulations extend the delocalization of the unpaired electron in the molecule, which may reduce dipole-dipole interactions between the unpaired electrons in the stacked molecules. The absence or minimization of dipole-dipole interaction is highly preferred to obtain pure Lorentzian lineshapes. The substituents (R groups) are used as handles (i) to modulate the molecule-molecule distance in the crystal enabling different lineshape sensitivities to oxygen, (ii) to impart hydrophobicity to the particulate so that the material can be internalized or stabilized in biological tissues, (iii) to vary the inter-stack bore size in the crystal enabling desired molecules such as oxygen to freely diffuse into the crystal lattice and (iv) to establish anchor points to attach specific molecules to the crystal. Thus the probes: may be used for a range of biological applications as discussed below.

The lithium phthalocyanine derivatives, have low solubility in aqueous and common organic solvents. Unsubstituted annulated phthalocyanines are practically insoluble in organic solvents and are hard to purify and recrystallize. In order to have their functionality most effective, the lithium phthalocyanine derivatives with increasing solubility in organic solvents is planned. The insolubility of metal phthalocyanine derivatives results from their molecular stacking, which gives rise to strong intramolecular interaction between the macrocycles in phthalocyanine molecules. The introduction of long substituents in the macrocycle increases the solubility of the metal phthalocyanine derivatives.

Calculations of the electronic properties of annulated phthalocyanines show that linear annulations of benzene rings produces a continuous destabilization of the HOMO level and narrowing of the HOMO-LUMO energy gap. One-dimensional stacks of the linearly annulated phthalocyanines are calculated to have lower oxidation potentials and narrower gap than angularly annulated systems. These theoretical results are confirmed by studies on 1,2-naphthalocyanine, 9,10-phenanthrenocyanine and 2,3-naphthalocyanine and the corresponding bridged stacked systems. Benzoannulation with electron-releasing groups such as alkoxy group of lithium phthalocyanine increases the electron delocalization, and increase in spin electron intensity in the macrocycles.

In accordance with the present invention, the phthalocyanine or annulated phthalocyanine moieties may also be functionalized with groups such as hydroxyl, thiol or amino group. This phthalocyanine moiety may then be tagged with many biologically important molecules for detection by EPR spectroscopy and imaging.

The particulates are paramagnetic spin probes with very high spin density. The particulates are especially suitable for the following applications: (i) as an oxygen-sensing EPR probe for accurate determination of concentration of oxygen and (ii) as a molecular and cellular imaging probe for EPR/MRI methods. The probes may be used for many different applications in the field of biomedical research and clinical studies as set forth in the next several paragraphs.

(1) Determination of oxygen concentration in tissues: Electron paramagnetic resonance (EPR)-based oxygen measurements (oximetry) coupled with particulate probes have some unique advantages over the other methods. The particulate EPR probes for oximetry have the following advantages: (i) they report $pO_2$, which is a better parameter in a heterogeneous cellular system (ii) they do not consume oxygen (iii) they provide higher resolution at lower $pO_2$ and (iv) they are stable in cells and tissues for repeated measurements of oxygen tensions without reintroduction of the probe. The probe may be implanted in the desired location of the tissue and repeated measurements of tissue oxygenation may be performed over a period of several months. The measurements are accurate, reliable and noninvasive.

(2) Determination of oxygen concentration in cells In view of the importance of critical oxygen concentration in cells for operation of normal cellular events, methods capable of determining the oxygen concentration in cells and tissues are highly crucial. Although many methods are available to measure oxygen concentration in cells, each method has its advantages and disadvantages, and no single method is completely satisfactory for cellular studies The phthalocyanine micro/nano crystals can be easily internalized in cells by endocytosis. This will enable determination of oxygen concentration in cells. The high spin density of the particulates can enable measurements in a single cell.

(3) Determination of oxygen consumption by cells Cellular oxygenation and oxygen consumption rate (OCR) are important physiological and metabolic indicators of cellular function. Normal cellular function and homeostasis require a critical level of oxygen concentration (measured as oxygen tension, $pO_2$) in the cells to provide an adequate supply of oxygen for the mitochondrial oxidative phosphorylation process.

We have previously demonstrated that the octa-n-butoxy derivative of naphthalocyanine neutral radical (LiNc—BuO) enables accurate, precise and reproducible measurements of $pO_2$ in cellular suspensions. In the current study, we carried out measurements to provide an accurate determination of $pO_2$ in small volume with less number of cells (20,000 cells) that has not been possible with other techniques. This study clearly demonstrated the utilization of EPR spectrometry with LiNc—BuO probe for determination of oxygen concentration in cultured cells.

Additional applications include, but are not limited to: cell-tagging and cell-tracking applications; studying cancer metastasis in experimental models; tissue engineering (stem cell research); tagging antibody; MRI contrast agent; implantable oxygen-sensor in peripheral vascular disease; oxygen-sensor in wound healing applications; and implantable oxygen-sensor in cancer therapy.

NMR-based magnetic resonance imaging, MRI, enables visualization of the distribution of nuclear spins, mostly protons, in tissues. It has become a 'gold standard' for noninvasive diagnosis of tissue abnormalities. Electron paramagnetic resonance imaging (EPRI) is a parallel technology, which enables visualization of the distribution of electron spins (free radicals) in tissues. EPR is inherently about 3 orders of magnitude more sensitive than NMR. It can directly detect and image relatively stable free radicals as well as labile radicals such as oxygen-derived superoxide and hydroxyl free radicals that are implicated in the pathogenesis of oxidant injury. With spin labelling of molecules and cells, noninvasive mapping of their localization in tissues may be performed [59-62].

A major power of EPR technology is its ability to precisely measure molecular oxygen in tissues [61]. This 'EPR oximetry' technique uses spin probes whose EPR line-widths are highly sensitive to O$_2$ concentration. It enables precise and accurate measurements of O$_2$ in tissues, noninvasively and repeatedly over periods of weeks from the same site. The approach uses fine crystals (nano/microparticulates) of phthalocyanine-based radical molecules that are stacked to produce a very strongly exchanged-narrowed EPR line-shape that is highly sensitive to local O$_2$ concentration. The EPR line-shape of these nanoprobes is highly O$_2$ sensitive, and they are biocompatible and stable in tissues. They may be implanted at the desired site or with a suitable coating formulation can be infused into the vasculature for targeted delivery to tissues. In addition, we recently demonstrated that these nanoprobes can be internalized in cells enabling measurement of intracellular pO$_2$ with milliTorr accuracy The newly developed nanoparticulate EPR imaging technology is especially useful (i) to visualize and track the migration of endothelial progenitor cells and (ii) to simultaneously measure intracellular oxygenation. This is done by internalizing the paramagnetic nanoparticles (size <200 nm) by derivatizing with Tat protein-derived peptide sequences as reported by Lewin et al. [63]. The internalized cells may be characterized using optical confocal microscopy and EPR spectroscopy. The lithium naphthalocyanine (LiNc—BuO) spin probe, which has very high EPR spin density and is readily internalized in cells, is used. Imaging of the distribution of particles is performed in vivo using low-frequency (1.2 GHz) EPR imager. Measurement and mapping of intracellular oxygen concentration will be performed as we reported previously [64]. Additionally, the inventive particulates are suitable for the following applications for targeted intracellular delivery of particulate oximetry probes, and as DNA or protein-targeted spin probes, as discussed above.

Novel Particulate Spin Probe for Targeted Determination of Oxygen in Cells and Tissues The synthesis and characterization of a new lithium octa-n-butoxy-substituted naphthalocyanine radical probe (LiNc—BuO) and its use in the determination of concentration of oxygen (oximetry) by electron paramagnetic resonance (EPR) spectroscopy are reported. The probe is synthesized as a needle-shaped microcrystalline particulate. The particulate shows a single-line EPR spectrum that is highly exchange-narrowed with a line-width of 210 mG. The EPR line-width is sensitive to molecular oxygen showing a linear relationship between the line-width and concentration of oxygen (pO$_2$) with a sensitivity of 8.5 mG/mmHg. We studied a variety of physicochemical and biological properties of LiNc—BuO particulates to evaluate the suitability of the probe for in vivo oximetry. The probe is unaffected by biological oxidoreductants, stable in tissues for several months, and can be successfully internalized in cells. We used this probe to monitor changes in concentration of oxygen in the normal muscle and RIF-1 tumor tissue of mice as a function of tumor growth. The data showed a rapid decrease in the tumor pO$_2$ with increase of tumor volume. Human arterial smooth muscle cells, upon internalization of the LiNc—BuO probe, showed a marked oxygen gradient across the cell membrane. In summary, the newly synthesized octa-n-butoxy derivative of lithium naphthalocyanine has unique properties that are useful for determining oxygen concentration in chemical and biological systems by EPR spectroscopy and also for magnetic tagging of cells.

Aerobic life relies on oxygen for respiration and bioenergetic metabolism. In animals, especially mammals, under normal physiological conditions, oxygen delivery by blood to the tissues and tissue oxygenation are tightly regulated to maintain a balance [65], which is altered during many pathophysiological states. Therefore, an accurate and a reliable method to determine its concentration in biological systems is highly critical. Although several existing methods are utilized to measure oxygen concentration in absolute units or in some related parameter, a suitable technique for noninvasive and repeated measurements of oxygen in the same tissue or cells on a temporal scale is warranted. While electrode techniques have evolved as the standard methods for measurement of oxygen, they generate analytical artifacts during assay procedures at the freshly probed sites [66]. Near-infrared and magnetic resonance techniques such as nuclear magnetic resonance, blood oxygen level-dependent magnetic resonance imaging, Overhauser-enhanced magnetic resonance imaging, etc, on the other hand, are noninvasive methods, but they do not report usually the absolute values of oxygen concentration and lack the resolution of oxygen measurements [67-75]. Electron paramagnetic resonance (EPR), closely related to the aforementioned magnetic resonance techniques, enables reliable and accurate measurements of concentrations of oxygen [76]. The EPR technique requires the incorporation of an 'oxygen-sensing' paramagnetic spin probe into the system of interest. Two types of probes are used: (i) soluble probes that report the concentration of dissolved oxygen and (ii) particulate probes that measure partial pressure of oxygen (pO$_2$) in the milieu. Considerable progress has been made in the development and use of both types of probes [77-80]. The advantages in using the particulate probe are higher resolution and their suitability for repeated measurements in vivo without reintroduction of the probe into the tissue. Both the naturally occurring and synthetic materials have been useful for EPR oximetry [78, 79, 81-83].

Earlier, alkali metal derivatives of phthalocyanines such as lithium phthalocyanine (LiPcu) [77, 81, 84-86] and lithium naphthalocyanine (LiNc) [78, 87] were synthesized and their properties were studied in detail. The materials were characterized as crystalline solids composed of stacks of neutral free radical molecules [88]. The crystalline solids exhibit a highly exchange-narrowed single line EPR spectrum, whose width is sensitive to the partial pressure of molecular oxygen in the environment. Our interest in the utilization of oxygensensing radical probes for biological applications has lead to the synthesis and development of novel crystalline particulate materials with remarkable oxygen sensitivity and biocompatibility [77, 78, 85-87]. While we have identified that these materials enable us to perform accurate and repeated measurements of oxygen concentration in tissues, we realize that these particulate probes can very well be used in other physiological and biochemical studies that involve oxygen metabolism. The unique stability and paramagnetic property of these particulates can be exploited by internalizing them into cells and in specific tissues to visualize cell proliferation, migration and trafficking, as it is studied using superparamagnetic particulates in magnetic resonance imaging technology [89-91]. The EPR technique is advantageous in offering high sensitivity and direct detection of the particulates and reporting the absolute value of oxygen concentration in the environment. We envision that this creates a multitude of applications in cell-based therapies and tissue engineering [92, 93].

In order to qualify as an ideal spin probe for targeted measurements in cells and tissues, a paramagnetic particulate has to satisfy the following criteria: (i) high spin density with a simple EPR absorption peak, preferably a single and sharp line (ii) long-term stability in cells and tissues, maintaining its line-shape and oxygen sensitivity (iii) non-toxicity to the host cell or tissue (iv) ability to prepare particulates of various sizes, and (v) ability to encapsulate in shells or coating to enable attachment of other probes such as fluorescent labels. Although a variety of paramagnetic spin particulates, including natural [82, 94] and semisynthetic [83, 95, 96] has been reported to be useful as oximetry probes, they do not satisfy most of the above requirements. Hence, we focused our efforts on synthetic molecular crystalline particulates, whose properties can be controlled and systematically altered by appropriate molecular designs [77, 78, 85-87]. In this manuscript, we report the synthesis, characterization and application of a new paramagnetic particulate spin probe. The probe is a lithiated form of octa-n-butoxynaphthalocyanine neutral radical (FIG. 1) which is obtained in a microcrystalline form. The preliminary results indicate that the probe is useful for determining oxygen concentration in chemical and biological systems by EPR spectroscopy and that it may significantly expand the capability of EPR oximetry.

Materials and Methods Lithium granules, 5,9,14,18,23,27, 32,36-octa-n-butoxy-2,3-naphthalocyanine (Nc—BuO), n-pentanol, n-hexane, tetrahydrofuran and tert-butyl methyl ether were obtained from Aldrich Chemical Co (St. Louis, Mo.). Minimal essential medium (MEM), Dulbecco's modified Eagle medium (DMEM), fetal bovine serum (FBS), glutamate and antibiotic (penicillin-streptomycin) were purchased from Invitrogen, San Diego, Calif. Alamar Blue solution was purchased from Biosource International (Camarillo, Calif.).

Synthesis of Lithium 5,9,14,18,23,27,32,36-octa-n-butoxy-2,3-naphthalocyanine (LiNc—BuO) Radical Lithium granules (0.0053 g, 0.774 mmol) were added to n-pentanol (15 ml) and refluxed for 30 min under nitrogen atmosphere. The mixture was cooled down to room temperature and Nc—BuO (0.1 g, 0.0774 mmol) was added and refluxed gently for 2.5 h under nitrogen atmosphere. After cooling down to room temperature, 300 ml of tert-butyl methyl ether was added and filtered through a small silica gel plug. The solvent was evaporated under reduced pressure to 3 ml of solution. The concentrate was dissolved in 100 ml of n-hexane. The greenish solution was slowly evaporated under reduced pressure to yield shiny crystals of lithium 5,9,14,18,23,27,32,36-octa-n-butoxy-2,3-naphthalocyanine. The crystals were washed with methanol and dried under vacuum. The yield was 81%. Microanalysis of the product was in good agreement with the formula $C_{80}H_{88}N_8O_8Li$ (Calculated: C, 74.1; H, 6.84; N, 8.6; Li, 0.53 Found: C, 73.9; H, 7.12; N, 7.89; Li, 0.55).

Physicochemical Characterizations Electronic absorption spectra were measured in tetrahydrofuran solvent using a Cary 300 BIO UV-Visible Spectrophotometer. X-ray diffraction measurements were performed using a Bruker D8 Advance model X-ray diffractometer operating at 40 kV and 50 mA with Cu Klá radiation (e=1.5406 Å) using a Braun position-sensitive detector.

EPR Measurements EPR measurements were performed using a Bruker ER-300 spectrometer operating at X-band (9.78 GHz). The spectral acquisitions were carried out using custom-developed software (SPEX). Unless mentioned otherwise, the EPR line-widths reported are peak-topeak width (.Bpp) of the first derivative spectra. The EPR line-width versus partial pressure of oxygen calibration curve was constructed from X- and L-band EPR measurements on LiNc—BuO equilibrated with oxygen/nitrogen gas mixture as reported previously [78].

Animal Studies Female C3H mice were used in the present work. The mice were supplied through the Frederick Cancer Research Center Animal Production, Frederick, Md. The animals were received at 6 weeks of age and housed five per cage in climate-controlled rooms and allowed food and acidified water ad lib. The animals were on average 50 days old at the time of experimentation and weighed 25±3 g. Experiments were conducted according to the principles outlined in the Guide for the Care and Use of Laboratory Animals prepared by the Institute of Laboratory Animal Resources, National Research Council.

RIF-1 Tumor Growth Radiation-induced fibrosarcoma (RIF-1) tumor cells, grown in monolayered culture, were injected subcutaneously in the right hind leg with a single cell suspension of 106 cells in 0.1 ml PBS. The animals were observed closely and the tumors became palpable approximately 5 days after injection.

Implantation of LiNc—BuO in Tumor and Gastrocnemius Muscle of Mice Mice were anesthetized with breathing of isoflurane (1.5%)—air mixture delivered through a nose cone. About 10 μg of LiNc—BuO in the form of microcrystalline powder (particulate size 5-20 μm) was implanted in the tumor (right leg) or gastrocnemius muscle of normal leg (left), using a 21-gauge needle loaded with the particulate in the tip, and a wire stylus. The material was deposited at desired locations of the tissue by inserting the needle and then pulling it back, but keeping the wire stylus stationary and then removing the stylus from the tissue. In the case of tumors, the material was carefully implanted at the center of the tumor at about 3 mm depth. The site of the probe insertion was marked with a permanent marker for convenient preparation of the animal for repeated measurements. All the in vivo EPR measurements of LiNc—BuO in mice were made at least 24 h after the implantation.

In Vivo EPR Measurements in Mice The EPR measurements were carried out on anesthetized mice using L-band (1.32 GHz) spectrometer and a topical (surface loop) resonator as described [33]. A plastic bedplate with a circular observation window (20 mm diameter) was used to rest the animal on the resonator. The animal was placed on the bedplate so that the observation spot was centered at the slot. The animal was secured to the bedplate with adhesive tape and placed on top of the resonator so that the tumor or the normal muscle was in direct contact with the active surface of the resonator. Anesthesia was maintained during the measurements with continuous delivery of 1.5% isoflurane mixed with air using a veterinary anesthesia system (Vasco Anesthesia, Pro Tech Medical Inc., Hazel Crest, Ill.). The flow rate of the breathing gas mixture was maintained at 2 L/min. The gas and anesthesia were delivered to the animal through a nose cone and the excess air was removed through proper ventilation maintaining the atmospheric pressure (760 mmHg). A thermistor rectal probe was used to monitor body temperature. The body temperature was maintained at 37±1° C. using an infrared lamp.

Culture of Smooth Muscle Cells Human arterial smooth muscle cells (HASMCs) were obtained from Clonetics, San Diego, Calif. at passage 4. Cells were cultured and passed in Ham's medium containing 225 ml of DMEM, 225 ml of F-12 medium, 50 ml of FBS (1:0%), 5 ml of glutamate and 5 ml of antibiotics in a final volume of 500 ml. Cell cultures were maintained at 37° C. under 95% air/5% CO2 environment in 35 mm dishes. HASMCs up to passage 11 were used in the current study.

Preparation of Particulates for Cell Culture Studies Fine Crystals of Freshly synthesized LiNc—BuO were suspended in Ham's medium (10 mg/0.5 ml) and sonicated ten times for 30 sec on ice with a probe sonicator at a setting of 5. The particulate mixture was cooled on ice for 1 min between two successive 30 sec burst of sonication. At the end of the final round of sonication, the suspension was placed on ice for exactly 2 min to allow the heavier particulates to settle down at the bottom of the tube and the decanted liquid was transferred to a separate tube, which contained fine particulates of LiNc—BuO for intracellular delivery. The size of the particulates for intracellular delivery was <2 μm as determined by optical microscopy.

Internalization of Particulates into Smooth Muscle Cells HMSMCs, at 70% confluence (104 cells/dish), in 1 ml Ham's medium were treated with 50 μl of LiNc—BuO particulate suspension that contained particulates of <2 μm prepared by the procedure as mentioned before. The cells were maintained at 37° C. under 95% air/5% CO2 environment. At 6 h intervals, for 72 h, cells were examined under light microscope for internalization of LiNc—BuO particulates. Upon confirming the particulate uptake by all the cells in a given dish, the cells were washed 12 times with ice-cold DMEM to remove unincorporated and extraneous particulates by gentle swirling and aspiration, scrapped in 1 ml of DMEM, and centrifuged at 1000× g in a microfuge for 10 min. The resulting cell pellet was gently resuspended in DMEM containing glucose (0.5 g/500 mL) for EPR analysis. Cells after LiNc—BuO internalization and repeated washings were photographed under an inverted microscope while still adherent to the substratum of the 35 mm dish. Cell viability was assessed by light microscopy and Alamar Blue assay according to the manufacturer's recommendations.

Results: Physicochemical Characterization LiNc—BuO was synthesized as dark-green needle-shaped crystals of varying sizes, typically with 1-5 μm diameter and 5-50 μm length. The crystals were insoluble in water, but soluble in chloroform, dichloromethane, tetrahydrofuran, toluene, benzene and xylenes giving rise to green-colored solution. The crystals were stable in air at ambient conditions. The UV-visible absorption spectrum of LiNc—BuO solution in tetrahydrofuran showed strong Q-bands at 857 and 705 nm and a weak split Soret band at 449 nm, while the Nc—BuO (the macrocyclic ligand without Li) showed a strong Q-band at 865 nm. X-ray diffraction pattern showed strong diffraction peaks suggestive of a high degree of crystallinity. A thorough investigation of the optical, magnetic, and structural property of LiNc—BuO will be published elsewhere [34]. Most of the studies were performed on fine crystals of LiNc—BuO, with <2 μm in size, obtained by sonication of the originally synthesized material in PBS or Ham's medium containing 10% fetal bovine serum. This was done to achieve particulates of uniform size for internalization in cells and tissues. We used the term 'particulates' to refer to these crystals throughout the manuscript.

EPR Properties The LiNc—BuO particulates exhibit a single-line EPR spectrum at room temperature (FIG. 2). The peak-to-peak width of the spectrum was highly dependent on the oxygen concentration of environment: 210 mG under anoxic (0% oxygen) conditions, 1550 mG in room air (20.9% oxygen or 159 mmHg) and 6675 mG in 100% oxygen at 1 atmospheric pressure (760 mmHg). The shape of the spectrum was 100% Lorentzian. This is evidenced from the very good agreement between the experimental and simulated spectra in FIG. 2A and the random noise in the difference spectrum (FIG. 2B). The spin density, measured in comparison with diphenylpicrylhydrazyl (DPPH) radical, was 7.2× 1020 spins/g. Microwave power saturation studies of LiNc—BuO were performed to establish the useable range of power levels. It was observed that spectrum was not saturable for up to 25 mW at the X-band frequency. This shows that up to 25 mW microwave power can be applied to enhance the signal intensity without compromising the oxygen sensitivity. Both the line-width and lineshape of the particulates were not affected in aqueous dispersion media (water, PBS, cell culture media). However, no EPR spectrum was observed in organic solvents, in which the compound is freely soluble, suggesting that the radical is not stable in the molecular form.

Effect of Molecular Oxygen The peak-to-peak width of the EPR spectrum of LiNc—BuO particulates was sensitive to oxygen concentration of the environment. The spectrum was broadened and its amplitude decreased in presence of oxygen. The oxygen-dependent broadening of the EPR spectrum has been observed with LiPc, LiNc and several other paramagnetic solids [77-79, 85-87, 99-101]. It is generally considered that the broadening in presence of molecular oxygen is due to the Heisenberg spin exchange between the radical and molecular oxygen and results in shortening of the spin-spin relaxation time T2. A plot of line-width measured as a function of oxygen partial pressure is shown in FIG. 3. It is observed that the line-width increases linearly with $pO_2$ in the range 0 to 760 mmHg suggesting that the spin exchange increases linearly with $pO_2$. The slope of the line-width versus $pO_2$ curve, which reflects the oxygen sensitivity of the probe line-width, is 8.5 mG/mmHg.

Effect of Biological Oxidoreductants, pH, Temperature, and Radiation Since our goal was to use the newly synthesized particulate material for biological applications, we thoroughly investigated the EPR stability (paramagnetism) as well as sensitivity of the EPR line-width to molecular oxygen in presence of a variety of biological oxidants, reductants, pH and radiation. The particulates when exposed to superoxide (generated by 0.2 mM xanthine+0.01 U/ml xanthine oxidase), hydroxyl (generated by 0.1 mM $Fe^{2+}$+1 mM $H_2O_2$), hydrogen peroxide (1 mM), singlet oxygen (generated by 1 mM Rose Bengal+light), alkylperoxyl (generated by aerobic decomposition of 10 mM AAPH at 37° C.), and nitric oxide (generated by 1 mM SNAP), GSH (10 mM) and ascorbate (5 mM) for 30 min did not show any effect on the EPR spectrum or oxygen response. We also observed that pH of the medium in the range 2-10 had no effect on their EPR sensitivity to oxygen. We also treated the particulates with 15.5 Gy of Cobalt-60 ã-ray irradiation for 10 min and found no effect on the EPR properties of the particulates. These results suggest that the LiNc—BuO particulates are usable in a variety of extreme biological environments without any adverse effect on the integrity of data.

Stability in Tissues In order to evaluate the long-term stability of these particulates in tissues, we implanted the particulates in the gastrocnemius muscle tissue of mice and performed repeated measurements of $pO_2$ in the same animals over a period of time. About 10 μg of LiNc—BuO microcrystalline powder was implanted in the gastrocnemius muscle of the right leg of C3H mice (N=6). The EPR spectrum of the particulate in the leg was recorded periodically up to 180 days following the implantation of particulate (FIG. 4). In order to verify the response of the particulate to oxygen, blood flow to the leg was constricted by gentle tying down of the upper leg for 10 min with an elastic band and the EPR measurement was repeated. Sharpening of the EPR spectral width during interruption of blood flow to the leg was used as an indication of reduced tissue oxygenation and responsiveness of the particulate to changes in tissue $pO_2$. The $pO_2$ of the tissue under normal blood flow conditions was 19.6±2.1 mmHg, while that of constricted tissue was 3.5±0.9 mmHg during the 180 day period. The non-zero $pO_2$ values in the flow-constricted tissue suggest that the constrictions were not totally effective. This was due to our efforts to make the measurements for at least 6 months and so deliberately avoided inflicting any permanent injury to the tissue while constriction. Mice were periodically sacrificed through the 180 day study period and tissue $pO_2$ values were assessed to verify the registration of anoxic $pO_2$ in the dead tissue. The pO$_2$ values in the dead tissues were close to zero. We also observed that the oxygen sensitivity of the recovered particulates from the dead tissue was not changed and was similar to that of the original unimplanted particulate.

Time-Response to Changes in Oxygenation The response time and reproducibility of the effect of O$_2$ in successive measurements were evaluated. The response of probe was measured from the change in the EPR amplitudes to cycles of rapid switching of the equilibrating gases between nitrogen and room air as described previously [78]. It was observed that the response was reasonably quick with oxygenation occurring at ~1 sec, while deoxygenation at ~20 sec. Similar values of response time and amplitude were observed on successive cycles of switching of gas. Thus, the experiments not only confirm that the probe responds quickly to oxygen and offers steady reproducibility, but also that oxygen is not irreversibly adsorbed and that the absorption/desorption process is very rapid and reversible. Thus, the probe apparently is capable of responding to changes in oxygen concentration almost instantaneously. A similar observation has also been reported in the case of LiPc and LiNc crystals [78].

Measurement of Tumor pO$_2$ as a Function of Tumor Growth The LiNc—BuO particulate was implanted in the tumor on day 5 after inoculation with tumor cells. The average tumor size at the time of implantation of the particulate was 6 mm in diameter. A similar implantation of the particulate, as a control, was performed in the normal muscle on the left leg of the same tumor-bearing mice. Tissue pO$_2$ measurements were taken 24 h following implantation to avoid artifacts associated with trauma and tissue injury caused by the particulate implantation procedure. Measurements were performed in the tumor on the right leg and in the normal muscle on the left leg of each animal daily for the following 8 days. The mean pO$_2$ values from the tumor and muscle tissue in 7 tumorbearing mice are shown in FIG. 5. It was observed that while the pO$_2$ in the muscle tissue (control) of the RIF-1 tumor-bearing mice remained constant during the study period (17.6±2.5 mmHg), the tumor PO$_2$ showed a continuous decrease towards hypoxia (<4 mmHg). It was also observed that the RIF-1 tumor showed an accelerated growth during the same period suggesting that the decrease in tumor oxygenation may be related to tumor progression. The measurements were discontinued beyond day 8 as the tumors were too big (>20 mm in diameter) and continued to be hypoxic with pO$_2$ levels <4 mmHg.

Intracellular Internalization of Particulates The light microscopy clearly showed that within 18 h of treatment of HASMCs with LiNc—BuO particulates (<2 μm) in Ham's medium, almost all the cells in the 35 mm dish internalized the particulates. There was no apparent cytotoxicity of the particulates up to 72 h following their internalization as revealed by the light microscopy and Alamar Blue cytotoxicity assay (data not shown).

Measurement of Intracellular pO$_2$ in Smooth Muscle Cells The particulates obtained by sonication of the LiNc—BuO crystals in Ham's complete medium containing 10% fetal bovine serum were internalized into cells. The extracellular uninternalized particulates were removed by repeated washings with medium. FIG. 6 shows a photograph of cells internalized with the particulates. The intracellular oxygen concentration, measured from the internalized particulates, was 142±2 mmHg, while the extracellular pO$_2$ was measured to be 158±3 mmHg using unsonicated particulates that were added to control cells (without internalized particulates) prior to measurement. The data show that the particulates are capable of reporting exclusively intracellular pO$_2$ when internalized into the cells.

Discussion The LiNc—BuO belongs to a new class of crystalline internal spin probe (CRISP) that has several advantages over the previously reported particulate probes, namely lithium phthalocyanine [77, 81] and lithium naphthalocyanine [78]. Although LiNc—BuO is a derivative of the other two, closely similar in molecular structure, its properties are very different from its predecessors. Some of the distinct and advantageous features of LiNc—BuO paramagnetic spin particulates are: (i) their ability to give rise to a single, sharp and isotropic EPR spectrum characterized by 100% Lorentzian shape obtained from crystalline powder (ii) their relatively very high spin density compared to LiPc or LiNc (iii) they exhibit a linear variation of line-width with pO$_2$ that is independent of particulate size (iv) their long term stability in tissues and (v) their ability to internalize in cells. In addition the LiNc—BuO particulates also show typical auto-fluorescence properties which are under investigation. A complete three-dimensional X-ray structure elucidation of the crystals is in progress.

The anoxic line-width of LiNc—BuO is 210 mG. This is larger when compared to that of LiPc, which we have reported to be <20 mG [77, 81]. However, the value is smaller than that of LiNc (510 mG) though the LiNc is structurally closer to the LiNc—BuO [78]. This difference in the anoxic line-width of LiNc—BuO may be attributed to changes in the exchange interaction caused by the introduction of alkoxy substituents to the naphthalocyanine macrocycle. On the other hand, the oxygen sensitivity of LiNc—BuO (8.5 mG/mmHg) is much closer to that of LiPc (8.9 mG/mmHg) than that of LiNc (28.5 mg/mmHg). These differences in properties among the particulates suggest that even a small change in the structure can result in substantial change in the electron exchange and oximetry properties.

The apparent spin density of LiNc—BuO (7.2×1020 spins/g), measured in comparison with diphenylpicrylhydrazyl (DPPH) radical, is seven-fold higher than that of LiPc and comparable to that of LiNc (6.8×1020 spins/g). The observed spin density of LiNc—BuO, only a relative value, is determined by comparing the intensities of the EPR spectra of LiNc—BuO with DPPH measured under identical experimental conditions. However, the nature of spin dynamics could affect the absolute value of spin density in the system as discussed for LiNc [78].

The oxygen-dependent broadening of the EPR spectrum has been observed with LiPc, LiNc and several other paramagnetic solids [77-79, 85-87, 99-101]. The broadening in presence of molecular oxygen is generally attributed to the Heisenberg spin exchange between the radical and molecular oxygen and results in shortening of the spin-spin relaxation time T2 [102]. Alternatively, as per the mechanism proposed recently for LiPc microcrystalline powders [86], the O$_2$ can trap the self-exchanging or diffusing spins resulting in broad EPR lines. The latter mechanism is more probable especially for the solid spin probes with self-interacting spins.

An important drawback with many particulate oximetry probes was the instability of the probe in live tissues for prolonged periods of time. The most widely used LiPc particulate is stable in the gastrocnemius muscle tissue of mice for only about 3 weeks, beyond which the probe apparently looses its sensitivity to oxygen. Though the LiNc probe has several other advantages over LiPc, its stability in tissue was limited to only a few days. There were intense efforts to enhance their tissue stability over longer periods of time, but however, there has been no significant success to date [99, 103, 104]. Thus, it is important to note that LiNc—BuO has tissue stability for 6 months, and appears to last longer.

We have demonstrated the usefulness of the probe for making repeated and noninvasive measurements in a RIF-1 murine tumor model. The data show that the $pO_2$ levels in the normal (nontumor-bearing) leg muscle are more or less constant while the values in the tumor of the same set of animals progressively decreased to hypoxic levels during the measurement period. It is particularly important to note that there are relatively small variations in the $pO_2$ between the tumors as seen from the data analysis. This observation suggests that the oxygen concentration in the RIF-1 tumor decreases as a function of tumor growth.

Though the implantation of the particulates into the tissue is invasive, it differs from other routine invasive techniques in many ways. For example, in the case of the commonly used Eppendorf electrode technique, the electrode is inserted at each sampling time during the measurement causing local tissue injury and the $pO_2$ readings are obtained each time from the freshly injured site. Although in the case of particulate probes, the implantation procedure is invasive, the measurements are performed for days following the implantation of the particulate probe at the tissue sites where wound healing occurs after preparative surgery. Furthermore, the implanted probe can be used repeatedly, as long as the probe is stable and responsive to oxygen, without repeated insertions and surgery. Thus, the EPR oximetry technique is minimally invasive in terms of the requirement of one time implantation and surgery and thus enables subsequent noninvasive measurement of concentration oxygen from the same location.

The advantage of LiNc—BuO is the ability to make particulates of nanometer size without compromising its EPR and oxygen-sensing abilities. The smaller particulates can be internalized in a variety of cells for different applications. For example, intracellular $pO_2$ can be measured from single cells. It is also possible to tag cells with the EPR particulate probes and study their migration, infiltration and proliferation over a period of time using EPR or MRI technologies, in vivo. This will be similar to the capabilities of ultra small superparamagnetic particulates of iron oxide (USPIO) that have been actively pursued as contrast agents in magnetic resonance imaging [105-107]. The crystalline internal spin probe (CRISP) technology has biomedical applications including tissue repair, wound healing and oximetry, where in vivo EPR spectroscopy and imaging can be used. The EPR spectroscopy has the advantage of direct detection of these particulates, compared to the contrast-based detection by MRI, as well as the capability of measuring absolute concentration of oxygen concentration in cells and tissues.

Summary and Conclusions A new butoxy-substituted naphthalocyanine-based radical probe, LiNc—BuO, with striking EPR properties was synthesized as fine crystals and characterized with significantly high spin density. The probe showed a highly exchange-narrowed single line EPR spectrum that was sensitive to the surrounding oxygen concentration. The effect of molecular oxygen on the EPR line width was linear for up to 760 mmHg and highly reproducible on successive applications, suggesting that it can be used as a probe for EPR-based oximetry application. The probe has definitive advantages over other EPR oximetry probes reported earlier. The EPR spectrum is nonsatuarable up to 25 mW microwave power levels, and hence the signal to noise ratio can be substantially improved by increasing microwave power during measurements. The sensitivity of the EPR linewidth to molecular oxygen is 8.5 mG /mmHg which suggests that changes in $pO_2$ can be measured with reasonable resolution (~0.2 mmHg) using this probe under the experimental conditions described in this work. The probe shows a linear response of its line-width to $pO_2$ up to 100% molecular oxygen (760 mmHg), thereby enabling the measurement of the $pO_2$ even in the higher range while maintaining the sensitivity. The probe is stable against a variety of biological oxidoreductants, stable in tissues for more than 6 months, and can be readily internalized in cells. Thus the new octa-nb-utoxy derivative of LiNc has unique properties that may be useful for determining oxygen concentration in chemical/biological systems and for magnetic tagging of cells.

Measurement of Oxygen Consumption in Mouse Aortic Endothelial Cells Using a Microparticulate Oximetry Probe The purpose of this study was to determine the rate of oxygen consumption in mouse aortic endothelial cells (MAECs) and to determine the effect of a variety of inhibitors and stimulators of oxygen consumption measured by electron paramagnetic resonance (EPR) spectroscopy utilizing a new particulate oximetry probe. We have previously demonstrated that the octa-n-butoxy derivative of naphthalocyanine neutral radical (LiNc—BuO) enables accurate, precise and reproducible measurements of $pO_2$ in cellular suspensions. In the current study, we carried out measurements to provide an accurate determination of $pO_2$ in small volume with less number of cells (20,000 cells) that has not been possible with other techniques. In order to establish the reliability of this method, agents such as menadione, lipopolysaccharide (LPS), potassium cyanide, rotenone and diphenyleneiodonium chloride (DPI) were used to modulate the oxygen consumption rate in the cells. We observed an increase in oxygen consumption by the cells upon treatment with menadione and LPS, whereas treatment with cyanide, rotenone and DPI inhibited oxygen consumption. This study clearly demonstrated the utilization of EPR spectrometry with LiNc—BuO probe for determination of oxygen concentration in cultured cells.

INTRODUCTION Cellular oxygenation and oxygen consumption rate (OCR) are important physiological and metabolic indicators of cellular function. Normal cellular function and homeostasis require a critical level of oxygen concentration (measured as oxygen tension, $pO_2$) in the cells to provide an adequate supply of oxygen for the mitochondrial oxidative phosphorylation process [108, 109]. However, when the cellular oxygen level is altered from the critical level, the cellular homeostasis is disrupted leading to abnormalities in: cell growth, differentiation and survival. It is established that too little of oxygen (hypoxia) can lead to the activation of certain enzymes such as NAD(P)H oxidase, which results in the generation of reactive oxygen species (ROS) [110]. It is further shown that too much of oxygen (hyperoxia) may also lead to the generation of ROS from the mitochondrial electron transport chain and other sources [111]. The ROS cause oxidative stress by oxidizing the cellular components and by ultimately altering their structure and function. Although cells have evolved numerous antioxidant defense mechanisms against ROS-induced oxidative stress, for example, using superoxide dismutase, catalase, glutathione peroxidase, and vitamin E, the concentration of oxygen in cells must be carefully controlled by maintaining a balance between the ROS and antioxidants. In fact, the concentrations of oxygen must be regulated such that the energy needs of the cell via oxidative phosphorylation are adequately met without a large excess of oxygen.

In view of the importance of critical oxygen concentration in cells for operation of normal cellular events, methods capable of determining the oxygen concentration in cells and tissues are highly crucial. Although many methods are available to measure oxygen concentration in cells, each method has its advantages and disadvantages, and no single method is completely satisfactory for cellular studies [112]. Electron paramagnetic resonance (EPR)-based oxygen measurements (oximetry) coupled with particulate probes [113-118] have some unique advantages over the other methods. The particulate EPR probes for oximetry have the following advantages: (i) they report $pO_2$, which is a better parameter in a heterogeneous cellular system (ii) they do not consume oxygen (iii) they provide higher resolution at lower $pO_2$ and (iv) they are stable in cells and tissues for repeated measurements of oxygen tensions without reintroduction of the probe. A variety of particulate probes possess many of these desirable properties and thus are useful for several in vitro and in vivo clinical applications [113-118]. Particularly, lithiated macrocycles of phthalocyanine and naphthalocyanine have been extensively investigated [113, 114]. Recently, we synthesized and characterized octa-n-butoxy derivative of naphthalocyanine neutral radical (LiNc—BuO), an analog of phthalocyanine with extended benzoannulation [119]. The LiNc—BuO neutral radical (oximetry probe), as opposed to LiPc [113], fusinite [117], glucose char [118] etc., offers marked advantages, especially with regards to low microwave power saturation, linear response to concentration of oxygen, dynamic measurement range and higher spin density. Recently, we demonstrated the utilization of this material to measure oxygen concentration in intact cells and in vivo biological systems with greater stability (>6 months in the gastrocnemius muscle of mice) and reproducibility in aqueous and physiological environments [119]. Our earlier studies demonstrated that the LiNc—BuO microcrystalline powder can provide accurate and repetitive measurements of oxygen concentrations in intact cells and tissues.

In order to demonstrate the accuracy and reliability of the EPR oximetry utilizing the LiNc—BuO probe, we studied the $pO_2$ and oxygen consumption rate (OCR) in mouse aortic endothelial cells (MAECs). These cells can be cultured easily and considered as an established model for endothelial cells that are widely used [120]. The reported OCRs in endothelial cells range from 0.13 nmol/min/106 cells [121] to 87.5 nmol/min/106 cells [122]. The disparity in results, however, may be due to several factors including differences in the cell type, experimental conditions and choice of method. It should be noted that cellular metabolism can vary profoundly depending on the conditions of incubation, presence and absence of serum, growth factors and hormones and type of cell line used in the study.

The purpose of this study was to determine the basal OCR in MAECs of low cell density by EPR spectroscopy utilizing the LiNc—BuO particulate oximetry probe that is capable of providing accurate and reliable measurements of $pO_2$ in cellular suspensions. We demonstrated such measurements in a small volume (20 μl) with as few as 20,000 cells. We also investigated the reliability of the method by studying the effect of several stimulators and inhibitors of cellular oxygen consumption. Menadione, and lipopolysaccharides (LPS) were chosen as stimulators of cellular respiration. Cyanide, rotenone and diphenyleneiodonium (DPI) were chosen as inhibitors of cellular respiration. Here, we clearly demonstrated that oxygen consumption by endothelial cells can be measured accurately by EPR oximetry utilizing LiNc—BuO. The reliability of the method was established by examining the sensitivity of oxygen consumption by MAECs to various metabolic stimulators and inhibitors.

MATERIALS AND METHODS—Reagents Lithium 5,9,14,18,23,27,32,36-octa-n-butoxy-2,3-naphthalocyanine (LiNc—BuO) was used as a probe for measuring oxygen concentration in cellular suspensions using EPR spectroscopy. LiNc—BuO belongs to the class of crystalline internal spin probe (CRISP) particulates that we have recently synthesized for measuring oxygen concentration in cellular suspensions and tissues [119]. Menadione, DPI, LPS (*Escherichia coli* O128:B12), rotenone and potassium cyanide were purchased from Sigma Chemical Company (St. Louis, Mo.). Stock solutions (1 mM) of menadione, DPI, and rotenone were freshly prepared in dimethyl sulfoxide (DMSO) and used immediately. LPS was prepared as 1 mg/ml of sterile phosphatebuffered saline (PBS) and stored at −20° C. until use. KCN was prepared in distilled water and used immediately.

Endothelial cells MAECs used in this study were provided by Dr. Robert Auerbach at the University of Wisconsin, Madison, Wis. MAECs were cultured in DMEM containing 5% fetal bovine serum and antibiotics (penicillin-streptomycin) and maintained at 37° C. in a humidified atmosphere of 5% CO2/95% air. MAECs were grown to 90% confluence in T-75 flasks [120]. Cells from the flasks were detached by gentle scrapping with a Teflon cell scrapper along with the medium, cell density was determined, centrifuged at 1000×g at 4° C. for 10 minutes, and resuspended in a desired volume of PBS supplemented with glucose (0.1%) by gentle mixing for oximetry studies. Cell separation by trypsinization was avoided to keep the cell morphology and function in tact. Cells were cultured up to 6 passages and used in all the studies.

Cell suspensions were then treated immediately with various oxygen-modulating agents such as menadione, LPS, KCN, DPI and rotenone in aerobic conditions. After the addition of 5 μg of the oximetry probe (LiNc—BuO), cell suspensions were drawn into capillary tubes (20 μl), which was then sealed at both ends using Critoseal®. Care was taken to avoid entrapment of any air bubbles in side the capillary. Cell viability was assessed before and after the EPR measurements by Trypan blue exclusion method and found to be >95%.

EPR measurements The EPR measurements were carried out using a Bruker X-band (9.8 GHz) spectrometer (Bruker Instruments, Karlshrue, Germany) equipped with TM110 cavity. The cavity was rotated 90° so that the capillary tube filled with the cell suspension could be kept horizontally to avoid settling down of the cells. EPR spectra were acquired using custom-developed data acquisition software (SPEX). Unless mentioned otherwise, the EPR line-widths reported are peak-to-peak widths (.Bpp) of the first derivative spectra.

Calibration of LiNc—BuO oximetry The LiNc—BuO crystals were calibrated for EPR oximetry as follows: A small amount (~10 μg) of the probe was encapsulated in a 0.8 mm diameter gas-permeable Teflon tube (Zeus Industrial Products, Orangeburg, S.C., USA), both ends of the tube were sealed and the tube was inserted into a 3 mm quartz EPR tube with both the ends open. The EPR tube was placed into the TM110 microwave cavity (X-band) at the center of the active volume of the resonator. Premixed oxygen and nitrogen gases of known composition were flown through the EPR tube attached to a gas flow meter (Cole-Parmer, Vernon Hills, Ill., USA) and gas impermeable silicon tubing (NOX, Wilmad Lab Glasses, Buena, N.J.) All measurements were carried out after equilibrating the sample with the gas mixture 5 min. The flow rate of the gas mixture was maintained at 2 L/min. The total pressure inside the EPR tube was maintained at 760 mmHg (atmospheric pressure) by exposing the other end of the tube to the ambient atmosphere. A linear variation of line-width was observed as a function of partial pressure of oxygen ($pO_2$) as shown in FIG. 7.

Oxygen consumption measurements The OCRs were determined from $pO_2$ data as a function of time obtained from cell suspensions in a sealed capillary tube. The following expression was used to calculate the OCR and expressed as nmol/min/1×106 cells: OCR=m.á, where m is the slope of the $pO_2$ curve (in mmHg/min) and á is the solubility of oxygen in water (1.59 nmol/mmHg at 22° C.). OCR was expressed as nanomoles of oxygen/min/106 cells.

Data analysis All values are expressed as means±SD of 4 to 6 independent experiments. ANOVA and student's t-test were used for statistical analysis. Differences between groups were considered to be significant at $P<0.05$.

RESULTS—Effect of molecular oxygen on the EPR spectrum of LiNc—BuO The effect of molecular oxygen ($O_2$) on the EPR spectrum of LiNc—BuO is shown in FIG. 7. The LiNc—BuO exhibited a single EPR peak with peak-to-peak width of 210 mG under anoxic condition. The spectrum was broadened with a concomitant decrease in amplitude in presence of oxygen. FIG. 7 shows the width of the probe as a function of partial pressure of oxygen ($pO_2$). It was observed that the width increased linearly with $pO_2$ in the range 0-160 mmHg. The slope of the curve, which reflected the oxygen sensitivity of the probe to oxygen, was 8.5 mG/mmHg. Thus the probe apparently was capable of measuring oxygen tension to ~0.1 mmHg resolution in the physiological range.

Oxygen consumption measurements Typical time course data of $pO_2$ measured in suspensions of MAECs that were treated with various agents are shown in FIG. 8. The measurements were performed routinely up to 20 min in a closed volume of 20 µl of suspension containing 20,000 cells. The data showed a linear decrease of $pO_2$ over time in all cases. The OCR in untreated control cells was 3.07±0.48 nmol/min/106 cells. Cells treated with menadione and LPS showed increased rates of oxygen consumption while cells treated with DPI, KCN and rotenone showed complete inhibition of oxygen consumption.

Effect of menadione Menadione is a redox-cycler that uncouples oxidative phosphorylation. The effect of menadione on the oxygen consumption by MAECs was investigated in the dose range of 10-200 µM. The results are shown in FIG. 9. A significant increase in the OCR was observed when MAECs were treated with menadione (10 and 50 µM) whereas a decrease in the OCR was observed upon treatment of cells with higher concentration of menadione (100 and 200 µM). A decrease in the OCR at the higher concentration of menadione might be due to enhanced production of oxygen radicals, which apparently inhibited the mitochondrial respiration. An increase in the OCR when MAECs were treated with the lower concentrations of menadione might be due to its redox-cycling activity and uncoupling of oxidative phosphorylation.

Effect of lipopolysaccharide The effect of LPS (an endotoxin of bacterial origin) on the OCR in MAECs was studied (FIG. 10). Oxygen consumption by MAECs was measured immediately after treatment with LPS (10 and 20 µg/ml). As seen in FIG. 10, an increase in the OCR was observed in cells treated with 10 and 20 µg/ml of LPS. On the other hand, cells incubated for 2 h at 37° C. in presence of 10 and 20 µg/ml of LPS showed a decrease in the OCR which was not statistically significant compared to untreated cells. Thus, it appears that the effect of LPS on the oxygen consumption by MAECs was both dose- and time-dependent.

Effect of stimulators and inhibitors on the oxygen consumption rates FIG. 11 shows a comparison of the OCRs in MAECs with several stimulators and inhibitors of cellular respiration. As shown in the figure, menadione and LPS increased the OCRs. Measurements performed in presence of inhibitors of mitochondrial respiration, namely, KCN (100 µM), rotenone (100 µM) and DPI (a flavoprotein inhibitor, 100 µM) indicated that there was a complete inhibition of the OCR in MAECs.

DISCUSSION The results showed that the OCRs in MAECs can be measured accurately by EPR oximetry in a small volume suspension containing 20,000 cells. This was feasible by the utilization of LiNc—BuO particulate oximetry probe which has high sensitivity and higher resolution for the determination of oxygen concentration. The high sensitivity of the EPR line-width of LiNc—BuO (8.5 mG/mmHg) is particularly important for two reasons: (i) the oxygen consumption measurements in cell suspensions can be performed in a relatively shorter period (usually 10 min) as opposed to the electrode or optical techniques which require several hours [123] (ii) measurements can be performed in small volumes (10-20 µL) and with less number of cells, as has been demonstrated in the present work. Thus, any alterations in the OCR due to higher cell densities or to exposure of cells to varying concentration of oxygen for prolonged periods of time can be eliminated by this method.

The OCR of untreated control MAECs measured at 22° C. was 3.07 nmol/min/$10^6$ cells. While this value is in the range of values reported for similar cells by other techniques, there are some marked differences. For example, James et al. [121] used 15N-PDT, a soluble EPR oximetry probe that measures average dissolved oxygen concentration in intra- and extracellular space of the porcine aortic ECs, and reported an OCR of 0.13 nmol/min/106 cells. A higher OCR (1.45 nmol/min/106 cells) was reported by Kjellstorm et al. [124] in the rat pulmonary arterial endothelial cells using an oxyhemoglobin-based microrespirometric method. They also observed comparable values in ECs from the human umbilical cord veins, but a: significantly lower value in the bovine aortic ECs (0.3 nmol/min/106 cells). Motterlini et al. [123] reported a value of 1.00 nmol/min/106 cells in the cultured vascular ECs (0.5×106 cells/ml) obtained from the porcine thoracic aorta using an optical method based on the oxygen-dependent quenching of a phosphorescent probe. The disparity in the results might be due to several factors such as the differences in the origin of the cells, conditions of the incubation, as well as the presence or absence of serum, growth factors and hormones. Further, the differences in the detection techniques might also contribute to the measured values.

The rate of respiration in cells in suspension may depend on the ratio of oxygen to the cell density. Several studies have shown changes in cellular metabolism parallel to changes in the oxygen concentration in the suspension or to changes in the cell density [125]. The dependence of the OCR on oxygen concentration in the medium is usually evidenced by nonlinearity in the oxygen versus time curve. Absence of any departure from linearity in the oxygen consumption curve (FIG. 8) suggested that the cellular respiration by the MAECs, at the cell density used, was not altered due to depletion of oxygen in the medium. Motterlini et al. observed that the OCR of the porcine aortic ECs was dependent on the cell density, with the rate decreasing from 1.0 to 0.6 nmol/min/106 cells when cell density was increased from 0.5–4×$10^6$ cells/ml. However, we did not observe any significant change in the OCR of MAECs in the range of 0.5–4×$10^6$ cells/ml (data not shown), suggesting that the respiration rate was not affected by cell density in this range.

Endothelial cells are generally characterized with lower OCR when compared to other cells, e.g., smooth muscle cells, myocytes or Chinese hamster ovary cells. The lower consumption rate of the endothelial cells is attributed to the presence of fewer number of mitochondria in these cells [126]. The observation that cyanide (an inhibitor of complex III of the electron transport chain) and rotenone (an inhibitor of complex I) completely inhibited the consumption of oxygen suggested that the observed oxygen utilization in the untreated cells was primarily due to mitochondrial respiration. This is further confirmed by the inhibitory effect of DPI, which is a blocker of flavoprotein complex of NADPH oxidase and complex I of mitochondrial respiration.

Menadione is a redox cycler that uncouples oxidative phosphorylation in the mitochondria leading to increased oxygen consumption. It is also known to induce oxidative stress in cells by generating superoxide and other downstream oxidants in the mitochondria. This causes both structural and functional damage to mitochondria and membranes in cells. While the pro-oxidant activity of menadione may strongly depend on the intracellular oxygen availability, the deleterious effect of the oxidants leading to mitochondrial injury may impair cellular respiration. The results of the present study clearly established the involvement of the OCR on the concentration of menadione. At lower concentrations of menadione an increase in the consumption of oxygen was observed. A two-fold increase in the OCR was measured at 50 μM concentration of menadione. Since the measurements were performed immediately after the addition of the quinone, the increase in consumption might be attributed to the increased generation or induction of reactive oxygen species in addition to the enhancement of oxidative phosphorylation in the mitochondria. At concentrations higher than 50 μM, however, the OCRs were significantly less compared to the control values, suggesting that the normal mitochondrial respiration might be impaired due to damage caused by higher concentrations of the drug.

Endotoxemic sepsis is associated with inadequate tissue oxygenation and altered distribution of oxygen in different organs [127]. Dysfunction of vascular endothelium and consequent damage to vascular tissues are attributed to be the major determinants in organ dysfunction mediated by endotoxin. Several studies which investigated the possible impairment of oxygen utilization in vascular cells treated with endotoxin showed conflicting results. A recent study by James et al. [121] showed that the influence of endotoxin on the rate of oxygen utilization is very much dependent on the cell type. While the CHO and kidney cortex cells showed markedly decreased oxygen consumption after treatment with LPS, ECs did not show any response to LPS. However, more recently Motterlini et al. [123] showed a 46% decrease in the rate of oxygen consumption in the porcine aortic ECs that were exposed to 1 μg/ml LPS. Our results in MAECs, measured immediately after treatment with 10 μg/ml LPS, indicated a 34% increase in oxygen consumption. However, cells treated with similar concentration of LPS but measured after 2 h of incubation showed a 16% decrease in the OCR compared to untreated cells. The increase in consumption of oxygen during the first 20 min after treatment with LPS might be attributed to the oxidative burst of vascular NADPH oxidase. Recent studies have suggested that a phagocyte-type NADPH oxidase is a significant source of intracellular ROS in cardiovascular cells [128]. Proinflammatory mediators such as TNF-á are known to stimulate NADPH oxidase in endothelial cells [129]. The oxygen consumption was completely blocked by DPI, a known inhibitor of NADPH oxidase suggesting the LPS-induced oxidative burst in the ECs. We found a decrease in the rate of oxygen consumption after 2 h of incubation with LPS. This might be due to the inhibition of mitochondrial respiration by nitric oxide. LPS is known to simulate NO from iNOS [130]. The time required for the endogenous stimulation of iNOS is usually 2-4 h. Nitric oxide can potentially regulate cellular oxygen consumption by binding to the oxygenbinding site of cytochrome oxidase, resulting in reversible inhibition of mitochondrial respiration [131]. Higher concentrations of NO or its derivatives like peroxynitrite can also cause irreversible inhibition of respiration at multiple sites within mitochondria [132-134].

SUMMARY AND CONCLUSIONS

Oxygen consumption rates of MAECs in suspension were determined using EPR oximetry. The method utilized a microparticulate spin probe (LiNc—BuO) with a high sensitivity for oxygen, enabling accurate measurement of $pO_2$ in solution. We determined the effect of metabolic stimulators and inhibitors such as menadione, LPS, cyanide, rotenone, and DPI on the OCR. The measurements were performed in a volume of 20 μL containing 20,000 cells (cell density: 1×106 cells/ml) contained in a closed capillary tube. A linear decrease in $pO_2$ was observed as a function of time suggesting that the cellular respiration was independent of oxygen concentration in the medium. We observed an increase in oxygen consumption when MAECs were treated with menadione and LPS, whereas cyanide, rotenone and DPI inhibited oxygen consumption. In summary, we demonstrated that accurate measurements of cellular oxygen consumption can be performed in small volumes of cellular suspensions using microparticulate-based EPR oximetry.

Simultaneous Measurement of Oxygenation in Intracellular and Extracellular Compartments of Lung Microvascular Endothelial Cells A new technique is described for simultaneous determination of intra- and extracellular oxygen concentrations ($pO_2$) in bovine lung microvascular endothelial cells (BLMVECs) using electron paramagnetic resonance (EPR) oximetry. The method utilizes dual spin probes, one exclusively internalized in cells and the other placed extracellularly which are capable of reporting oxygenation simultaneously from the two distinct regions. The measurements were performed in BLMVEC suspensions of 20 μL volume containing 4,000 cells. The extracellular $pO_2$ was measured using a trityl EPR probe (TAM, 10 μM), a tricarboxylate anion, that stays exclusively in the extracellular space. The intracellular oxygen was measured using a pre-internalized particulate spin probe, lithium octa-n-butoxynaphthalocyanine (LiNc—BuO), which enables highly accurate and precise measurements of intracellular $pO_2$. Because there is a wide discrepancy in the reported values of cellular oxygenation by and large due to differences in the methods employed, we utilized the dual EPR probe technique to measure the oxygen gradient that apparently exists across the cell membrane. The intra- and extracellular $pO_2$ were 139±2.5 and 157±3.6 mmHg, respectively, for cells exposed to room air ($pO_2$: 159 mmHg). A fairly smaller gradient of oxygen was observed in cells exposed to 7.5% oxygen ($pO_2$: 57 mmHg). There was no significant difference in the intra- and extracellular $pO_2$) when cells were treated with either menadione (50 μM) or cyanide (100 M). In conclusion, this study confirms the feasibility of simultaneous and accurate measurements of intra-extracellular $pO_2$ using LiNc—BuO and TAM EPR oximetry probes.

Oxygen is an important modulator of cellular functions in both normal physiology and disease states. Cells respond to oxygen over a wide range of concentrations from anoxia to hyperoxia. Baseline metabolism and function typically occur in normoxic environments (30-90 mmHg of $O_2$) and can modulate differentiated cell functions [149]. Hyperoxic conditions often result in the generation of reactive oxygen species (ROS) that have been implicated in cell injury via lipid peroxidation and cytokine expression [139]. In lieu of such diversity in cellular responses to oxygen, the dynamics of tissue oxygenation, including the transport of oxygen and possible existence of oxygen gradient across the cell membrane needs to be measured accurately. Various methods such as manometry, photometry, mass spectrometry and polarography (Clark-type electrochemical) have been described to measure concentration and uptake of cellular oxygen [137, 138, 153, 159, 165]. The microelectrode technique, despite being used widely, has disadvantages as it consumes oxygen during measurement, apparently causes systematic error under very low oxygen concentrations, requires insertion into the tissues, disturbs the local environment and causes tissue damage [166, 167].

Although the determination of extracellular oxygen concentration in cell suspensions is straightforward, the measurement of intracellular $pO_2$ is complicated. There are a few methods available to accomplish this, for example, by insertion of an intracellular oxygen electrode into a single cell [167, 168] or by fluorescence quenching by $O_2$ following the cellular uptake of fluorescent probe, pyrenebutyric or 2-nitroimidazole (EF5) [136, 151]. Electron paramagnetic resonance (EPR) spectroscopy, coupled with the use of oxygen-sensitive spin probes, has become a potential technique for accurate and precise determination of oxygen concentrations in a variety of biological samples, including tissues and cells [141, 147, 154, 161, 170]. The technique, referred to as 'EPR oximetry', uses soluble molecular spin probes for the determination of dissolved oxygen concentration and particulate spin probes for targeted determination of local oxygen tension (partial pressure of oxygen, $pO_2$) in tissues and cells [144]. The particulate probes have unique advantages over the other EPR oximetry probes: (i) they report $pO_2$, which is a better parameter in a heterogeneous cellular system (ii) they do not consume oxygen (iii) they provide higher resolution at lower $pO_2$ and (iv) they possess greater stability in cells and tissues, so that, repeated measurements of oxygen tensions can be made for months without reintroduction of the probe. Hence, the particulate oximetry probe-coupled EPR spectroscopic determination of oxygen has advantages over the other methods of determination of oxygen in biological samples [137, 153, 159, 165]. A variety of particulate probes that possess many of these desirable properties are useful in studies in vitro to in vivo [144, 152]. Recently, we synthesized and characterized octa-n-butoxy-substituted naphthalocyanine neutral radical (LiNc—BuO), which exhibits marked advantages, especially with respect microwave power saturation, linear response to concentration of oxygen, dynamic measurement range and higher spin density [156]. We have demonstrated the application of this material by successfully internalizing into the lung microvascular endothelial cells in culture for measuring intracellular $pO_2$. The probe is capable of providing reliable measurements of intracellular $pO_2$ with 0.1 mmHg resolution and the measurements can be made in a single cell.

The aim of the present study was to demonstrate the accuracy and reliability of the EPR oximetry method for simultaneous measurement of intracellular $pO_2$ in bovine lung microvascular endothelial cells (BLMVECs) utilizing internalized particulates of LiNc—BuO and extracellular $pO_2$ using TAM. We have also measured the intracellular and extracellular $pO_2$ in these cells in presence of metabolic inhibitors such as menadione (50 µM) and potassium cyanide (100 EM). As we have previously demonstrated that the LiNc—BuO enables very accurate and reliable measurement of $pO_2$ in cellular suspensions, we envisioned that the measurements will provide accurate values of intracellular $pO_2$ that have not been possible with the other techniques. Further, we extended such measurements to smaller sample volume (20 µl) with 4,000 cells. We observed an intracellular $pO_2$ of 139 mmHg and extracellular $pO_2$ of 157 mmHg with an oxygen gradient of 18 mmHg under aerobic conditions. A gradient of 9 mmHg of oxygen (extra and intracellular $pO_2$ were 64 and 55 mmHg respectively) was observed when the cells were exposed to 7.5% oxygen. Menadione and potassium cyanide did not affect significantly the intra- and extracellular $pO_2$ levels.

Materials and Methods—Reagents Lithium 5,9,14,18,23,27,32,36-octa-n-butoxy-2,3-naphthalocyanine (LiNc—BuO) was used as a probe for measuring intracellular oxygen concentration by EPR spectroscopy. LiNc—BuO belongs to the class of crystalline internal spin probe (CRISP) particulates that we have recently reported for measuring oxygen concentration in cellular suspensions and tissues [156]. TAM was a gift from Nycomed Innovations (Malmo, Sweden). The EPR properties of TAM have been well characterized (1). Menadione and potassium cyanide were purchased from the Sigma Chemical Company (St. Louis, Mo.). Stock solutions (1 mM) of menadione and KCN were prepared freshly in dimethylsulfoxide and distilled water, respectively and used immediately. Minimum essential medium (MEM), fetal bovine serum and antibiotics were obtained from GIBCO-Invitrogen, CA.

Bovine Lung Microvascular Endothelial Cells (BLMVECs) Culture The BLMVECs used in this study were obtained from the VEC Technologies, Inc, New York. BLMVECs cultured in MEM were maintained in 75 mm flasks at 37° C. in a humidified atmosphere of 5% $CO_2$/95% air and grown to contact-inhibited monolayers with a typical cobblestone morphology [157]. Cells from each primary flask were detached with 0.05% trypsin, resuspended in fresh medium, and cultured in complete medium to 70% confluency for other studies. Cells from passages 10-14 were used in all the experiments.

Preparation of Particulates for Cell Culture Studies Microcrystalline Particulates of LiNc—BuO were suspended in complete MEM medium (10 mg/0.5 ml) and sonicated for 30 sec pulse for ten times on ice with a probe sonicator at a setting of 5. The particulate suspension was cooled for 1 min between two successive 30 sec bursts of sonication. At the end of sonication, the suspension was placed on ice for exactly 2 min to allow the heavier particulates to settle down at the bottom of the tube and the supernatant liquid was transferred to a separate tube for intracellular delivery. The solution contained fine particulates of LiNc—BuO with a particulate size <2 µm. All the preparations were carried out under sterile conditions.

Internalization of Particulates into Endothelial Cells BLMVECs, at 70% confluence (104 cells/35 mm dish), in 1 ml complete MEM were treated with 50 µl of LiNc—BuO particulate suspension that contained particulates of <2 µm prepared by procedure as described under Materials and Methods. The cells were maintained at 37° C. under 95% air/5% $CO_2$ environment. At 6 h intervals, for 72 h, cells were examined under light microscope for internalization of LiNc—BuO particulates. Upon confirming the particulate uptake by all the cells in a given dish after 48 h of exposure to particulates, the cells were washed 12 times with ice-cold MEM to remove unincorporated and extraneous particulates by gentle swirling and aspiration, scrapped in 1 ml of MEM, and centrifuged at 1000×g in a microcentrifuge for 10 min. The cell pellet was resuspended in MEM containing glucose (0.5 g per 500 ml), at a density of 2×105 cells/ml and used for EPR analysis. Cells after LiNc—BuO internalization and repeated washings were photographed under an inverted microscope while still adherent to the substratum of the 35 mm dish. Cell viability was assessed by light microscopy and Alamar Blue assay according to the manufacturer's recommendations. Cell separation by trypsinization was avoided to keep the cell morphology and function in tact.

A 20 μL volume of the cell suspension containing 4,000 cells and 10 μM TAM was drawn into a gas-permeable Teflon tube and subjected to EPR spectroscopy as described below. The measurements were also carried out with Menadione (50 μM) and KCN (100 μM). Cell viability was assessed before and after the EPR measurements by Trypan blue exclusion method and found to be >95%.

EPR Measurements The EPR measurements were carried out using a Bruker X-band (9.8 GHz) spectrometer (Bruker Instruments, Karlshrue, Germany) equipped with TM110 cavity. EPR spectral acquisitions were performed using custom-developed data acquisition software (SPEX) that was capable of fully automated data acquisition and processing. Unless otherwise mentioned, the EPR line-widths reported are peak-to-peak widths (.Bpp) of the first derivative spectra.

Calibration of LiNc—BuO and TAM Oximetry The LiNc—BuO crystals were calibrated for EPR oximetry as described earlier [156]. Measurements of the line width of LiNc—BuO after equilibration with a series of oxygen and nitrogen gas mixtures were performed. Calibration was performed over the oxygen concentration range (0-21%) with oxygen/nitrogen mixtures. A linear variation of line-width was observed as a function of partial pressure of oxygen ($pO_2$) in the entire range of 0-160 mmHg. Similarly, the calibration of TAM (10 μM) was also performed using different oxygen concentrations (0-21%). The oxygen-induced line-broadening (change in peak-peak width) of the signal was used to measure extracellular oxygen concentration. The line shape of the EPR signal was precisely simulated using a Lorentzian functions and the Lorentzian width was used to establish the calibration curve.

Simultaneous Measurements of LiNc—BuO and TAM Line-shapes LiNc—BuO and TAM were used as site specific oximetry probes to measure intra- and extracellular oxygen concentration, respectively. Both LiNc—BuO and TAM give a single-line EPR spectrum, whose amplitude (intensity) and width depend on the amount/concentration of the probe and oxygen, respectively. Since the g-factor of LiNc—BuO (g=2.0024) and TAM (g=2.0030) are slightly different, their spectra do not overlap completely and show a composite feature where the two peaks can be separated by computer-simulation (FIG. 12).

The LiNc—BuO absorption profile is characterized by 100% Lorentzian [156], while the TAM signal can be approximated to be Lorentzian under conditions of oxygen-induced broadening. Thus, the deconvolution requires a simple two-component Lorentzian fitting to the measured spectrum. We validated the faithfulness of the deconvolution by performing the simulation under different combination of oxygen broadening to the probes. The reproducibility was very good ($R2>0.99$) for non-zero oxygen concentrations. The line-shape of TAM was non-Lorentzian under anoxic conditions.

It should also be noted that there was no effect of TAM on the EPR spectrum of LiNc—BuO and vice versa, when the two probes were suspended in the same medium having physical contact. This suggests that the two probes can be used together. However, in our experiments the probes were distributed in different regions (intra- and extracellular) and hence, such a contact did not exist. The components were separated using PEAK FIT (SPSS, Chicago, Ill.) software and the intracellular and extracellular $pO_2$ were determined from the calibration curves of LiNc—BuO and TAM.

Data Analysis All values are expressed as mean±SD of 4 to 6 independent experiments. ANOVA and student's t-test were used for statistical analysis. Differences between groups were considered to be significant at $P<0.05$.

Results-Internalization of LiNc—BuO Crystals into BLM-VECs The light microscopy, as shown in FIG. 13, clearly showed within 18 h of BLMVECs treatment with LiNc—BuO particulates (<2 μm) in complete MEM, nearly 95% of the cells internalized the particulates in a 35 mm dish. The internalized particulates show no cytotoxicity up to 72 h as evidenced by the light microscopy and Alamar Blue cytotoxicity assay. At the time of measurements, the viability of the cells that internalized LiNc—BuO was >95% as studied with 0.4% Trypan blue exclusion method.

The mean spin density of the LiNc—BuO particulates internalized in a single cell was calculated in comparison with a standard solution of TAM to be $6\times10^{11}$ spins/cell. This sensitivity is greater than that offered by the X-band EPR spectrometer, which is typically better than $1\times10^{10}$ spins. Thus, one can measure EPR spectrum from a single cell that is internalized with the LiNc—BuO particulates.

Effect of Molecular Oxygen on the EPR Spectrum of LiNc—BuO and TAM FIG. 14 shows the width of the probe as a function of partial pressure of oxygen ($pO_2$) in the range 0 to 158 mmHg. It is observed that the width increases linearly with $pO_2$ in the range 0-160 mmHg. The slope of the curve, which reflects the oxygen sensitivity of the probe to oxygen, is 8.5 mG/mmHg. Thus the probe is capable of measuring oxygen tension to 0.1 mmHg resolution in the physiological range. Similarly, TAM exhibits a peak-to-peak width of 146 mG under the anoxic condition and the spectrum is broadened in the presence of oxygen. The oxygen sensitivity of this radical is 0.36 mG/mmHg. The line shape of the EPR signal obtained with simultaneous use of intracellular LiNc—BuO and extracellular TAM was simulated precisely using two Lorentzian functions and the Lorentzian width was used to measure $pO_2$ from the calibration curve.

Intra- and Extracellular Oxygen Concentrations The internalized BLMVECs (4,000 cells) mixed with TAM (10 μM) in a 20 μL volume of aerated solution, showed an oxygen gradient of 18 mmHg with an intracellular $pO_2$ of 139 mmHg and extracellular $pO_2$ of 157 mmHg (FIG. 15). A gradient of 9 mmHg of oxygen was observed when cells were exposed to 7.5% oxygen. Internalization of LiNc—BuO particulates into BLMVECs and the feasibility of accurate measurement of intracellular $pO_2$ were confirmed in cell lysates prepared by brief sonication (5×10 sec) at 4° C. The $pO_2$ measured in the lysate was 158 mmHg. This observation clearly indicated the internalization of particulate probe into BLMVECs and the existence of oxygen gradient between intra- and extracellular compartments. There was no significant change in $pO_2$ and oxygen gradient in cells treated with menadione (50 μM) or cyanide (100 μM) (FIG. 16).

Discussion Oxygen gradient in physiological systems plays an important role in both maintaining homeostasis and inducing cellular responses. Therefore, an accurate and a reliable method to determine its concentrations in cells and tissues is highly critical. Values of oxygen gradient in cells measured by various methods reported so far in the literature vary widely range from 1 to 40 μM [140, 142, 148, 160, 162-164]. This broad discrepancy apparently is due to technical difficulty associated with accurate measurement of intracellular oxygen concentration under physiological conditions. Using nitroxides and other agents, several new methods based on EPR oximetry technique have been developed to measure intracellular oxygen concentrations in cells [143, 145-147, 158]. The particulate probe-based EPR oximetry, used in the present study has many advantages over the other oximetry probe-based EPR spectroscopy and other widely used methods to measure intracellular $pO_2$. Some of the distinct and advantageous features of LiNc—BuO paramagnetic spin particulates are; their ability to give rise to single sharp and isotropic EPR spectrum characteristic with 100% Lorentzian shape, linear variation of line-width with $pO_2$, that is independent of particulate size and most importantly their ability to internalize in cells. We have taken advantage of these favorable characteristics of LiNc—BuO particulates, successfully internalized them into in BLMVECs and measured intracellular $pO_2$ using EPR spectroscopy.

The intra- and extracellular $pO_2$ measured by this technique in BLMVECs were 139 mmHg and 157 mmHg, respectively at room air with a gradient of 18 mmHg. This technique also revealed the existence of a small oxygen gradient of 9 mmHg at 7.5% ($pO_2$: 57 mmHg) oxygen (extra and intracellular $pO_2$ were 64 and 55 mmHg respectively). Similar finding was also observed by others [150]. This suggest that the cells possess different gradients when exposed to different oxygen concentration and a smaller gradient exist at lower oxygen concentrations. Santini et al. [158] used fusinite as an EPR oximetry probe to measure intracellular molecular oxygen in K56 (an erythroleukemic cell line) and A 431 (an epidermal carcinoma cell line) and demonstrated that menadione (200 μM) increased both intra- and extracellular $pO_2$ by 10-15%. But in our study, menadione (50 μM) did not alter intra and extracellular $pO_2$ in BLMVECs. This may be due to different experimental conditions, dose and different cell types used. Khan et al. [150] measured intra- and extracellular oxygen concentrations in CHO cells by EPR oximetry using 15N-PDT and LiPc as intra- and extracellular probes, respectively. The -extra- and intracellular oxygen concentrations observed in this study were 162 mmHg (1 μM of oxygen is equal to 0.714 mmHg in aqueous solution) and 129 mmHg at 150 mmHg and 38.5 and 34.2 mmHg at 35 mmHg of $pO_2$. Using this technique, they demonstrated that plasma membrane cholesterol is an important barrier in regulating the oxygen gradient across the cell membrane.

In our recent study, we used LiNc—BuO particulate probe and measured the rate of oxygen consumption in mouse aortic endothelial cells in presence of various stimulants and inhibitors of respiration [155] and also measured the $pO_2$ in normal and tumor tissues [156]. In comparison with other oximetry probes, the unique advantage of LiNc—BuO is to prepare particulates of nanometer size without compromising its EPR behavior and oxygen-sensing abilities. The smaller particulates can be internalized in a variety of cells for different applications. It is possible to measure the $pO_2$ from a single cells internalized with LiNc—BuO.

The intracellular molecular oxygen is critical in determining the cytoplasmic chemical/physical environment of the cell. The use of highly sensitive EPR probe like LiNc—BuO, capable of measuring intracellular $pO_2$ with a greater sensitivity offers advantages in biological EPR oximetry. The data presented in this study demonstrated that this novel EPR probe can be successfully employed for direct and efficient measurement of intracellular oxygen concentration with a sensitivity of 0.1 mmHg in all cell types. The cells internalized with LiNc—BuO can be used as an important tool to monitor oxidative cellular functions and to study the cellular responses under pathophysiological and toxicological conditions.

SUMMARY AND CONCLUSIONS

The intracellular oxygen concentration in BLMVECs was measured by internalizing oxygensensitive microparticulate spin probe (LiNc—BuO) using electron paramagnetic resonance oximetry. The method utilized a microparticulate spin probe (LiNc—BuO) with a high sensitivity for oxygen, enabling accurate measurement of intracellular $pO_2$ in BLMVECs. We also determined the extracellular oxygen concentration using another oxygen sensitive oximetry probe, TAM, simultaneously. The effect of agents which can alter oxygen concentration such as menadione and potassium cyanide on oxygen gradient was also studied. The measurements were performed in a volume of 20 μL containing 4000 cells ($2\times10^5$ cells/mL) in a gas permeable Teflon tube at room air and at 7.5% oxygen. The intracellular oxygen concentration in BLMVECs measured at room air by this technique was 194 μM and extracellular oxygen concentration was 220 μM with a gradient of 26 μM and a oxygen gradient of 16 μM was seen in cells exposed 7.5% oxygen. There was no significant difference in extra- and intracellular oxygen concentration during treatment with menadione and potassium cyanide. In summary, we demonstrated that the measurements of intracellular oxygen concentration and oxygen gradient can be successfully performed using microparticulate-based EPR oximetry with a fewer number of cells.

Crystal Structure of Li(BuO)$_8$Nc The crystal structure of Li(BuO)$_8$Nc was studied by X-ray powder diffraction (XRPD) analysis using a Bruker D8 diffractometer equipped with a Cu Kα ($\lambda$=1.5406 Å) radiation tube, an incident beam Ge monochromator, and a Braun linear position sensitive detector (PSD). The XRPD patterns were collected at room temperature varying the powder mounting conditions, angular step size, and counting time. Data were collected using a conventional flat plate sample holder, a zero-background silicon single crystal sample holder, and a spinning thin walled capillary. The various data sets were all fairly similar, suggesting that preferred orientation effects are not a significant problem. In the capillary mode a noticeable background was observed over 2θ range 15-30° due to the amorphous nature of the glass capillary, whereas in the flat plate mode the peak intensities fell off rapidly with (sin θ)/λ. Taking into account resolution and signal-to-noise, we elected to use a data set collected using a 1 mm diameter capillary for detailed analysis. This scan covered the 2θ range 2-40° using a step size of 0.0143470 and a counting time of 10 sec per step.

In order to determine the crystal symmetry and unit cell dimensions of Li(BuO)$_8$Nc, the autoindexing software package CRYSFIRE [171] was used. Peak positions of first 24 reflections were fitted using the program XFIT [172] and exported to CRYSFIRE suite. Among the separate subroutines included in CRYSFIRE, ITO12 [173] identified two triclinic structures of very similar cell dimensions, with figures of merit (M), [174] 22 and 19. The space group was assumed to be the centric system P-1 rather than P1, in light of the pronounced preference for the former space group among existing structures. Using the approximate cell parameters suggested by ITO12, peak intensities were extracted by the whole pattern fitting approach based on LeBail method [175] as implemented in the GSAS software suite [176]. The LeBail fit gave a $\chi^2$ value of 5.16, an $R_{wp}$ value of 0.0290, and refined cell parameters of a=17.087(1) Å, b=18.792(1) Å, c=14.191 (1) Å, α=113.577(6)°, β=109.771(5)°, γ=73.517(6)°, and volume=3871.5(5) Å. The number of formula units per unit cell could be determined as Z=2 (LiC$_{80}$H$_{88}$N$_8$O$_8$, f.w. 1296.54, ρ=1.113 g/cm$^3$) from packing considerations.

Following the autoindexing and whole pattern fitting stages, the molecular packing of Li(BuO)$_8$Nc was further studied by a global optimization approach implemented within DASH, [177] the details of which are described elsewhere [178]. The peak intensities were extracted using the Pawley method [179] implemented in DASH, although the lattice parameters were fixed at values determined in GSAS. Pawley refinement gave a profile $\chi^2$ ($\chi_{pro}^2$) value of 3.67 and a R$_{wp}$ value of 0.0776. The LeBail and Pawley fits are shown in the supplementary information. Structure determination proceeded by means of the simulated annealing algorithm provided in DASH using a starting model structure of Li(BuO)$_8$Nc molecule constructed using the 3D Sketcher included in Material Studio [180]. The internal geometry of Li(BuO)$_8$Nc molecule did not undergo further optimization, but the C—C or C—N bond lengths and the size of naphthalocyanine ring were examined and found to be very similar to those in metal naphthalocyaninates of nickel, copper, or zinc [181]. Since the number of atoms in the asymmetric unit, 185, exceeds the default values of DASH, which can handle up to 150 atoms in an asymmetric unit, the input structure was modified by removing all hydrogen atoms. The resulting molecular fragment consists of 96 atoms but still retains 93% mass of the original Li(BuO)$_8$Nc molecule (see FIG. 17).

Using the rigidity of the molecule as a chemical constraint, the crystal structure of Li(BuO)$_8$Nc molecule can be described by 3 positional variables and 3 independent rotational parameters. In addition, each of the eight n-butoxy chains has 4 conformational degrees of freedom, for a total of 32 unknown torsion angles. In a single simulated annealing run of DASH, 107 movements were made adjusting the above 38 variables to generate a theoretical pattern that best matches the experimental data. The initial 45 trial runs, in which no constraints were imposed, did not lead to a straightforward solution possibly because the structure has too many flexible bonds, the combinations of which cannot be thoroughly examined. However a careful examination of output structures revealed two favored regions for the position (center of mass) of the molecule, as shown in the plot of positional parameters from 20 output results with lowest $\chi_{pro}^2$ (see FIG. 18). Within both convergent groups, the orientations of naphthalocyanine rings differed only slightly among trials. The reproducible location and orientation of the naphthalocyanine ring suggests that the crystal structure adopts one of these two molecular packing arrangements; referred to as type-I for the group centered at (0.05, 0.03, 0.37) and type-II for the group centered at (0.44, 0.02, 0.15).

The results of the DASH structure solution attempts described in the preceding paragraph indicate that given the complexity of the molecule in question and the limited resolution of the X-ray diffraction data it is not possible to obtain a complete structure solution. However, there is a strong indication we can determine the approximate location and orientation of the napthalocyanine ring. To further investigate this assumption we attempted structure solution using simpler model structures in which the —OBu groups are replaced by —OC$_n$H$_{2n+1}$ (n=0, 1, 2, 3). Omission of all or part of the alkyl chains leaves 65% (—OH), 74% (—OMe), 83% (—OEt), and 91% (—OPr) of the total mass of the actual compound. While it is possible that this omission may mislead the structure solution process, we felt that omission of atoms that cannot be reliably located in the structure solution process may help to avoid falling into false minima with regard to the location and orientation of the napthalocyanine ring. It was observed that reducing the total number of conformational variables in this manner, leads to a significant improvement in the reproducibility of the simulated annealing process. It is noteworthy that the solutions from all four cases agreed well both in the position and orientation of the naphthalocyanine ring, with the type-II solution. The $\chi_{pro}^2$ values gradually increased with the decrease of the number of carbon atoms in the side chains: —OPr, ~170, —OEt, ~230, —OMe, ~260, and —OH, ~290. These results strongly suggest that the type-II model describes the molecular packing of the naphthalocyanine rings, and also that the alkoxy chains provide non-negligible contributions to the diffraction pattern.

In the subsequent step, we decided to fine-tune the stacking structure of Li(OBu)$_8$Nc by imposing constraints on the external degrees of freedom as obtained from above exploratory trials. The center of mass of Li(OBu)$_8$Nc was confined to a volume defined by $0.35 \leq x \leq 0.5$, $0 \leq y \leq 0.15$, $0.05 \leq z \leq 0.2$, and the quarternians, Qi (i=0, 1, 2, 3; $-1 \leq Qi \leq 1$), [182] were limited to have a width of 0.4, while the thirty two torsion angles were allowed to vary freely. From 10 trials under the above controlled condition, solutions were obtained with $\chi_{pro}^2$ values of 128.5-147.2. The positions and orientations of the rigid ring part were almost invariant according to the constraints, but the conformations of eight butoxy chains were rather featureless. Consequently, a meaningful pattern could not be ascertained. The various and irregular conformations of the butoxy chains must be responsible for the high and dispersed $\chi_{pro}^2$ values. The refinement profile for the best-fit result obtained with a $\chi_{pro}^2$ value of 128.5, is given in supplementary information.

At this stage it is instructive to consider the quality of the data and the solution, in a manner similar to that used in protein crystallography. The useful information in the diffraction data begins to die off at ~26° 2θ (see Supplementary information), which corresponds to a d-spacing of 3.4 Å. Consequently, it is futile to hope for a structure solution from this diffraction data that accurately reproduces the crystal structure with atomic resolution. A more realistic expectation would be to attempt to extract the molecular packing diagram of the planar naphthalocyanine rings. That would entail accurately fitting the diffraction pattern out to a d-spacing corresponding to the intermolecular spacing. In many metal naphthalocyaninates, the shortest interplanar distances are ~3.3 Å[181] but in the Li(OBu)$_8$Nc the butoxy chains are likely to increase the intermolecular spacing. Our results (described in more detail below) suggest that the napthalocyanine molecules are roughly 5 Å apart. Therefore, the information that we can hope to reliably extract from the diffraction pattern is contained in the 2θ range 3.2-18.6° (d>4.8 Å). Building on this premise we proceeded to analyze this low angle region of the diffraction pattern using the simulated annealing algorithms in DASH. The solution obtained possesses a very low $\chi_{pro}^2$ value of 24, and once again the type II model for the location and orientation of the naphthalocyanine ring was obtained. The refinement profile for 3.2-18.6° range is shown in FIG. 19. This result combined with the results using truncated alkoxy chains give compelling proof that the approximate molecular packing diagram corresponds to the type-II solution, while the type-I solution represents a false minimum that results from the failure to accurately determine the orientations of the n-butoxy chains. The high $\chi_{pro}^2$ value that is obtained from analysis of the entire pattern can be traced to the poor fit at higher 2θ region, where the coherence related to the orientation of the butoxy chains becomes increasingly important. Clearly there is some degree of order in the orientation of these chains, but the vast number of conformations that could be adopted prevents us from extracting this information. To obtain this information single crystal studies are probably necessary. Alternatively, energy minimization algorithms may be able to find the most favorable conformation given the dimensions of the unit cell and the approximate location of the napthalocyanine ring.

FIG. 20 shows the obtained crystal structure of Li(OBu)$_8$Nc viewed along the three crystallographic axes. It can be noted that the molecules are arranged to form infinite channels along a- and c-axes. These channels interpenetrate each other at an angle of 109.8°, which is nearly the same as the lattice angle, β. While the exact dimensions will be sensitive to the conformation of the n-butoxy groups, the cross-sectional dimensions of the channels are not smaller than 8.1×9 Å and 4.6×5.7 Å along a- and c-axes, respectively. The presence of large and interconnected voids in the crystal structure could allow facile diffusion of $O_2$ molecules, whose approximate size is 2.8×3.9 Å. This structural motif is likely to be crucial to the sensor activity of Li(OBu)$_8$Nc. The view along the b-axis (FIG. 20b) shows that the planar rings of the Li(OBu)$_8$Nc molecules are almost parallel to b-axis. Furthermore, it illustrates the columnar stacking of the molecules in a- and c-directions, which is responsible for the creation of channels. Within the columnar arrangements in both the directions, a dimer unit of Li(OBu)$_8$Nc molecules is formed. The molecules in the dimer are slightly glided away from the eclipsed conformation to have an interplanar distance of ~4.8 Å and a L—Li distance of 5.0 Å. Along the a-direction, the closest Li(OBu)$_8$Nc molecules from two neighboring dimers are separated by an interplanar distance of 9.4 Å and a L—Li distance of 13.5 Å. On the other hand, in the c-direction, the planar spacing between the dimers is almost identical to the intra-dimer spacing of ~4.8 Å, and the adjacent dimers are glided from each other to have a L—Li distance of 11.4 Å.

REFERENCES

[1] Kuppusamy, P.; Wang, P.; Chzhan, M.; Zweier, J. L. High resolution electron paramagnetic resonance imaging of biological samples with a single line paramagnetic label. *Magn Reson Med* 37:479-483; 1997.

[2] He, G.; Samouilov, A.; Kuppusamy, P.; Zweier, J. L. In vivo EPR imaging of the distribution and metabolism of nitroxide radicals in human skin. *J Magn Reson* 148:155-164; 2001.

[3] He, G.; Samouilov, A.; Kuppusamy, P.; Zweier, J. L. In vivo imaging of free radicals: applications from mouse to man. *Mol Cell Biochem* 234-235:359-367; 2002.

[4] Lurie, D. J.; Li, H.; Petryakov, S.; Zweier, J. L. Development of a PEDRI free-radical imager using a 0.38 T clinical MRI system. *Magn Reson Med* 47:181-186; 2002.

[5] Irani, K.; Xia, Y.; Zweier, J. L.; Sollott, S. J.; Der, C. J.; Fearon, E. R.; Sundaresan, M.; Finkel, T.; Goldschmidt-Clermont, P. J. Mitogenic signaling mediated by oxidants in Ras-transformed fibroblasts. *Science* 275:1649-1652; 1997.

[6] He, G.; Shankar, R. A.; Chzhan, M.; Samouilov, A.; Kuppusamy, P.; Zweier, J. L. Noninvasive measurement of anatomic structure and intraluminal oxygenation in the gastrointestinal tract of living mice with spatial and spectral EPR imaging. *Proc Natl Acad Sci USA* 96:4586-4591; 1999.

[7] Li, H.; Deng, Y.; He, G.; Kuppusamy, P.; Lurie, D. J.; Zweier, J. L. Proton electron double resonance imaging of the in vivo distribution and clearance of a triaryl methyl radical in mice. *Magn Reson Med* 48:530-534; 2002.

[8] Kuppusamy, P.; Shankar, R. A.; Roubaud, V. M.; Zweier, J. L. Whole body detection and imaging of nitric oxide generation in mice following cardiopulmonary arrest: detection of intrinsic nitrosoheme complexes. *Magn Reson Med* 45:700-707; 2001.

[9] Ilangovan, G.; Li, H.; Zweier, J. L.; Krishna, M. C.; Mitchell, J. B.; Kuppusamy, P. In vivo measurement of regional oxygenation and imaging of redox status in RIF-1 murine tumor: effect of carbogen-breathing. *Magn Reson Med* 48:723-730; 2002.

[10] Ilangovan, G.; Li, H.; Zweier, J. L.; Kuppusamy, P. In vivo measurement of tumor redox environment using EPR spectroscopy. *Mol Cell Biochem* 234-235:393-398; 2002.

[11] Ilangovan, G.; Manivannan, A.; Li, H.; Yanagi, H.; Zweier, J. L.; Kuppusamy, P. A naphthalocyanine-based EPR probe for localized measurements of tissue oxygenation. *Free Radic Biol Med* 32:139-147; 2002.

[12] Kuppusamy, P.; Wang, P.; Shankar, R. A.; Ma, L.; Trimble, C. E.; Hsia, C. J.;-Zweier, J. L. In vivo topical EPR spectroscopy and imaging of nitroxide free radicals and polynitroxyl-albumin. *Magn Reson Med* 40:806-811; 1998.

[13] Kuppusamy, P.; Wang, P.; Zweier, J. L.; Krishna, M. C.; Mitchell, J. B.; Ma, L.; Trimble, C. E.; Hsia, C. J. Electron paramagnetic resonance imaging of rat heart with nitroxide and polynitroxyl-albumin. *Biochemistry* 35:7051-7057; 1996.

[14] Zweier, J. L. Measurement of superoxide-derived free radicals in the reperfused heart. Evidence for a free radical mechanism of reperfusion injury. *J Biol Chem* 263:1353-1357; 1988.

[15] Chance, B.; Gao, G. In vivo detection of radicals in biological reactions. *Environ Health Perspect* 102 Suppl 10:29-32; 1994.

[16] Szabo, M. E.; Droy-Lefaix, M. T.; Doly, M. Direct measurement of free radicals in ischemic/reperfused diabetic rat retina. *Clin Neurosci* 4:240-245; 1997.

[17] Sankarapandi, S.; Zweier, J. L.; Mukherjee, G.; Quinn, M. T.; Huso, D. L. Measurement and characterization of superoxide generation in microglial cells: evidence for an NADPH oxidase-dependent pathway. *Arch Biochem Biophys* 353:312-321; 1998.

[18] Zweier, J. L.; Flaherty, J. T.; Weisfeldt, M. L. Direct measurement of free radical generation following reperfusion of ischemic myocardium. *Proc Natl Acad Sci USA* 84:1404-1407; 1987.

[19] Zweier, J. L.; Kuppusamy, P. Electron paramagnetic resonance measurements of free radicals in the intact beating heart: a technique for detection and characterization of free radicals in whole biological tissues. *Proc Natl Acad Sci USA* 85:5703-5707; 1988.

[20] Grill, H. P.; Zweier, J. L.; Kuppusamy, P.; Weisfeldt, M. L.; Flaherty, J. T. Direct measurement of myocardial free radical generation in an in vivo model: effects of postischemic reperfusion and treatment with human recombinant superoxide dismutase. *J Am Coll Cardiol* 20:1604-1611; 1992.

[21] Zweier, J. L.; Kuppusamy, P. In vivo EPR spectroscopy of free radicals in the heart. *Environ Health Perspect* 102 Suppl 10:45-51; 1994.

[22] Komarov, A.; Mattson, D.; Jones, M. M.; Singh, P. K.; Lai, C. S. In vivo spin trapping of nitric oxide in mice. *Biochem Biophys Res Commun* 195:1191-1198; 1993.

[23] Komarov, A. M.; Lai, C. S. Detection of nitric oxide production in mice by spin-trapping electron paramagnetic resonance spectroscopy. *Biochim Biophys Acta* 1272:29-36; 1995.

[24] Vanin, A. F.; Liu, X.; Samouilov, A.; Stukan, R. A.; Zweier, J. L. Redox properties of iron-dithiocarbamates and their nitrosyl derivatives: implications for their use as traps of nitric oxide in biological systems. *Biochim Biophys Acta* 1474:365-377; 2000.

[25] Kuppusamy, P.; Chzhan, M.; Vij, K.; Shteynbuk, M.; Lefer, D. J.; Giannella, E.; Zweier, J. L. Three-dimensional spectral-spatial EPR imaging of free radicals in the heart: a technique for imaging tissue metabolism and oxygenation. *Proc Natl Acad Sci USA* 91:3388-3392; 1994.

[26] Kuppusamy, P.; Chzhan, M.; Zweier, J. L. Development and optimization of three-dimensional spatial EPR imaging for biological organs and tissues. *J Magn Reson B* 106:122-130; 1995.

[27] Kuppusamy, P.; Chzhan, M.; Samouilov, A.; Wang, P.; Zweier, J. L. Mapping the spin-density and lineshape distribution of free radicals using 4D spectral-spatial EPR imaging. *J Magn Reson B* 107:116-125; 1995.

[28] Kuppusamy, P.; Wang, P.; Zweier, J. L. Three-dimensional spatial EPR imaging of the rat heart. *Magn Reson Med* 34:99-105; 1995.

[29] Kuppusamy, P.; Ohnishi, S. T.; Numagami, Y.; Ohnishi, T.; Zweier, J. L. Three-dimensional imaging of nitric oxide production in the rat brain subjected to ischemia-hypoxia. *J Cereb Blood Flow Metab* 15:899-903; 1995.

[30] Kuppusamy, P.; Wang, P.; Samouilov, A.; Zweier, J. L. Spatial mapping of nitric oxide generation in the ischemic heart using electron paramagnetic resonance imaging. *Magn Reson Med* 36:212-218; 1996.

[31] Kuppusamy, P.; Afeworki, M.; Shankar, R. A.; Coffin, D.; Krishna, M. C.; Hahn, S. M.; Mitchell, J. B.; Zweier, J. L. In vivo electron paramagnetic resonance imaging of tumor heterogeneity and oxygenation in a murine model. *Cancer Res* 58:1562-1568; 1998.

[32] Kuppusamy, P.; Shankar, R. A.; Zweier, J. L. In vivo measurement of arterial and venous oxygenation in the rat using 3D spectral-spatial electron paramagnetic resonance imaging. *Phys Med Biol* 43:1837-1844; 1998.

[33] Chzhan, M.; Kuppusamy, P.; Samouilov, A.; He, G.; Zweier, J. L. A tunable reentrant resonator with transverse orientation of electric field for in vivo EPR spectroscopy. *J Magn Reson* 137:373-378; 1999.

[34] Kuppusamy, P.; Li, H.; Ilangovan, G.; Cardounel, A. J.; Zweier, J. L.; Yamada, K.; Krishna, M. C.; Mitchell, J. B. Noninvasive imaging of tumor redox status and its modification by tissue glutathione levels. *Cancer Res* 62:307-312; 2002.

[35] Liebgott, T.; Li, H.; Deng, Y.; Zweier, J. L. Proton electron double resonance imaging (PEDRI) of the isolated beating rat heart. *Magn Reson Med* 50:391-399; 2003.

[36] Khan, N.; Shen, J.; Chang, T. Y.; Chang, C. C.; Fung, P. C.; Grinberg, O.; Demidenko, E.; Swartz, H. Plasma membrane cholesterol: a possible barrier to intracellular oxygen in normal and mutant CHO cells defective in cholesterol metabolism. *Biochemistry* 42:23-29; 2003.

[37] Gallez, B.; Mader, K. Accurate and sensitive measurements of pO(2) in vivo using low frequency EPR spectroscopy: how to confer biocompatibility to the oxygen sensors. *Free Radic Biol Med* 29:1078-1084; 2000.

[38] Velan, S. S.; Spencer, R. G.; Zweier, J. L.; Kuppusamy, P. Electron paramagnetic resonance oxygen mapping (EPROM): direct visualization of oxygen concentration in tissue. *Magn Reson Med* 43:804-809; 2000.

[39] Swartz, H. M.; Walczak, T. Developing in vivo EPR oximetry for clinical use. *Adv Exp Med Biol* 454:243-252; 1998.

[40] Zweier, J. L.; Chzhan, M.; Ewert, U.; Schneider, G.; Kuppusamy, P. Development of a highly sensitive probe for measuring oxygen in biological tissues. *J Magn Reson B* 105:52-57; 1994.

[41] Liu, K. J.; Gast, P.; Moussavi, M.; Norby, S. W.; Vahidi, N.; Walczak, T.; Wu, M.; Swartz, H. M. Lithium phthalocyanine: a probe for electron paramagnetic resonance oximetry in viable biological systems. *Proc Natl Acad Sci USA* 90:5438-5442; 1993.

[42] Ilangovan, G.; Zweier, J. L.; Kuppusamy, P. Electrochemical preparation and EPR studies of lithium phthalocyanine: Evaluation of the nucleation and growth mechanism and evidence for potential dependent phase formation. *J. Phy. Chem. B* 104:4047-4059; 2000.

[43] He, J.; Beghein, N.; Ceroke, P.; Clarkson, R. B.; Swartz, H. M.; Gallez, B. Development of biocompatible oxygen-permeable films holding paramagnetic carbon particles: evaluation of their performance and stability in EPR oximetry. *Magn Reson Med* 46:610-614; 2001.

[44] Gallez, B.; Jordan, B. F.; Baudelet, C. Microencapsulation of paramagnetic particles by pyrroxylin to preserve their responsiveness to oxygen when used as sensors for in vivo EPR oximetry. *Magn Reson Med* 42:193-196; 1999.

[45] Zho, F.; Neutra, M. R. Antigen delivery to mucosa-associated lymphoid tissues using liposomes as a carrier. *Biosci Rep* 22:355-369; 2002.

[46] Ahsan, F.; Rivas, I. P.; Khan, M. A.; Torres Suarez, A. I. Targeting to macrophages: role of physicochemical properties of particulate carriers—liposomes and microspheres—on the phagocytosis by macrophages. *J Control Release* 79:29-40; 2002.

[47] Moghimi, S. M.; Hunter, A. C.; Murray, J. C. Long-circulating and target-specific nanoparticles: theory to practice. *Pharmacol Rev* 53:283-318; 2001.

[48] Blau, S.; Jubeh, T. T.; Haupt, S. M.; Rubinstein, A. Drug targeting by surface cationization. *Crit. Rev Ther Drug Carrier Syst* 17:425-465; 2000.

[49] Barratt, G. M. Therapeutic applications of colloidal drug carriers. 3:163-171; 2000.

[50] Hnatyszyn, H. J.; Kossovsky, N.; Gelman, A.; Sponsler, E. Drug delivery systems for the future. *PDA J Pharm Sci Technol* 48:247-254; 1994.

[51] Zhou, F.; Huang, L. Liposome-mediated cytoplasmic delivery of proteins: an effective means of accessing the MHC class I-restricted antigen presentation pathway. *Immunomethods* 4:229-235; 1994.

[52] Drouillat, B.; Hillery, A. M.; Dekany, G.; Falconer, R.; Wright, K.; Toth, I. Novel liposaccharide conjugates for drug and peptide delivery. *J Pharm Sci* 87:25-30; 1998.

[53] Garcia-Chaumont, C.; Seksek, O.; Grzybowska, J.; Borowski, E.; Bolard, J. Delivery systems for antisense oligonucleotides. *Pharmacol Ther* 87:255-277; 2000.

[54] Ehrhardt, C.; Fiegel, J.; Fuchs, S.; Abu-Dahab, R.; Schaefer, U. F.; Hanes, J.; Lehr, C. M. Drug absorption by the respiratory mucosa: cell culture models and particulate drug carriers. *J Aerosol Med* 15:131-139; 2002.

[55] Takeuchi, H.; Yamamoto, H.; Kawashima, Y. Mucoadhesive nanoparticulate systems for peptide drug delivery. *Adv Drug Deliv Rev* 47:39-54; 2001.

[56] Kursa, M.; Walker, G. F.; Roessler, V.; Ogris, M.; Roedl, W.; Kircheis, R.; Wagner, E. Novel Shielded Transferrin-Polyethylene Glycol-Polyethylenimine/DNA Complexes for Systemic Tumor-Targeted Gene Transfer. *Bioconjug Chem* 14:222-231; 2003.

[57] dley, F. D. Nonviral gene therapy: the promise of genes as pharmaceutical products. *Hum Gene Ther* 6:1129-1144; 1995.

[58] M.; O'Hagan, D. T. Recent advances in vaccine adjuvants. *Pharm Res* 19:715-728; 2002.

[59] Kuppusamy, P., Wang, P., Samouilov, A., and Zweier, J. L. Spatial mapping of nitric oxide generation in the ischemic heart using electron paramagnetic resonance imaging. Magn Reson Med, 36: 212-218, 1996.

[60] Kuppusamy, P., Shankar, R. A., Roubaud, V. M., and Zweier, J. L. Whole body detection and imaging of nitric oxide generation in mice following cardiopulmonary arrest: detection of intrinsic nitrosoheme complexes. Magn Reson Med, 45: 700-707, 2001.

[61] Ilangovan, G., Li, H., Zweier, J. L., Krishna, M. C., Mitchell, J. B., and Kuppusamy, P. In vivo measurement of regional oxygenation and imaging of redox status in RIF-1 murine tumor: effect of carbogen-breathing. Magn Reson Med, 48: 723-730, 2002.

[62] Kuppusamy, P., Li, H., Ilangovan, G., Cardounel, A. J., Zweier, J. L., Yamada, K., Krishna, M. C., and Mitchell, J. B. Noninvasive imaging of tumor redox status and its modification by tissue glutathione levels. Cancer Res, 62: 307-312, 2002.

[63] Lewin, M., Carlesso, N., Tung, C. H., Tang, X. W., Cory, D., Scadden, D. T., and Weissleder, R. Tat peptide-derivatized magnetic nanoparticles allow in vivo tracking and recovery of progenitor cells. Nat Biotechnol, 18: 410-414, 2000

[64] Velan, S. S., Spencer, R. G., Zweier, J. L., and Kuppusamy, P. Electron paramagnetic resonance oxygen mapping (EPROM): direct visualization of oxygen concentration in tissue. Magn. Reson. Med., 43: 804-809, 2000.

[65] Muir, W. W.; Wellman, M. L. Hemoglobin solutions and tissue oxygenation. J Vet Intern Med 17:127-135; 2003.

[66] Vaupel, P.; Schlenger, K.; Knoop, C.; Hockel, M. Oxygenation of human tumors: evaluation of tissue oxygen distribution in breast cancers by computerized O2 tension measurements. Cancer Res 51:3316-3322; 1991.

[67] Kim, J. G.; Zhao, D.; Song, Y.; Constantinescu, A.; Mason, R. P.; Liu, H. Interplay of tumor vascular oxygenation and tumor pO2 observed using near-infrared spectroscopy, an oxygen needle electrode, and 19F MR pO2 mapping. J Biomed Opt 8:53-62; 2003.

[68] Laukemper-Ostendorf, S.; Scholz, A.; Burger, K.; Heussel, C. P.; Schmittner, M.; Weiler, N.; Markstaller, K.; Eberle, B.; Kauczor, H. U.; Quintel, M.; Thelen, M.; Schreiber, W. G. 19F-MRI of perflubron for measurement of oxygen partial pressure in porcine lungs during partial liquid ventilation. Magn Reson Med 47:82-89; 2002.

[69] Aboagye, E. O.; Maxwell, R. J.; Horsman, M. R.; Lewis, A. D.; Workman, P.; Tracy, M.; Griffiths, J. R. The relationship between tumour oxygenation determined by oxygen electrode measurements and magnetic resonance spectroscopy of the fluorinated 2-nitroimidazole SR-4554. Br J Cancer 77:65-70; 1998.

[70] Prasad, P. V.; Edelman, R. R.; Epstein, F. H. Noninvasive evaluation of intrarenal oxygenation with BOLD MRI. Circulation 94:3271-3275; 1996.

[71] Mason, R. P.; Rodbumrung, W.; Antich, P. P. Hexafluorobenzene: a sensitive 19F NMR indicator of tumor oxygenation. NMR Biomed 9:125-134; 1996.

[72] Krishna, M. C.; English, S.; Yamada, K.; Yoo, J.; Murugesan, R.; Devasahayam, N.; Cook, J. A.; Golman, K.; Ardenkjaer-Larsen, J. H.; Subramanian, S.; Mitchell, J. B. Overhauser enhanced magnetic resonance imaging for tumor oximetry: coregistration of tumor anatomy and tissue oxygen concentration. Proc Natl Acad Sci USA 99:2216-2221; 2002.

[73] Fan, X.; River, J. N.; Zamora, M.; Al-Hallaq, H. A.; Karczmar, G. S. Effect of carbogen on tumor oxygenation: combined fluorine-19 and proton MRI measurements.: Int J Radiat Oncol Biol Phys 54:1202-1209; 2002.

[74] Dunn, J. F.; O'Hara, J. A.; Zaim-Wadghiri, Y.; Lei, H.; Meyerand, M. E.; Grinberg, O. Y.; Hou, H.; Hoopes, P. J.; Demidenko, E.; Swartz, H. M. Changes in oxygenation of intracranial tumors with carbogen: a BOLD MRI and EPR oximetry study. J Magn Reson Imaging 16:511-521; 2002.

[75] Williams, B. B.; al Hallaq, H.; Chandramouli, G. V.; Barth, E. D.; Rivers, J. N.; Lewis, M.; Galtsev, V. E.; Karczmar, G. S.; Halpern, H. J. Imaging spin probe distribution in the tumor of a living mouse with 250 MHz EPR: correlation with BOLD MRI. Magn Reson Med 47:634-638; 2002.

[76] Swartz, H. M.; Clarkson, R. B. The measurement of oxygen in vivo using EPR techniques. Phys Med Biol 43:1957-1975; 1998.

[77] Ilangovan, G.; Li, H.; Zweier, J. L.; Kuppusamy, P. Electrochemical preparation and EPR studies of lithium phthalocyanine. 3. Measurements of oxygen concentration in tissues and biochemical reactions. J. Phys. Chem. B 105:5323-5330; 2001.

[78] Ilangovan, G.; Manivannan, A.; Li, H.; Yanagi, H.; Zweier, J. L.; Kuppusamy, P. A naphthalocyanine-based EPR probe for localized measurements of tissue oxygenation. Free Radic. Biol. Med. 32:139-147; 2002.

[79] Liu, K. J.; Gast, P.; Moussavi, M.; Norby, S. W.; Vahidi, N.; Walczak, T.; Wu, M.; Swartz, H. M. Lithium phthalocyanine: a probe for electron paramagnetic resonance oximetry in viable biological systems. Proc. Natl. Acad. Sci. USA 90:5438-5442; 1993.

[80] Elas, M.; Williams, B. B.; Parasca, A.; Mailer, C.; Pelizzari, C. A.; Lewis, M. A.; River, J. N.; Karczmar, G. S.; Barth, E. D.; Halpern, H. J. Quantitative tumor oxymetric images from 4D electron paramagnetic resonance imaging (EPRI): Methodology and comparison with blood oxygen level-dependent (BOLD) MRI. Magn Reson Med 49:682-691; 2003.

[81] Afeworki, M.; Miller, N. R.; Devasahayam, N.; Cook, J.; Mitchell, J. B.; Subramanian, S.; Krishna, M. C. Preparation and EPR studies of lithium phthalocyanine radical as an oxymetric probe. Free Radic Biol Med 25:72-78; 1998.

[82] James, P. E.; Grinberg, O. Y.; Goda, F.; Panz, T.; O'Hara, J. A.; Swartz, H. M. Gloxy: an oxygen-sensitive coal for accurate measurement of low oxygen tensions in biological systems. Magn Reson Med 38:48-58; 1997.

[83] Nakashima, T.; Goda, F.; Jiang, J.; Shima, T.; Swartz, H. M. Use of EPR oximetry with India ink to measure the pO2 in the liver in vivo in mice. Magn Reson Med 34:888-892; 1995.

[84] Turek, P.; Petit, P.; Andre, J. J.; Simon, J.; Even, R.; Boudjema, B.; Guillaud, G.; Maitrot, M. A New Series of Molecular Semiconductors—Phthalocyanine Radicals. J. Am. Chem. Soc. 109:5119-5122; 1987.

[85] Ilangovan, G.; Zweier, J. L.; Kuppusamy, P. Electrochemical preparation and EPR studies of lithium phthalocyanine: Evaluation of the nucleation and growth mechanism and evidence for potential-dependent phase formation. J. Phys. Chem. B 104:4047-4059; 2000.

[86] Ilangovan, G.; Zweier, J. L.; Kuppusamy, P. Electrochemical preparation and EPR studies of lithium phthalocyanine. Part 2: Particle-size-dependent line broadening by molecular oxygen and its implications as an oximetry probe. J. Phys. Chem. B 104:9404-9410; 2000.

[87] Manivannan, A.; Yanagi, H.; Ilangovan, G.; Kuppusamy, P. Lithium naphthalocyanine as a new molecular radical

[88] Turek, P.; Andre, J. J.; Giraudeau, A.; Simon, J. Preparation and study of a lithium phthalocyanine radical—optical and magnetic—properties. Chem. Phys. Lett. 134: 471-476; 1987.

[89] Bonnemain, B. Superparamagnetic agents in magnetic resonance imaging: physicochemical characteristics and clinical applications. A review. J Drug Target 6:167-174; 1998.

[90] Wang, Y. X.; Hussain, S. M.; Krestin, G. P. Superparamagnetic iron oxide contrast agents: physicochemical characteristics and applications in MR imaging. Eur Radiol 11:2319-2331; 2001.

[91] Frank, J. A.; Zywicke, H.; Jordan, E. K.; Mitchell, J.; Lewis, B. K.; Miller, B.; Bryant, L. H., Jr.; Bulte, J. W. Magnetic intracellular labeling of mammalian cells by combining (FDA-approved) superparamagnetic iron oxide MR contrast agents and commonly used transfection agents. Acad Radiol 9 Suppl 2:S484-487; 2002.

[92] Hinds, K. A.; Hill, J. M.; Shapiro, E. M.; Laukkanen, M. O.; Silva, A. C.; Combs, C. A.; Varney, T. R.; Balaban, R. S.; Koretsky, A. P.; Dunbar, C. E. Highly efficient endosomal labeling of progenitor and stem cells with large magnetic particles allows magnetic resonance imaging of single cells. Blood; 2003.

[93] Bulte, J. W.; Douglas, T.; Witwer, B.; Zhang, S. C.; Lewis, B. K.; van Gelderen, P.; Zywicke, H.; Duncan, I. D.; Frank, J. A. Monitoring stem cell therapy in vivo using magnetodendrimers as a new class of cellular MR contrast agents. Acad Radiol 9 Suppl 2:S332-335; 2002.

[94] Vahidi, N.; Clarkson, R. B.; Liu, K. J.; Norby, S. W.; Wu, M.; Swartz, H. M. In vivo and in vitro EPR oximetry with fusinite: a new coal-derived, particulate EPR probe. Magn Reson Med 31:139-146; 1994.

[95] Gallez, B.; Debuyst, R.; Dejehet, F.; Liu, K. J.; Walczak, T.; Goda, F.; Demeure, R.; Taper, H.; Swartz, H. M. Small particles of fusinite and carbohydrate chars coated with aqueous soluble polymers: preparation and applications for in vivo EPR oximetry. Magn Reson Med 40:152-159; 1998.

[96] Zweier, J. L.; Chzhan, M.; Ewert, U.; Schneider, G.; Kuppusamy, P. Development of a highly sensitive probe for measuring oxygen in biological tissues. J Magn Reson B 105:52-57; 1994.

[97] Kuppusamy, P.; Li, H.; Ilangovan, G.; Cardounel, A. J.; Zweier, J. L.; Yamada, K.; Krishna, M. C.; Mitchell, J. B. Noninvasive imaging of tumor redox status and its modification by tissue glutathione levels. Cancer Res 62:307-312; 2002.

[98] Probe for targeted oximetry in tissues 26 34. Pandian, R. P.; Zweier, J. L.; Kuppusamy, P. Magnetic and structural characterization of octabutoxy-substituted lithium naphathalocyanine crystals. J. Mag. Mag. Mater.; To be submitted.

[99] Gallez, B.; Jordan, B. F.; Baudelet, C. Microencapsulation of paramagnetic particles by pyrroxylin to preserve their responsiveness to oxygen when used as sensors for in vivo EPR oximetry. Magn. Reson. Med. 42:193-196; 1999.

[100] Goda, F.; Liu, K. J.; Walczak, T.; O'Hara, J. A.; Jiang, J.; Swartz, H. M. In vivo oximetry using EPR and India ink. Magn. Reson. Med. 33:237-245; 1995.

[101] Liu, K. J.; Miyake, M.; James, P. E.; Swartz, H. M. Separation and enrichment of the active component of carbon-based paramagnetic materials for use in EPR oximetry. J. Magn. Reson. 133:291-298; 1998.

[102] Atsarkin, V. A.; Demidov, V. V.; Vasneva, G. A.; Dzheparov, F. S.; Ceroke, P. J.; Odintsov, B. M.; Clarkson, R. B. Mechanism of oxygen response in carbon-based sensors. J Magn Reson 149:85-89; 2001.

[103] He, J.; Beghein, N.; Ceroke, P.; Clarkson, R. B.; Swartz, H. M.; Gallez, B. Development of biocompatible oxygen-permeable films holding paramagnetic carbon particles: evaluation of their performance and stability in EPR oximetry. Magn Reson Med 46:610-614; 2001.

[104] Jiang, H.; Beghei, N.; Clarkson, R. B.; Swartz, H. M.; Galle, B. Microencapsulation of carbon particles used as oxygen sensors in EPR oximetry to stabilize their responsiveness to oxygen in vitro and in vivo. Phys Med Biol 46:3323-3329; 2001.

[105] Turetschek, K.; Preda, A.; Floyd, E.; Shames, D. M.; Novikov, V.; Roberts, T. P.; Wood, J. M.; Fu, Y.; Carter, W. O.; Brasch, R. C. MRI monitoring of tumor response following angiogenesis inhibition in an experimental human breast cancer model. Eur J Nucl Med Mol Imaging 30:448-455; 2003.

[106] Kooi, M. E.; Cappendijk, V. C.; Cleutjens, K. B.; Kessels, A. G.; Kitslaar, P. J.; Borgers, M.; Frederik, P. M.; Daemen, M. J.; van Engelshoven, J. M. Accumulation of ultrasmall superparamagnetic particles of iron oxide in human atherosclerotic plaques can be detected by in vivo magnetic resonance imaging. Circulation 107:2453-2458; 2003.

[107] Ruehm, S. G.; Corot, C.; Vogt, P.; Cristina, H.; Debatin, J. F. Ultrasmall superparamagnetic iron oxide-enhanced MR imaging of atherosclerotic plaque in hyperlipidemic rabbits. Acad Radiol 9 Suppl 1:S143-144; 2002.

[108] D. J. Pinsky, S. F. Yan, C. Lawson, Y. Naka, J. X. Chen, E. S. Connolly, Jr., D. M. Stern, Semin Cell Biol 6 (1995) 283-294.

[109] G. L. Semenza, Annu Rev Cell Dev Biol 15 (1999) 551-578.

[110] N. C. Gonzalez, J. G. Wood, Adv Exp Med Biol 502 (2001) 39-60.

[111] N. L. Parinandi, M. A. Kleinberg, P. V. Usatyuk, R. J. Cummings, A. Pennathur, A. J. Cardounel, J. L. Zweier, J. G. Garcia, V. Natarajan, Am J Physiol Lung Cell Mol Physiol 284 (2003) L26-38.

[112] J. M. Vanderkooi, M. Erecinska, I. A. Silver, Am J Physiol 260 (1991) C1131-1150.

[113] K. J. Liu, P. Gast, M. Moussavi, S. W. Norby, N. Vahidi, T. Walczak, M. Wu, H. M. Swartz, Proc. Natl. Acad. Sci. USA 90 (1993) 5438-5442.

[114] G. Ilangovan, A. Manivannan, H. Li, H. Yanagi, J. L. Zweier, P. Kuppusamy, Free Radic. Biol. Med. 32 (2002) 139-147.

[115] P. E. James, O. Y. Grinberg, F. Goda, T. Panz, J. A. O'Hara, H. M. Swartz, Magn Reson Med 38 (1997) 48-58.

[116] T. Nakashima, F. Goda, J. Jiang, T. Shima, H. M. Swartz, Magn Reson Med 34 (1995) 888-892.

[117] N. Vahidi, R. B. Clarkson, K. J. Liu, S. W. Norby, M. Wu, H. M. Swartz, Magn Reson Med 31 (1994) 139-146.

[118] J. L. Zweier, M. Chzhan, U. Ewert, G. Schneider, P. Kuppusamy, J Magn Reson B 105 (1994) 52-57.

[119] R. P. Pandian, N. L. Parinandi, G. Ilangovan, J. L. Zweier, P. Kuppusamy, Free Radic. Biol. Med. (2003) (in press).

[120] M. Bastaki, E. E. Nelli, P. Dell'Era, M. Rusnati, M. P. Molinari-Tosatti, S. Parolini, R. Auerbach, L. P. Ruco, L. Possati, M. Presta, Arterioscler Thromb Vasc Biol 17 (1997) 454-464.

[121] P. E. James, S. K. Jackson, O. Y. Grinberg, H. M. Swartz, Free Radic Biol Med 18 (1995) 641-647.

[122] S. P. Bruttig, W. L. Joyner, J Cell Physiol 116 (1983) 173-180.

[123] R. Motterlini, H. Kerger, C. J. Green, R. M. Winslow, M. Intaglietta, Am J Physiol 275 (1998) H776-782.

[124] B. T. Kjellstrom, P. Ortenwall, B. Risberg, J Cell Physiol 132 (1987) 578-580.

[125] R. Steinlechner-Maran, T. Eberl, M. Kunc, R. Margreiter, E. Gnaiger, Am J Physiol 271 (1996) C2053-2061.

[126] A. Dobrina, F. Rossi, Biochim Biophys Acta 762 (1983) 295-301.

[127] P. B. Anning, M. Sair, C. P. Winlove, T. W. Evans, Am J Respir Crit. Care Med 159 (1999) 1710-1715.

[128] K. K. Griendling, D. Sorescu, M. Ushio-Fukai, Circ Res 86 (2000) 494-501.

[129] R. S. Frey, A. Rahman, J. C. Kefer, R. D. Minshall, A. B. Malik, Circ Res 90 (2002) 1012-1019.

[130] S. M. Morris, Jr., T. R. Billiar, Am J Physiol 266 (1994) E829-839.

[131] V. Borutaite, A. Matthias, H. Harris, S. Moncada, G. C. Brown, Am J Physiol Heart Circ Physiol 281 (2001) H2256-2260.

[132] R. Radi, M. Rodriguez, L. Castro, R. Telleri, Arch Biochem Biophys 308 (1994) 89-95.

[133] I. Lizasoain, M. A. Moro, R. G. Knowles, V. Darley-Usmar, S. Moncada, Biochem J 314 (Pt 3) (1996) 877-880.

[134] E. Clementi, G. C. Brown, M. Feelisch, S. Moncada, Proc Natl Acad Sci USA 95 (1998) 7631-7636.

[135] Ardenkjaer-Larsen J H, Laursen I, Leunbach I, Ehnholm G, Wistrand L G, Petersson J S, and Golman K. EPR and DNP properties of certain novel single electron contrast agents intended for oximetric imaging. J Magn Reson 133: 1-12, 1998.

[136] Benson D M, Knopp J A, and Longmuir I S. Intracellular oxygen measurements of mouse liver cells using quantitative fluorescence video microscopy. Biochim Biophys Acta 591: 187-197, 1980.

[137] Chapman K R, Liu F L, Watson R M, and Rebuck A S. Conjunctival oxygen tension and its relationship to arterial oxygen tension. J Clin Monit 2: 100-104, 1986.

[138] Dahl B T, Kiaer T, and Lund B. Measurement of bone cell metabolism in vitro using mass spectrometry. Calcif Tissue Int 50: 290-292, 1992.

[139] D'Angio C T, and Finkelstein J N. Oxygen regulation of gene expression: a study in opposites. Mol Genet Metab 71: 371-380, 2000.

[140] Grinberg O Y, James P E, and Swartz H M. Are there significant gradients of pO2 in cells? Adv Exp Med Biol 454: 415-423, 1998.

[141] He G, Shankar R A, Chzhan M, Samouilov A, Kuppusamy P, and Zweier J L. Noninvasive measurement of anatomic structure and intraluminal oxygenation in the gastrointestinal tract of living mice with spatial and spectral EPR imaging. Proc Natl Acad Sci USA 96: 4586-4591, 1999.

[142] Hu H, Sosnovsky G, and Swartz H M. Simultaneous measurements of the intra- and extra-cellular oxygen concentration in viable cells. Biochim Biophys Acta 1112: 161-166, 1992.

[143] Hu H P, Sosnovsky G, Li S W, Rao N U, Morse P D, 2nd, and Swartz H M. Development of nitroxides for selective localization inside cells. Biochim Biophys Acta 1014: 211-218, 1989.

[144] Ilangovan G, Manivannan A, Li H, Yanagi H, Zweier J L, and Kuppusamy P. A naphthalocyanine-based EPR probe for localized measurements of tissue oxygenation. Free Radic Biol Med 32: 139-147, 2002.

[145] Inoue M, Utsumi H, and Kirino Y. A comparative ESR study of some paramagnetic materials as probes for the noninvasive measurement of dissolved oxygen in biological systems. Chem Pharm Bull (Tokyo) 42: 2346-2348, 1994.

[146] James P E, Grinberg O Y, Michaels G, and Swartz H M. Intraphagosomal oxygen in stimulated macrophages. J Cell Physiol 163: 241-247, 1995.

[147] James P E, Jackson S K, Grinberg O Y, and Swartz H M. The effects of endotoxin on oxygen consumption of various cell types in vitro: an EPR oximetry study. Free Radic Biol Med 18: 641-647, 1995.

[148] Jones D P, and Kennedy F G. Intracellular $O_2$ gradients in cardiac myocytes. Lack of a role for myoglobin in facilitation of intracellular O2 diffusion. Biochem Biophys Res Commun 105: 419-424, 1982.

[149] Jungermann K, and Kietzmann T. Oxygen: modulator of metabolic zonation and disease of the liver. Hepatology 31: 255-260, 2000.

[150] Khan N, Shen J, Chang T Y, Chang C C, Fung P C, Grinberg O, Demidenko E, and Swartz H. Plasma membrane cholesterol: a possible barrier to intracellular oxygen in normal and mutant CHO cells defective in cholesterol metabolism. Biochemistry 42: 23-29, 2003.

[151] Koch C J. Measurement of absolute oxygen levels in cells and tissues using oxygen sensors and 2-nitroimidazole EF5. Methods Enzymol 352: 3-31, 2002.

[152] Kuppusamy P, Afeworki M, Shankar R A, Coffin D, Krishna M C, Hahn S M, Mitchell J B, and Zweier J L. In vivo electron paramagnetic resonance imaging of tumor heterogeneity and oxygenation in a murine model. Cancer Res 58: 1562-1568, 1998.

[153] Marshall R S, Koch C J, and Rauth A M. Measurement of low levels of oxygen and their effect on respiration in cell suspensions maintained in an open system. Radiat Res 108: 91-101, 1986.

[154] Morse P D, 2nd, and Swartz H M. Measurement of intracellular oxygen concentration using the spin label TEMPOL. Magn Reson Med 2: 114-127, 1985.

[155] Pandian R P, Kutala V K, Parinandi N, and Kuppusamy P. Measurement of cellular oxygen consumption using a microparticulate oximetry probe. 2003 (in preparation).

[156] Pandian R P, Parinandi N L, Ilangovan G, Zweier J L, and Kuppusamy P. Novel particulate spin probe for targeted determination of oxygen in cells and tissues. Free Radic Biol Med, 2003 (communicated).

[157] Roy S, Parinandi N, Zeigelstein R, Hu Q, Pei Y, Travers J B, and Natarajan V. Hyperoxia alters phorbol ester-induced phospholipase d activation in bovine lung microvascular endothelial cells. Antioxid Redox Signal 5: 217-228, 2003.

[158] Santini M T, Morelli G, Fattorossi A, Malorni W, Rainaldi G, and Indovina P L. The oxidizing agent menadione induces an increase in the intracellular molecular oxygen concentration in K562 and A431 cells: direct measurement using the new paramagnetic EPR probe fusinite. Free Radic Biol Med 20: 915-924, 1996.

[159] Shibata M, Ichioka S, Ando J, and Kamiya A. Microvascular and interstitial PO(2) measurements in rat skeletal muscle by phosphorescence quenching. J Appl Physiol 91: 321-327, 2001.

[160] Swartz H M. Measurements of intracellular concentrations of oxygen: experimental results and conceptual implications of an observed gradient between intracellular and extracellular concentrations of oxygen. Adv Exp Med Biol 345: 799-806, 1994.

[161] Swartz H M, Bacic G, Friedman B, Goda F, Grinberg O, Hoopes P J, Jiang J, Liu K J, Nakashima T, O'Hara J, and et al. Measurements of pO2 in vivo, including human subjects, by electron paramagnetic resonance. Adv Exp Med Biol 361: 119-128, 1994.

[162] Takahashi E, Endoh H, and Doi K. Intracellular gradients of O2 supply to mitochondria in actively respiring single cardiomyocyte of rats. Am J Physiol 276: H718-724, 1999.

[163] Takahashi E, Sato K, Endoh H, Xu Z L, and Doi K. Direct observation of radial intracellular pO2 gradients in a single cardiomyocyte of the rat. Am J Physiol 275: H225-233, 1998.

[164] Tamura M, Oshino N, Chance B, and Silver I A. Optical measurements of intracellular oxygen concentration of rat heart in vitro. Arch Biochem Biophys 191: 8-22, 1978.

[165] Taylor J, and Deutsch C. 19F-nuclear magnetic resonance: measurements of [O2] and pH in biological systems. Biophys J 53: 227-233, 1988.

[166] Vanderkooi J M, Erecinska M, and Silver I A. Oxygen in mammalian tissue: methods of measurement and affinities of various reactions. Am J Physiol 260: C1131-1150, 1991.

[167] Whalen W J. Intracellular oxygen microelectrodes. Adv Exp Med Biol 37A: 17-22, 1973.

[168] Whalen W J, Riley J, and Nair P. A microelectrode for measuring intracellular pO2. J Appl Physiol 23: 798-801, 1967.

[169] Wind R A, and Ardenkjaer-Larsen J H. 1H DNP at 1.4 T of water doped with a triarylmethyl-based radical. J Magn Reson 141: 347-354, 1999.

[170] Zweier J L, Chzhan M, Ewert U, Schneider G, and Kuppusamy P. Development of a highly sensitive probe for measuring oxygen in biological tissues. J Magn Reson B 105: 52-57, 1994.

[171] CRYSFIRE was written by R. Shirley. Academic users can obtain this software free of charge at http://www.ccp14.ac.uk/tutorial/crys/index.html http://www.ccp14.ac.uk/tutorial/tutorial.htm.

[172] XFIT was written by R. W. Cheary and A. A. Coelho. Academic users can obtain this software free of charge at http://www.ccp14.ac.uk/tutorial/xfit-95/xfit.htm.

[173] Visser, J. W. *J. Appl. Cryst.* 1969, 2, 89.

[174] de Wolff, P. M. *J. Appl. Cryst.* 1968, 1, 108.

[175] LeBail, A.; Duroy, H.; Fourquet, J. L. *Mater. Res. Bull.* 1988, 23, 447.

[176] Larson, A. C.; von Dreele, R. B. *General Structure Analysis System*; Los Alamos National Laboratory Report LAUR 86-748, 1994.

[177] DASH was written by W. I. F. David and K. Shankland, and can be purchased from the Cambridge Crystallographic Data Centre, see www.ccdc.cam.ac.uk for more details.

[178] David, W. I. F.; Shankland, K.; Shankland, N. *Chem. Commun.* 1998, 931.

[179] Pawley, G. S. *J. Appl. Cryst.* 1981, 14, 357.

[180] Material Studio is a product by Accelrys Inc. For purchase, see http://www.accelrys.com/materials/

[181] Morishige, K.; Araki, K. *J. Chem. Soc., Dalton Trans.* 1996, 4303.

[182] Leach, A. R., Ed. *Molecular Modeling: Principles and Applications*; Addison Wesley Lonman Ltd:, 1996.

The invention claimed is:

1. A particulate probe comprising a lithium phthalocyanine derivative of formula 4 or a radical thereof:

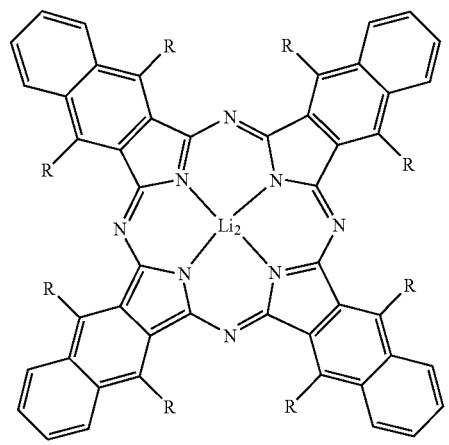

[4]

wherein R is selected from the group consisting of $O(CH_2)_nCH_3$, $S(CH_2)_nCH_3$, $O(CH_2)_nCH_2OH$, $O(CH_2)_nCH_2NH_2$, $O(CH_2)_nCH_2SH$, and combinations thereof; and n is from 1 to 6.

2. The particulate probe of claim 1, wherein the particulate probe is a nanoparticulate probe or a microparticulate probe.

3. The particulate probe of claim 2 wherein the particulate probe has a size of up to 10 microns.

4. The particulate probe of claim 3 wherein the particulate probe has a size of from 0.22 microns to 10 microns.

5. The particulate probe of claim 3 wherein the particulate probe has a size of less than 0.22 microns.

6. The particulate probe of claim 1 wherein the particulate probe has been derivatized to be a magnetic resonance imaging (MRI) probe.

7. The particulate probe of claim 1 wherein the particulate probe has been derivatized to be an electron spin resonance (ESR) probe.

8. The particulate probe of claim 1 wherein the particulate probe has been derivatized to be an electron paramagnetic resonance (EPR) probe.

9. The particulate probe of claim 1 wherein the particulate probe has been derivatized to be an electron paramagnetic resonance imaging (EPRI) probe.

10. The particulate probe of claim 1 wherein the particulate probe has been derivatized to be a proton electron double resonance imaging (PEDRI) probe.

11. A method of measuring oxygen concentration, oxygen partial pressure, or oxygen metabolism in a specific tissue or organ in a subject, the method comprising the steps of:
(a) administering a particulate probe according to claim 1 to the subject; and
(b) applying a magnetic resonance (MR) spectroscopy or imaging technique for measuring $O_2$ concentration in tissues or organs of the subject.

12. The method of claim 11, wherein the MR technique is selected from the group consisting of MRI, ESR, EPR, ERPI, and PEDRI.

13. The method of claim 11 wherein the particulate probe is delivered to the subject intravenously, as a suspension or emulsion.

14. The method of claim 11 wherein the particulate probe is implanted in the tissue or organ of interest.

15. The method of claim 11 wherein the phthalocyanine radical particulate probe is attached to a peptide or glycoconjugate that has specific affinity for cell surface markers, wherein the particulate probe acts as a cell migration marker.

16. The method of claim 11 wherein the particulate probe is attached to an antibody, wherein the antibody has an affinity to cell surface proteins that lead as markers of cell migration, cell division, and cell death.

17. The method of claim 11 wherein the particulate probe remains in the subject for at least 180 days.

18. The method of claim 11 wherein the particulate probe is internalized in live cells, for the study of intracellular oxygenation, cellular hypoxia, cellular hyperoxia, cell division, cellular migration, or metastatis.

19. The method of claim 11 wherein the particulate probe is utilized to study the kinetics of enzymes that involve oxygen consumption and release in organs, tissues, or cells, in the subject.

20. The method of claim 11 wherein the subject is a human subject.

21. The method of claim 11 wherein the particulate probe is used to study microbial oxygen metabolism.

22. A method of measuring nitric oxide (NO), separately or in combination with oxygen, in a specific tissue or organ of a subject, the method comprising the steps of:
(a) administering a particulate probe according to claim 1 to the subject; and
(b) applying a magnetic resonance (MR) spectroscopy technique for measuring NO concentration in tissues or organs of the subject.

* * * * *

UNITED STATES PATENT AND TRADEMARK OFFICE
CERTIFICATE OF CORRECTION

PATENT NO.        : 7,662,362 B2                                          Page 1 of 1
APPLICATION NO.   : 10/935297
DATED             : February 16, 2010
INVENTOR(S)       : Kuppusamy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1380 days.

Signed and Sealed this

Thirtieth Day of November, 2010

David J. Kappos
*Director of the United States Patent and Trademark Office*